(12) United States Patent
Gallo et al.

(10) Patent No.: US 6,319,504 B1
(45) Date of Patent: *Nov. 20, 2001

(54) TREATMENT AND PREVENTION OF HIV INFECTION BY ADMINISTRATION OF DERIVATIVES OF HUMAN CHORIONIC GONADOTROPIN

(75) Inventors: Robert C. Gallo, Bethesda; Joseph Bryant, Rockville; Yanto Lunardi-Iskandar, Gaithersburg, all of MD (US)

(73) Assignee: University of Maryland Biotechnology Institute, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/709,948

(22) Filed: Sep. 9, 1996

Related U.S. Application Data

(63) Continuation-in-part of application No. 08/669,681, filed on Jun. 24, 1996, now abandoned.

(51) Int. Cl.[7] .................................................. A61K 39/00

(52) U.S. Cl. ............................. 424/198.1; 424/184.1; 424/195.11; 514/2; 514/44; 530/350; 530/325; 530/326; 530/327

(58) Field of Search ..................... 424/188.1, 184.1, 424/208.1, 204.1; 514/2, 44; 530/350, 325, 326, 327

(56) References Cited

U.S. PATENT DOCUMENTS

| | | | |
|---|---|---|---|
| 4,123,343 | 10/1978 | Krupey et al. | 806/562 |
| 4,400,316 | 8/1983 | Katsuragi et al. | |
| 4,665,161 | 5/1987 | Yuki et al. | 857/511 |
| 4,689,222 | 8/1987 | McMichael | |
| 4,691,006 | 9/1987 | Stevens | |
| 4,692,332 | 9/1987 | McMichael | |
| 4,762,913 | 8/1988 | Stevens | |
| 4,880,626 * | 11/1989 | McMichael | |
| 4,966,753 | 10/1990 | McMichael | |
| 5,140,100 | 8/1992 | Braunstein et al. | 639/249 |
| 5,141,867 | 8/1992 | Ivanoff et al. | |
| 5,380,668 | 1/1995 | Herron | |
| 5,451,527 | 9/1995 | Sarin et al. | |
| 5,508,261 | 4/1996 | Moyle et al. | |
| 5,610,136 | 3/1997 | McMichael | |
| 5,614,612 | 3/1997 | Haigwood et al. | |
| 5,635,599 | 6/1997 | Pastan et al. | |
| 5,650,390 | 7/1997 | Samaritani et al. | 244/575 |
| 5,674,983 | 10/1997 | Blithe et al. | 448/79 |
| 5,677,275 * | 10/1997 | Lunardi-Iskandar et al. | |
| 5,700,781 | 12/1997 | Harris | 514/21 |
| 5,811,390 | 9/1998 | Bourinbaiar | 514/8 |
| 5,817,753 | 10/1998 | Stevens | 958/601 |
| 5,877,148 | 3/1999 | Lunardi-Iskander et al. | 869/603 |

FOREIGN PATENT DOCUMENTS

| | | |
|---|---|---|
| 0 049 898 B2 | 4/1982 | (EP) . |
| 0 142 387 A1 | 5/1985 | (EP) . |
| 0211013 B1 | 3/1993 | (EP) . |
| WO 87/03487 | 6/1987 | (WO) . |
| WO 90/02759 | 3/1990 | (WO) . |
| WO 91/09872 | 7/1991 | (WO) . |
| WO 91/16921 | 11/1991 | (WO) . |
| WO 92/12178 | 7/1992 | (WO) . |
| WO 92/22654 | 12/1992 | (WO) . |
| WO 93/11788 | 6/1993 | (WO) . |
| WO 94/20859 | 9/1994 | (WO) . |
| WO 94/24148 | 10/1994 | (WO) . |
| WO 95/12299 | 5/1995 | (WO) . |
| WO 96/04008 | 2/1996 | (WO) . |
| WO 96/29095 | 9/1996 | (WO) . |
| WO 97/14428 | 4/1997 | (WO) . |
| WO 99/06438 | 2/1999 | (WO) . |

OTHER PUBLICATIONS

Deshmukh, et al, "Antibody Response Against Three Epitopic . . . " J. Clin. Immunol. 14(3): 162–168, 1994.*

Dirnhoter, et al, "Functional and Immunological Relevance of the . . . " J. Endocrin. 141:153–162, 1994.*

Kardana et al., 1993, "Characterisation of UGP and its relationship with beta–core fragment", Br. J. Cancer 67:686–692.

Mastrangelo et al., 1996, "Gene therapy for human cancer: an essay for clinicians", Sem. Oncology 23:4–21.

Policastro et al., 1983, "The β subunit of human chorionic gonadotropin is encoded by multiple genes", J. Biol. Chem. 258:11492–11499.

(List continued on next page.)

Primary Examiner—Jeffrey Stucker
(74) Attorney, Agent, or Firm—William A. Barrett; Steven J. Hultquist

(57) ABSTRACT

The present invention relates to β-hCG, particularly β-hCG proteins having a sequence of amino acids 41–54, 45–54, 47–53, 45–57 and 45–58 and analogs and derivatives thereof. The invention further relates to methods of treatment and prevention of HIV infection by administration of a therapeutic compound of the invention. Such therapeutic compounds include hCG, β-hCG and β-hCG peptides, analogs and derivatives of hCG, β-hCG and β-hCG peptides, and nucleic acids encoding hCG, β-hCG and β-hCG peptides. In a preferred embodiment, β-hCG peptides, particularly β-hCG peptides of amino acids 47–53, 45–57 or 45–58 are administered to a subject for treatment or prevention of HIV infection in that subject. The invention also provides methods for screening hCG preparations for activity in treating or preventing HIV infection. Pharmaceutical compositions and methods of administration of Therapeutics are also provided.

122 Claims, 17 Drawing Sheets

OTHER PUBLICATIONS

Riddell et al., 1996, "T–cell mediated rejection of gene–modified HIV–specific cytotoxic T lymphocytes in HIV–infected patients", Nat. Med. 2:216–222.
1996 Sigma Product Catalogue, p. 1134.
Barin et al., 1985, Science 228:1094–1096.
Barre–Sinoussi et al., 1983, Science 220:868–870.
Bellet et al., 1984, Endocrinology 115:330–336.
Bidart et al., 1990, Science 248:736–739.
Bidart et al., 1987, J. Biol. Chem. 262:15483–15489.
Bidart et al., 1987, Mol. Immunology 24:339–345.
Blazevic et al., 1995, AIDS Res. Hum. Retroviruses 11:1335–1342.
Bolognesi, 1993, Semin. Immunol. 5:203–214.
Bourinbaiar and Nagorny, 1992, FEMS Microbiol. Lett. 96:27–30.
Bourinbaiar and Lee–Huang, 1995, Immunol. Lett. 44:13–17.
Bourinbaiar and Nagorny, 1992, FEBS Lett. 309:82–84.
Braunstein et al., 1978, J. Clin. Endocrinology and Metabolism 47:326–332.
Caraux et al., 1985, J. Immunol. 134:835–840.
Chen et al., 1992, AIDS 6:533–539.
Clavel et al., 1986, Science 233:343–346.
Cocchi et al., 1995, Science 270:1811–1815.
Creighton, 1993, *Proteins, Structures and Molecular Principles* (W. H. Freeman and Co., New York) pp. 34–49.
Daar et al., Proc. Natl. Acad. Sci. USA 87:6574–6579.
Dalgleish et al., 1984, Nature 312:763–767.
De et al., 1997, J. Clin. Invest. 99:1484–1491.
Delli–Bovi et al., 1986, Cancer Res. 46:6333–6338.
Deshmukh et al., 1994, J. Clin. Immunol. 14:162–168.
Dickie et al., 1991, Virology, 185:109–119.
Dirnhofer et al., 1993, FASEB J. 7:1381–1385.
Dirnhofer et al., 1994, J. Endocrinology 141:153–162.
Ensoli et al., 1989, Science 243:223–226.
Erickson, 1990, Science 249:527–533.
Franks, et al., 1995, Pediatric Res. 37:56–63.
Friedman–Kien et al., 1981, J. Am. Acad. Dermatol. 5:468–473.
Gallo et al., 1984, Science 224:500–503.
Gartner et al., 1986, Science 233:215–219.
Geller et al., 1985, Archs. Path. Lab. Met. 109:138–145.
Gill et al., 1996, New Eng. J. Med. 335:1261–1269.
Guyader et al., 1987, Nature 326:662–669.
Hammarskjold and Rekosh, 1989, Biochem. Biophys. Acta 989:269–280.
Harris, 1995, Lancet 346:118–119.
Hermans, 1995, AIDS Res. Hum. Retroviruses S:96.
Hermans et al., 1995, Cell. Mol. Biol. 3:357–364.
Hutchinson et al., 1978, J. Biol. Chem. 253:6551–6560.
Iyer et al., 1992, Int. J. Pepetide Protein Res. 39:137–144.
Kahn et al., 1990, Ann. Int. Med. 112:254–261.
Kestler et al., 1990, Science 248:1109–1112.
Keutmann et al., 1987, Proc. Natl. Acad. Sci. USA 84:2038–2042.
Keutmann et al., 1988, Biochemistry 27:8939–8944.
Klatzmann et al., 1984, Nature 312:767–768.
Kopp et al., 1993, AIDS Res. Hum. Retroviruses 9:267–275.
Kornyei et al., 1993, Biol. Reprod. 49:1149–1157.
Lapthorn et al., 1994, Nature 369:455–461.
Letvin et al., 1990, J. AIDS 3:1023–1040.
Longhi et al., 1986, J. Immunol. Meth. 92:89–95.
Louache et al., 1992, Blood 180:2991–2999.
Lunardi–Iskandar et al., 1995, Nature 375:64–68.
Lunardi–Iskandar et al., 1989, J. Clin. Invest. 83:610–615.
Lunardi–Iskandar et al., 1989, Leukemia Res. 13:573–581.
Maddon et al., 1986, Cell 47:333–348.
Martin, 1991, *Basic and Chemical Endocrinology* (Appleton & Lange, East Norwalk) pp. 543–567.
Masood et al., 1984, AIDS Res. Hum. Retroviruses 10:969–976.
McDougal et al., 1986, Science, 231:382–385.
Merrifield, 1963, J. Amer. Chem. Soc. 85:2149–2156.
Mitsuya et al., 1991, Science 249:1533–1544.
Van Gemen et al., 1994, J. Virol. Methods 49:157–168.
Varmus, 1988, Science 240:1427–1439.
Vaslin et al., 1994, AIDS Res. Hum. Retroviruses 10:1241–1250.
Ward et al., 1991, *Reproduction in Domestic Animals* (Academic Press, New York) pp. 25–80.
Xia, 1993, J. Mol. Endocrinol. 10:337–343.
Yarchoan et al., 1989, Proc. Vth Int. Conf. on AIDS, p. 564.
Mitsuya et al., 1991, FASEB J. 5:2369–2381.
Nakamura et al., 1988, Science 242:426–430.
Paul, 1994, Cell 82:177–182.
Perelson et al., 1996, Science 15:1582–1586.
Pierce et al., 1991, Rev. Biochem. 50:465–495.
Popescu et al., 1995, JNCI 88:450–454.
Popovic et al., 1984, Science 224:497–500.
Puisieux et al., 1990, Endocrinology 126:687–694.
Ryan et al., 1988, FASEB J. 2:2661–2669.
Salahuddin et al., 1988, Science 242:430–433.
Schooley et al., 1990, Ann. Int. Med. 112:247–253.
Schall, 1991, Cytokine 3:165–183.
Sherman, 1992, J. Mol. Endocrinol. 6:951–959.
Siegal et al., 1990, Cancer 65:492–498.
Smith et al., 1987, Science 238:1704–1707.
Stevens et al., 1986, Immunol. Lett. 12:11–18.
Torres et al., 1987, Immunol. Inv. 16:607–618.
Lundard–Iskander, et al., "Isolation and Characterization of an Immortal Neoplastic Cell Line (KS Y–1) From AIDS–Associated Kaposi's Sarcoma," Journal of the National Cancer Institute, vol. 87. No. 13 Jul. 5, 1995, pp. 974–981.

* cited by examiner

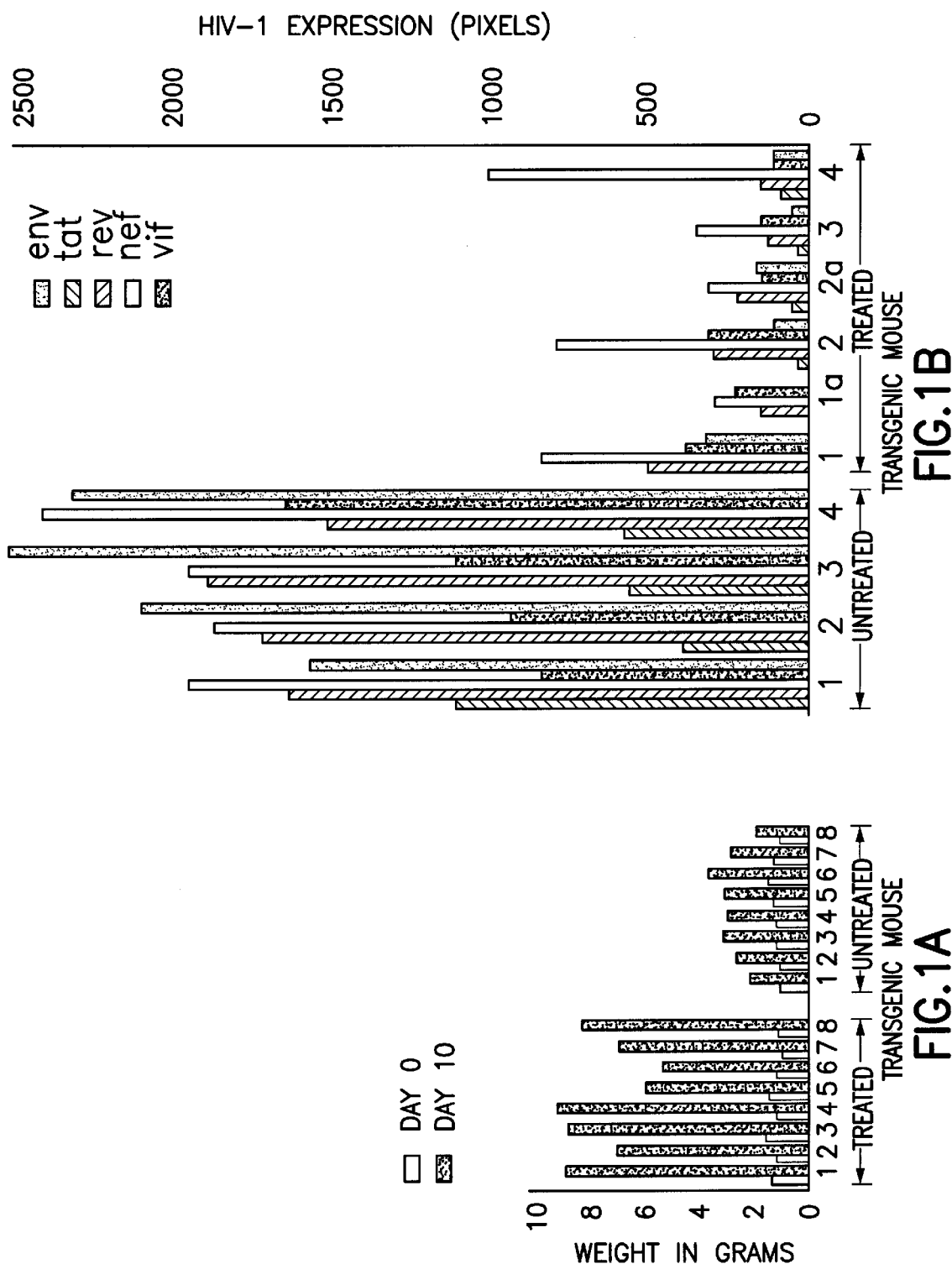

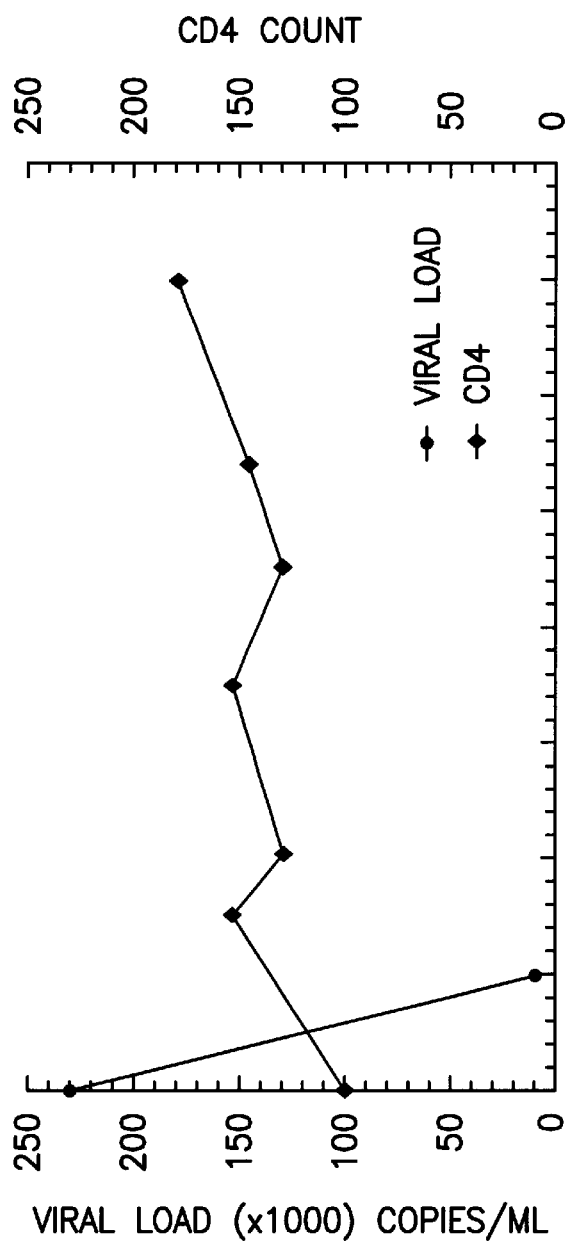
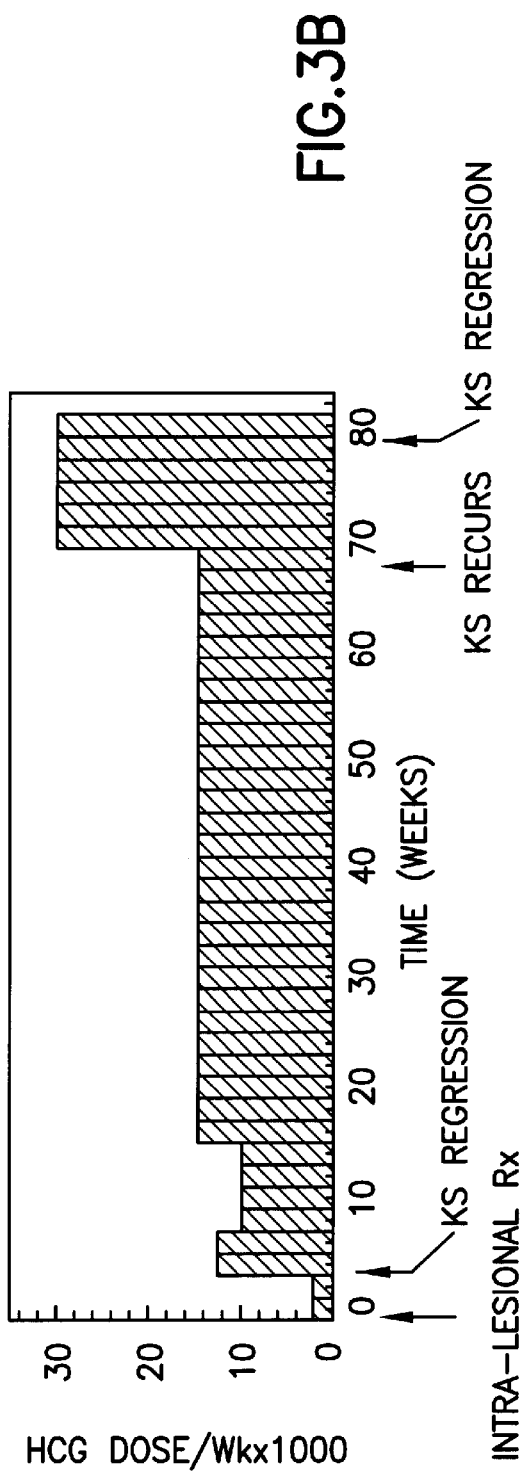
FIG. 3A
FIG. 3B

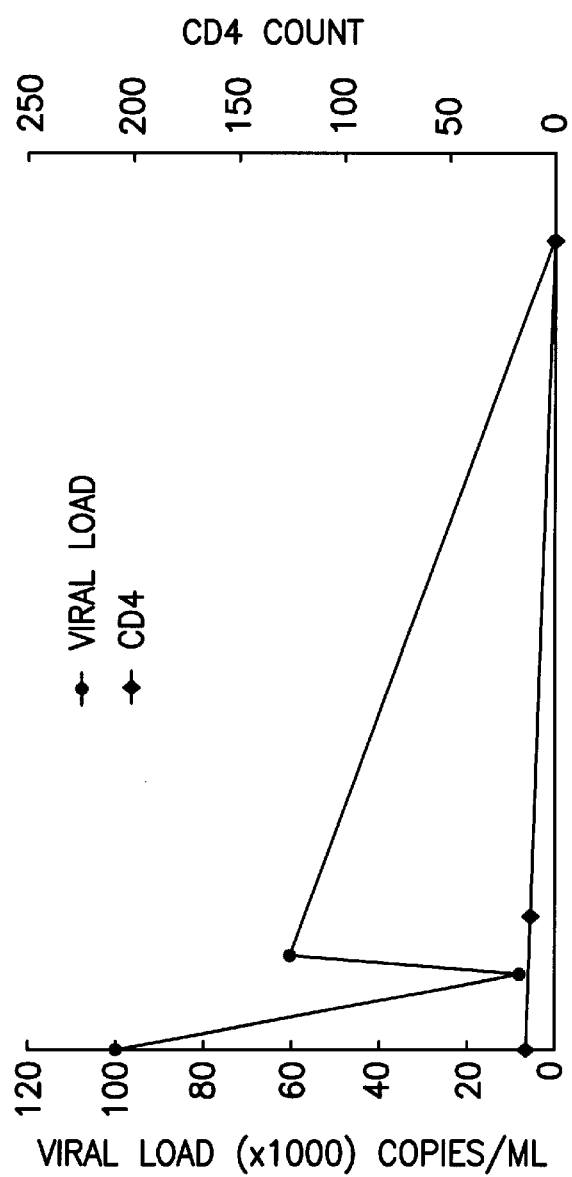
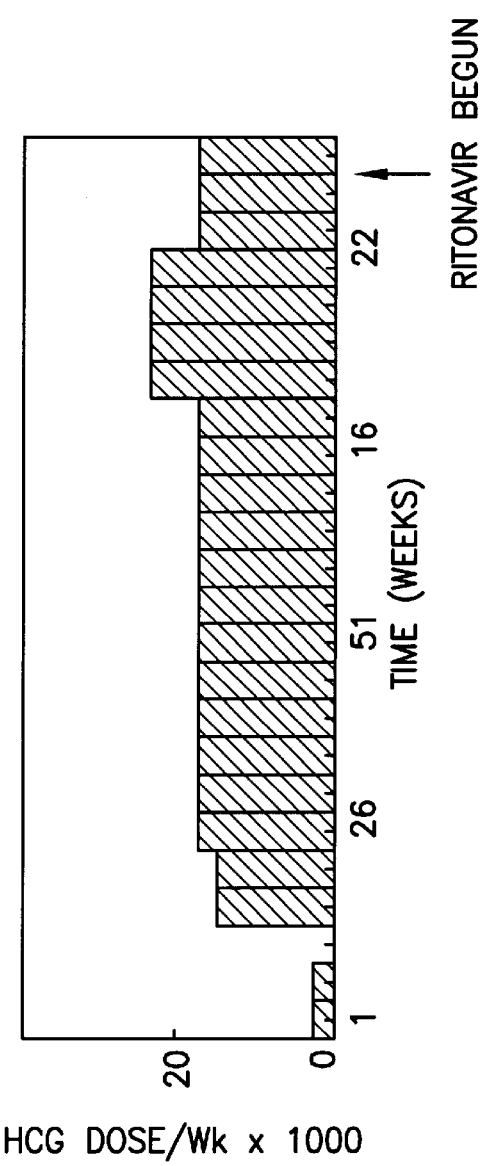
FIG.3E
FIG.3F

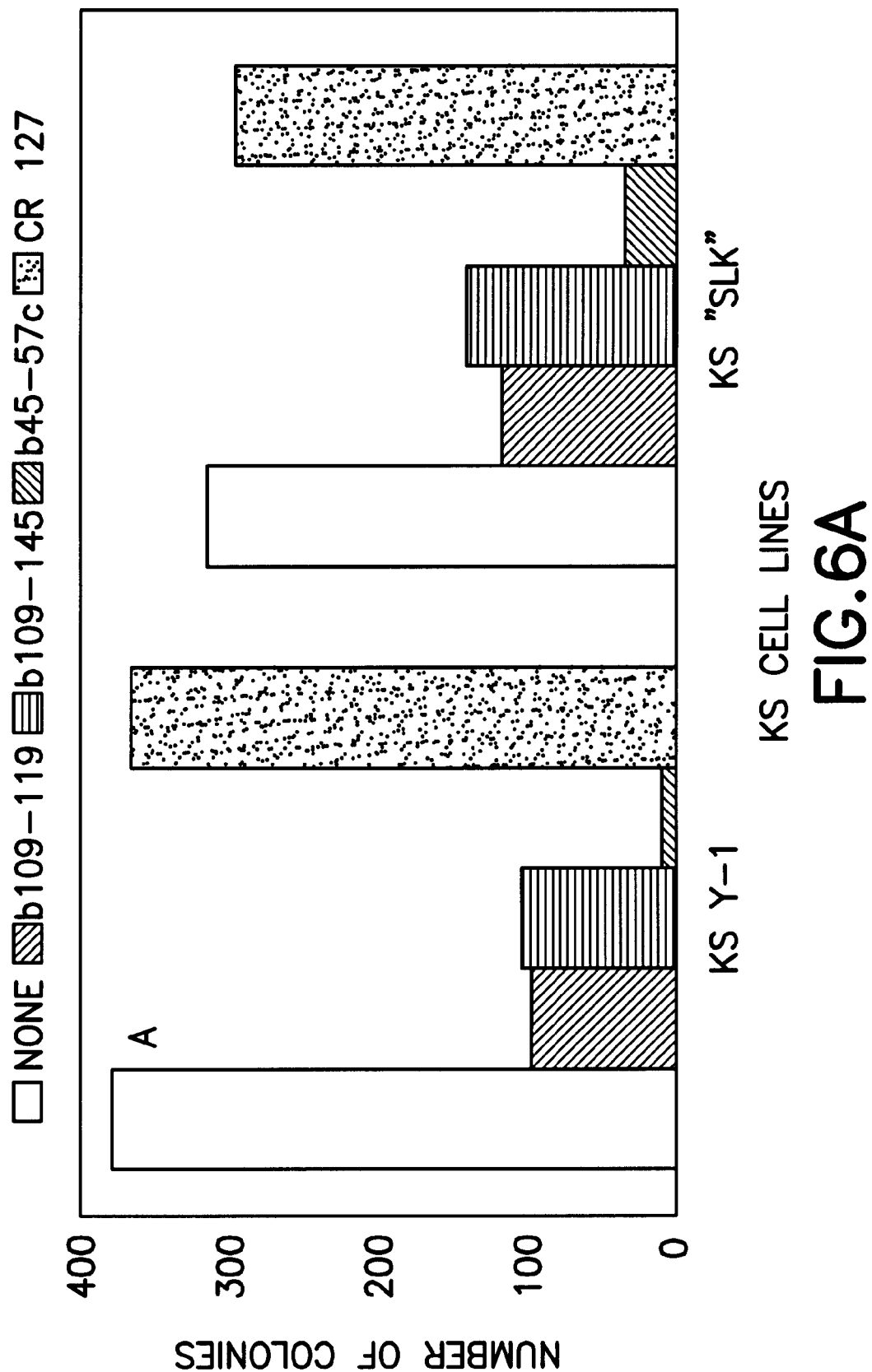

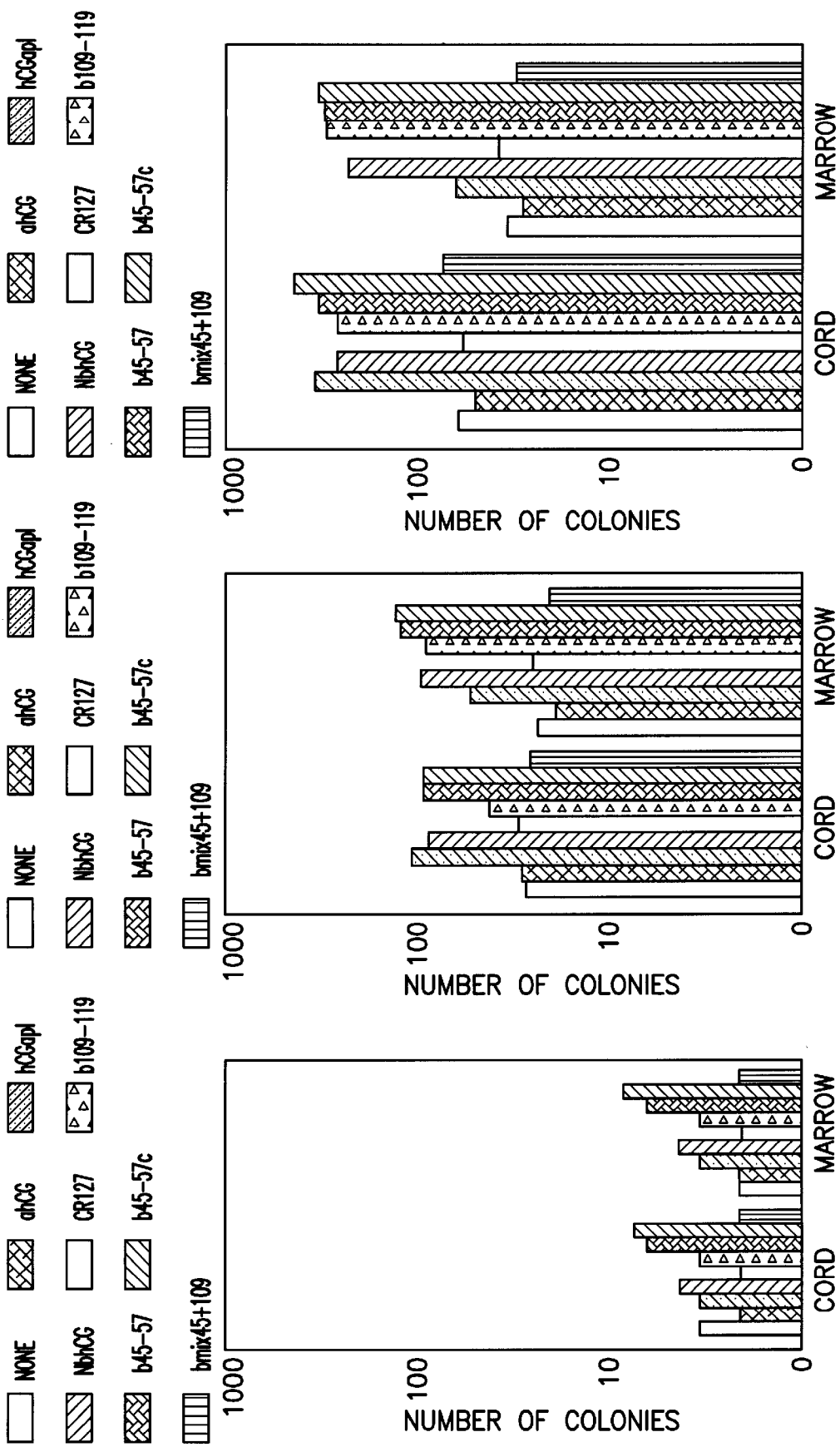

```
AGACAAGGCA GGGGACGCAC CAAGG ATG GAG ATG TTC CAG GGG CTG CTG CTG      52
                             Met Glu Met Phe Gln Gly Leu Leu Leu
                             -20                         -15

TTG CTG CTG CTG AGC ATG GGC GGG ACA TGG GCA TCC AAG GAG CCG CTT     100
Leu Leu Leu Leu Ser Met Gly Gly Thr Trp Ala Ser Lys Glu Pro Leu
            -10                 -5                    1          5

CGG CCA CGG TGC CGC CCC ATC AAT GCC ACC CTG GCT GTG GAG AAG GAG     148
Arg Pro Arg Cys Arg Pro Ile Asn Ala Thr Leu Ala Val Glu Lys Glu
            10                      15                       20
```

FIG.8B

```
GGC TGC CCC GTG TGC ATC ACC GTC AAC ACC ATC TGT GCC GGC TAC    196
Gly Cys Pro Val Cys Ile Thr Val Asn Thr Ile Cys Ala Gly Tyr
         25                  30                  35

TGC CCC ACC ATG ACC CGC GTG CTG CAG GGG GTC CTG CCG GCC CTG CCT    244
Cys Pro Thr Met Thr Arg Val Leu Gln Gly Val Leu Pro Ala Leu Pro
     40                  45                  50

CAG GTG GTG TGC AAC TAC CGC GAT GTG CGC TTC GAG TCC ATC CGG CTC    292
Gln Val Val Cys Asn Tyr Arg Asp Val Arg Phe Glu Ser Ile Arg Leu
 55                  60                  65

CCT GGC TGC CCG CGC GGC GTG AAC CCC GTG TCC TAC GCC GTG GCT    340
Pro Gly Cys Pro Arg Gly Val Asn Pro Val Ser Tyr Ala Val Ala
         70                  75                  80         85

CTC AGC TGT CAA TGT GCA CTC TGC CGC CGC AGC ACC ACT GAC TGC GGG    388
Leu Ser Cys Gln Cys Ala Leu Cys Arg Arg Ser Thr Thr Asp Cys Gly
             90                  95                 100

GGT CCC AAG GAC CAC CCC TTG ACC TGT GAT GAC CCC CGC TTC CAG GAC    436
Gly Pro Lys Asp His Pro Leu Thr Cys Asp Asp Pro Arg Phe Gln Asp
        105                 110                 115
```

```
TCC TCT TCC TCA AAG GCC CCT CCC AGC CTT CCA AGC CCA TCC CGA    484
Ser Ser Ser Lys Ala Pro Pro Pro Ser Leu Pro Ser Pro Ser Arg
        120                 125                 130

CTC CCG GGG CCC TCG GAC ACC CCG ATC CTC CCA CAA TAAAGGCTTC    530
Leu Pro Gly Pro Ser Asp Thr Pro Ile Leu Pro Gln
        135                 140             145

TCAATCCGC                                                      539
```

FIG. 8C

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 539 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 26..520

(xi) SEQUENCE DESCRIPTION: SEQ ID NO:1:

```
AGACAAGGCA GGGGACGCAC CAAGG ATG GAG ATG TTC CAG GGG CTG CTG CTG        52
                            Met Glu Met Phe Gln Gly Leu Leu Leu
                            -20                     -15

TTG CTG CTG CTG AGC ATG GGG GGG ACA TGG GCA TCC AAG GAG CCG CTT       100
Leu Leu Leu Leu Ser Met Gly Gly Thr Trp Ala Ser Lys Glu Pro Leu
    -10                 -5                   1

CGG CCA CGG TGC CGC CCC ATC AAT GCC ACC CTG GCT GTG GAG AAG GAG       148
Arg Pro Arg Cys Arg Pro Ile Asn Ala Thr Leu Ala Val Glu Lys Glu
                10                   15                  20

GGC TGC CCC GTG TGC ATC ACC GTC AAC ACC ACC ATC TGT GCC GGC TAC       196
Gly Cys Pro Val Cys Ile Thr Val Asn Thr Thr Ile Cys Ala Gly Tyr
            25                  30                  35

TGC CCC ACC ATG ACC CGC GTG CTG CAG GGG GTC CTG CCG GCC CTG CCT       244
Cys Pro Thr Met Thr Arg Val Leu Gln Gly Val Leu Pro Ala Leu Pro
        40                  45                  50

CAG GTG GTG TGC AAC TAC CGC GAT GTG CGC TTC GAG TCC ATC CGG CTC       292
Gln Val Val Cys Asn Tyr Arg Asp Val Arg Phe Glu Ser Ile Arg Leu
    55                  60                  65

CCT GGC TGC CCG CGC GGC CTG AAC CCC GTG GTC TCC TAC GCC GTG GCT       340
Pro Gly Cys Pro Arg Gly Leu Asn Pro Val Val Ser Tyr Ala Val Ala
70                  75                  80                  85

CTC AGC TGT CAA TGT GCA CTC TGC CGC CGC AGC ACC ACT GAC TGC GGG       388
Leu Ser Cys Gln Cys Ala Leu Cys Arg Arg Ser Thr Thr Asp Cys Gly
                90                  95                 100

GGT CCC AAG GAC CAC CCC TTG ACC TGT GAT GAC CCC CGC TTC CAG GAC       436
Gly Pro Lys Asp His Pro Leu Thr Cys Asp Asp Pro Arg Phe Gln Asp
               105                 110                 115

TCC TCT TCC TCA AAG GCC CCT CCC CCC AGC CTT CCA AGC CCA TCC CGA       484
Ser Ser Ser Ser Lys Ala Pro Pro Pro Ser Leu Pro Ser Pro Ser Arg
```

```
            120                 125                 130
CTC CCG GGG CCC TCG GAC ACC CCG ATC CTC CCA CAA TAAAGGCTTC          530
Leu Pro Gly Pro Ser Asp Thr Pro Ile Leu Pro Gln
    135                 140                 145

TCAATCCGC                                                           539
```

(2) INFORMATION FOR SEQ ID NO:2:

(i) SEQUENCE CHARACTERISTICS:
        (A) LENGTH: 165 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Met Phe Gln Gly Leu Leu Leu Leu Leu Leu Ser Met Gly
-20             -15                 -10                  -5

Gly Thr Trp Ala Ser Lys Glu Pro Leu Arg Pro Arg Cys Arg Pro Ile
                1               5                   10

Asn Ala Thr Leu Ala Val Glu Lys Glu Gly Cys Pro Val Cys Ile Thr
            15                  20                  25

Val Asn Thr Thr Ile Cys Ala Gly Tyr Cys Pro Thr Met Thr Arg Val
        30                  35                  40

Leu Gln Gly Val Leu Pro Ala Leu Pro Gln Val Val Cys Asn Tyr Arg
45                  50                  55                  60

Asp Val Arg Phe Glu Ser Ile Arg Leu Pro Gly Cys Pro Arg Gly Leu
                65                  70                  75

Asn Pro Val Val Ser Tyr Ala Val Ala Leu Ser Cys Gln Cys Ala Leu
            80                  85                  90

Cys Arg Arg Ser Thr Thr Asp Cys Gly Gly Pro Lys Asp His Pro Leu
        95                  100                 105

Thr Cys Asp Asp Pro Arg Phe Gln Asp Ser Ser Ser Lys Ala Pro
    110                 115                 120

Pro Pro Ser Leu Pro Ser Pro Ser Arg Leu Pro Gly Pro Ser Asp Thr
125                 130                 135                 140

Pro Ile Leu Pro Gln
            145
```

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:3:

```
Met Thr Arg Val Leu Gln Gly Val Leu Pro Ala Leu Pro Gln
1               5                   10
```

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:4:

```
Leu Gln Gly Val Leu Pro Ala Leu Pro Gln
1               5                   10
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:5:

```
Gly Val Leu Pro Ala Leu Pro
1               5
```

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:6:

```
Leu Gln Gly Val Leu Pro Ala Leu Pro Gln Val Val Cys
1               5                   10
```

(2) INFORMATION FOR SEQ ID NO:7:

(i) SEQUENCE CHARACTERISTICS:
        (A) LENGTH: 11 amino acids
        (B) TYPE: amino acid
        (D) TOPOLOGY: both (ii) MOLECULE TYPE: peptide (xi) SEQUENCE DESCRIPTION: SEQ ID NO:7:

```
Thr Cys Asp Asp Pro Arg Phe Gln Asp Ser Ser
1               5                   10
```

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:8:

```
Met Thr Arg Val Leu Gln Gly Val Leu Pro Ala Leu Pro
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:9:

```
Thr Arg Val Leu Gln Gly Val Leu Pro Ala Leu Pro
1               5                   10
```

(2) INFORMATION FOR SEQ ID NO:10:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:10:

```
Arg Val Leu Gln Gly Val Leu Pro Ala Leu Pro
1               5                   10
```

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:11:

```
Val Leu Gln Gly Val Leu Pro Ala Leu Pro
1               5                   10
```

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:12:

```
Val Leu Gln Gly Val Leu Pro Ala Leu Pro Gln Val Val Cys
1               5                   10
```

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:13:

```
Leu Gln Gly Val Leu Pro Ala Leu Pro
1               5
```

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:14:

```
Gln Gly Val Leu Pro Ala Leu Pro
1               5
```

(2) INFORMATION FOR SEQ ID NO:15:

(i) SEQUENCE CHARACTERISTICS:

(A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:15:

Leu Gln Gly Val Leu Pro Ala Leu Pro Gln
1               5                   10

(2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:16:

Leu Gln Gly Val Leu Pro Ala Leu Pro Gln Val
1               5                   10

(2) INFORMATION FOR SEQ ID NO:17:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:17:

Leu Gln Gly Val Leu Pro Ala Leu Pro Gln Val Val
1               5                   10

(2) INFORMATION FOR SEQ ID NO:18:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:18:

Leu Gln Gly Val Leu Pro Ala Leu Pro Gln Val Val Cys Asn
1               5                   10

(2) INFORMATION FOR SEQ ID NO:19:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:19:

Gly Val Leu Pro Ala Leu Pro Gln
1               5

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:20:

Gly Val Leu Pro Ala Leu Pro Gln Val
1               5

(2) INFORMATION FOR SEQ ID NO:21:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:21:

Gly Val Leu Pro Ala Leu Pro Gln Val Val
1               5                   10

(2) INFORMATION FOR SEQ ID NO:22:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO:22:

Gly Val Leu Pro Ala Leu Pro Gln Val Val Cys Asn
1               5                   10

(2) INFORMATION FOR SEQ ID NO:23:

(i) SEQUENCE CHARACTERISTICS:
            (A) LENGTH: 98 amino acids
            (B) TYPE: amino acid
            (D) TOPOLOGY: linear (ii) MOLECULE TYPE: peptide (xi) SEQUENCE DESCRIPTION: SEQ ID NO:23:

Val Leu Pro Ala Leu Pro Gln Val Val Cys Asn Tyr Arg Asp Val Arg
1               5                   10                  15

Phe Glu Ser Ile Arg Leu Pro Gly Cys Pro Arg Gly Leu Asn Pro Val
                20                  25                  30

Val Ser Tyr Ala Val Ala Leu Ser Cys Gln Cys Ala Leu Cys Arg Arg
            35                  40                  45

Ser Thr Thr Asp Cys Gly Gly Pro Lys Asp His Pro Leu Thr Cys Asp
        50                  55                  60

Asp Pro Arg Phe Gln Asp Ser Ser Ser Lys Ala Pro Pro Pro Ser
65                  70                  75                  80

Leu Pro Ser Pro Ser Arg Leu Pro Gly Pro Ser Asp Thr Pro Ile Leu
                85                  90                  95

Pro Gln (2) INFORMATION FOR SEQ ID NO:24:

(i) SEQUENCE CHARACTERISTICS:
            (A) LENGTH: 88 amino acids
            (B) TYPE: amino acid
            (D) TOPOLOGY: linear (ii) MOLECULE TYPE: peptide

```
      (xi) SEQUENCE DESCRIPTION: SEQ ID NO:24:

Asn Tyr Arg Asp Val Arg Phe Glu Ser Ile Arg Leu Pro Gly Cys Pro
1               5                   10                  15

Arg Gly Leu Asn Pro Val Val Ser Tyr Ala Val Ala Leu Ser Cys Gln
                20                  25                  30

Cys Ala Leu Cys Arg Arg Ser Thr Thr Asp Cys Gly Gly Pro Lys Asp
            35                  40                  45

His Pro Leu Thr Cys Asp Asp Pro Arg Phe Gln Asp Ser Ser Ser Ser
        50                  55                  60

Lys Ala Pro Pro Pro Ser Leu Pro Ser Pro Ser Arg Leu Pro Gly Pro
65                  70                  75                  80

Ser Asp Thr Pro Ile Leu Pro Gln
                85

(2) INFORMATION FOR SEQ ID NO:25:

(i) SEQUENCE CHARACTERISTICS:
          (A) LENGTH: 37 amino acids
          (B) TYPE: amino acid
          (D) TOPOLOGY: linear (ii) MOLECULE TYPE: peptide (xi) SEQUENCE DESCRIPTION: SEQ ID NO:25:

Thr Cys Asp Asp Pro Arg Phe Gln Asp Ser Ser Ser Ser Lys Ala Pro
1               5                   10                  15

Pro Pro Ser Leu Pro Ser Pro Ser Arg Leu Pro Gly Pro Ser Asp Thr
                20                  25                  30

Pro Ile Leu Pro Gln
        35

(2) INFORMATION FOR SEQ ID NO:26:

(i) SEQUENCE CHARACTERISTICS:
          (A) LENGTH: 14 amino acids
          (B) TYPE: amino acid
          (D) TOPOLOGY: circular (ii) MOLECULE TYPE: peptide (xi) SEQUENCE DESCRIPTION: SEQ ID NO:26:

Cys Leu Gln Gly Val Leu Pro Ala Leu Pro Gln Val Val Cys
1               5                   10
```

TREATMENT AND PREVENTION OF HIV INFECTION BY ADMINISTRATION OF DERIVATIVES OF HUMAN CHORIONIC GONADOTROPIN

CROSS REFERENCE TO RELATED APPLICATION

This application is a continuation in part of application Ser. No. 08/669,681, filed Jun. 24, 1996, now abandoned, which is incorporated by reference herein in its entirety.

FIELD OF THE INVENTION

The present invention relates to peptides containing a sequence of a portion of the human chorionic gonadotropin β-chain as well as methods for treatment and prevention of HIV infection using human chorionic gonadotropin, the β-chain of human chorionic gonadotropin and peptides containing a sequence of a portion of the β-chain of human chorionic gonadotropin and derivatives thereof, for the treatment and prevention of HIV infection. The present invention further relates to pharmaceutical compositions for the treatment and prevention of HIV infection.

BACKGROUND OF THE INVENTION

THE HUMAN IMMUNODEFICIENCY VIRUS

The human immunodeficiency virus (HIV) has been implicated as the primary cause of the slowly degenerative immune system disease termed acquired immune deficiency syndrome (AIDS) (Barre-Sinoussi, F., et al., 1983, Science 220:868–870; Gallo, R., et al., 1984, Science 224:500–503). There are at least two distinct types of HIV: HIV-1 (Barre-Sinoussi, F., et al., 1983, Science 220:868–870; Gallo, R., et al., 1984, Science 224:500–503) and HIV-2 (Clavel, F., et al., 1986, Science 233:343–346; Guyader, M., et al., 1987, Nature 326:662–669). Further, a large amount of genetic heterogeneity exists within populations of each of these types. In humans, HIV replication occurs prominently in CD4$^+$ T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses (Teich, N., et al., 1984, RNA Tumor Viruses, Weiss, R., et al., eds., CSH-Press, pp. 949–956). Retroviruses are small enveloped viruses that contain a single-stranded RNA genome, and replicate via a DNA intermediate produced by a virally-encoded reverse transcriptase, an RNA-dependent DNA polymerase (Varmus, H., 1988, Science 240:1427–1439).

The HIV viral particle comprises a viral core, composed in part of capsid proteins, together with the viral RNA genome and those enzymes required for early replicative events. Myristylated gag protein forms an outer shell around the viral core, which is, in turn, surrounded by a lipid membrane envelope derived from the infected cell membrane. The HIV envelope surface glycoproteins are synthesized as a single 160 kilodalton precursor protein which is cleaved by a cellular protease during viral budding into two glycoproteins, gp41 and gp120. gp41 is a transmembrane glycoprotein and gp120 is an extracellular glycoprotein which remains non-covalently associated with gp41, possibly in a trimeric or multimeric form (Hammarskjold, M., & Rekosh, D., 1989, Biochem. Biophys. Acta 989:269–280).

HIV is targeted to CD4$^+$ cells because a CD4 cell surface protein (CD4) acts as the cellular receptor for the HIV-1 virus (Dalgleish, A., et al., 1984, Nature 312:763–767; Klatzmann et al., 1984, Nature 312:767–768; Maddon et al., 1986, Cell 47:333–348). Viral entry into cells is dependent upon gp120 binding the cellular CD4 receptor molecules (McDougal, J. S., et al., 1986, Science 231:382–385; Maddon, P. J., et al., 1986, Cell 47:333–348), explaining HIV's tropism for CD4$^+$ cells, while gp41 anchors the envelope glycoprotein complex in the viral membrane. While these virus:cell interactions are necessary for infection, there is evidence that additional virus:cell interactions are also required.

HIV TREATMENT

HIV infection is pandemic and HIV-associated diseases represent a major world health problem. Although considerable effort is being put into the design of effective Therapeutics, currently no curative anti-retroviral drugs against AIDS exist. In attempts to develop such drugs, several stages of the HIV life cycle have been considered as targets for therapeutic intervention (Mitsuya, H., et al., 1991, FASEB J. 5:2369–2381). Many viral targets for intervention with HIV life cycle have been suggested, as the prevailing view is that interference with a host cell protein would have deleterious side effects. For example, virally encoded reverse transcriptase has been one focus of drug development. A number of reverse-transcriptase-targeted drugs, including 2', 3'-dideoxynucleoside analogs such as AZT, ddI, ddC, and d4T have been developed which have been shown to been active against HIV (Mitsuya, H., et al., 1991, Science 249:1533–1544).

The new treatment regimens for HIV-1 show that a combination of anti-HIV compounds, which target reverse transcriptase (RT), such as azidothymidine (AZT), lamivudine (3TC), dideoxyinosine (ddI), dideoxycytidine (ddC) used in combination with an HIV-1 protease inhibitor have a far greater effect (2 to 3 logs reduction) on viral load compared to AZT alone (about 1 log reduction). For example, impressive results have recently been obtained with a combination of AZT, ddI, 3TC and ritonavir (Perelson, A. S., et al., 1996, Science 15:1582–1586). However, it is likely that long-term use of combinations of these chemicals will lead to toxicity, especially to the bone marrow. Long-term cytotoxic therapy may also lead to suppression of CD8$^+$ T cells, which are essential to the control of HIV, via killer cell activity (Blazevic, V., et al., 1995, AIDS Res. Hum. Retroviruses 11:1335–1342) and by the release of suppressive 35 factors, notably the chemokines Rantes, MIP-1α and MIP-1β (Cocchi, F., et al., 1995, Science 270:1811–1815). Another major concern in long-term chemical anti-retroviral therapy is the development of HIV mutations with partial or complete resistance (Lange, J. M., 1995, AIDS Res. Hum. Retroviruses 10:S77–82). It is thought that such mutations may be an inevitable consequence of anti-viral therapy. The pattern of disappearance of wild-type virus and appearance of mutant virus due to treatment, combined with coincidental decline in CD4$^+$ T cell numbers strongly suggests that, at least with some compounds, the appearance of viral mutants is a major underlying factor in the failure of AIDS therapy. Attempts are also being made to develop drugs which can inhibit viral entry into the cell, the earliest stage of HIV infection. Here, the focus has thus far been on CD4, the cell surface receptor for HIV. Recombinant soluble CD4, for example, has been shown to inhibit infection of CD4$^+$ T cells by some HIV-1 strains (Smith, D. H., et al., 1987, Science 238:1704–1707). Certain primary HIV-1 isolates, however, are relatively less sensitive to inhibition by recombinant CD4 (Daar, E., et al., 1990, *Proc. Natl. Acad. Sci. USA* 87:6574–6579). In addition, recombinant soluble CD4 clinical trials have produced inconclusive results (Schooley, R., et al., 1990, *Ann. Int. Med.* 112:247–253; Kahn, J. O., et al., 1990, *Ann. Int. Med.* 112:254–261; Yarchoan, R., et al., 1989, Proc. Vth Int. Conf. on AIDS, p. 564, MCP 137).

The late stages of HIV replication, which involve crucial virus-specific processing of certain viral encoded proteins, have also been suggested as possible anti-HIV drug targets. Late stage processing is dependent on the activity of a viral protease, and drugs are being developed which inhibit this protease (Erickson, J., 1990, *Science* 249:527–533).

Recently, chemokines produced by $CD8^+$ T cells have been implicated in suppression of HIV infection (Paul, W. E., 1994, *Cell* 82:177; Bolognesi, D. P., 1993, *Semin. Immunol.* 5:203). The chemokines RANTES, MIP-1α and MIP-1β, which are secreted by $CD8^+$ T cells, were shown to suppress HIV-1 p24 antigen production in cells infected with HIV-1 or HIV-2 isolates in vitro (Cocchi, F, et al., 1995, *Science* 270:1811–1815). Thus, these and other chemokines may prove useful in therapies for HIV infection. The clinical outcome, however, of all these and other candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin et al., 1985, *Science* 228:1094–1096). Thus far, therefore, these proteins seem to be the most promising candidates to act as antigens for anti-HIV vaccine development. Several groups have begun to use various portions of gp160, gp120, and/or gp41 as immunogenic targets for the host immune system. See for example, Ivanoff, L., et al., U.S. Pat. No. 5,141,867; Saith, G., et al., WO92/22,654; Shafferman, A., WO91/09,872; Formoso, C., et al., WO90/07,119. To this end, vaccines directed against HIV proteins are problematic in that the virus mutates rapidly rendering many of these vaccines ineffective. Clinical results concerning these candidate vaccines, however, still remain far in the future.

Thus, although a great deal of effort is being directed to the design and testing of anti-retroviral drugs, effective, non-toxic treatments are still needed.

HUMAN CHORIONIC GONADOTROPIN

Human chorionic gonadotropin (hCG), which is required for the maintenance of pregnancy, is a member of the glycoprotein hormone family. The glycoprotein hormones, which also include follicle-stimulating hormone (FSH), luteinizing hormone (LH) and thyroid-stimulating hormone (TSH), consist of two sub-units, α and β. These subunits are non-covalently linked to form a heterodimer, and heterodimer formation has been shown to be required for receptor binding. Within a particular species, the α-subunits are identical among the glycoprotein hormones while the β-subunits differ and determine the receptor binding specificity of the particular hormone (Kornyei, J. L., et al., 1993, *Biol. Reprod.* 49:1149). The β-subunits of the glycoprotein hormones exhibit a high degree of sequence similarity within the N-terminal 114 amino acids. LH is the most similar to hCG with 85% sequence homology within the first 114 amino acids, and both proteins bind the same receptor. hCG, however, contains a C-terminal extension not present in the other glycoprotein β-chains (Lapthorn, A. J., et al., 1994, *Science* 369:455–461).

From the three dimensional crystal structure of hCG, it was determined that hCG, like the growth factors nerve growth factor (NGF), transforming growth factor-β (TGF-β) and platelet-derived growth factor-β(PDGF-β), is a cysteine-knot glycoprotein. Proteins containing such a cysteine-knot motif have at least three disulfide bridges, two of which join adjacent anti-parallel strands of the peptide, thus, forming a ring, and one of which joins the peptide chain through the ring. Particular structures in the hCG β-chain include the determinant loop sequence (β93–100) which has been implicated in subunit association and the longest inter-cysteine loop (β38–57) which may play a role in receptor binding. Residues 47-53 appear to be exposed at the surface of this inter-cysteine loop (Lapthorn et al., 1994, *Nature* 369:455–461).

Previously, purified preparations of heterodimeric hCG have been shown to reduce the reverse transcriptase activity in HIV-1 infected lymphocytes and monocytes in culture (Bourinbaiar, A. S., and Nagorny, R., 1992, *FEMS Microbiology Letters* 96:27–30) and to prevent transmission of HIV from lymphocytes to trophoblasts in vitro (Bourinbaiar, A. S., and Nagorny, R., 1992, *FEBS Letters* 309:82–84). Additionally, the β-subunit of hCG (β-hCG) has been demonstrated to reduce HIV production in lymphocytes at doses from 100 pg/ml to 100 μg/ml and in monocytes at doses up to approximately 10 μg/ml, with higher doses actually increasing the level of viral production in monocytes (Bourinbaiar, A. S., and Lee-Huang, S., 1995, *Immunology Letters* 44:13–17). However, none of these reports disclose the potential efficacy of β-hCG peptides in HIV inhibition in vitro or of hCG or any portion or derivative thereof in HIV treatment or prevention in vivo.

Furthermore, doses of hCG below those necessary to induce a humoral immune response have been proposed for treatment of HIV infection based on observations of therapeutic effects of such doses on cats and cows infected with feline leukemia and bovine leukemia viruses respectively (U.S. Pat. No. 4,880,626). This patent suggested use of the hCG dimer at very low doses (approximately 2 I.U. per treatment).

Lunardi-Iskandar et al. (1995, *Nature* 375:64–68 and PCT Application WO96/04008) reported that hCG, β-hCG, as well as a β-hCG carboxy-terminal peptides of amino acids 109–145 (SEQ ID NO:25) and 109–119 (SEQ ID NO:7) are efficacious in the treatment of Kaposi's Sarcoma. However, neither reference discloses or even suggests that hCG, β-hCG or β-hCG peptides of amino acids 109–145 or 109–119 (SEQ ID NOS:7 and 25, respectively) have any viral anti-activity or that other β-hCG peptides have any therapeutic activity.

Finally, Harris (1995, The Lancet 346:118–119) reported that treatment with hCG improved T cell counts and physical symptoms in certain HIV infected subjects.

Citation of references hereinabove shall not be construed as an admission that such references are prior art to the present invention.

SUMMARY OF THE INVENTION

The present inventors have found that hCG preparations, β-hCG preparations and certain peptides of β-hCG exhibit anti-viral activities. In particular, hCG and β-hCG preparations, as described by way of example herein below, and specific peptides thereof inhibit HIV-1 replication in vitro, inhibit HIV-1 gene-expression in HIV-1 transgenic mice, reduce plasma virus levels in SIV infected monkeys and in AIDS patients, and increase $CD4^+$ T cells in HIV transgenic mice, SIV infected monkeys and AIDS patients. The present inventors have further found that the subjects tolerated treatment with hCG and β-hCG very well and that the virus did not become resistant to treatment after exposure to hCG or β-hCG. The present invention fills a tremendous need for a non-toxic, long-term treatment of HIV infection and its sequelae, ARC and AIDS.

The present invention relates to proteins having a sequence of a portion of the β-chain of hCG (β-hCG), particularly proteins having the sequence of amino acid numbers 41–54, 45–54, 47–53, 45–57 and 109–119 (SEQ ID NOS:3–7, respectively) of β-hCG as depicted in FIG. 8 (a portion of SEQ ID NO:2). The present invention further relates to therapeutic methods and compositions for treatment and prevention of diseases and disorders associated with HIV-1 infection based on hCG and β-hCG preparations and therapeutically and prophylactically effective proteins containing a sequence of a portion of β-hCG, and related derivatives and analogs. The invention provides for treatment and prevention of HIV infection by administration of a therapeutic compound of the invention. The therapeutic compounds of the invention include: hCG, β-hCG, therapeutically and prophylactically effective peptides having a sequence of a portion of β-hCG, modified derivatives of hCG, β-hCG and β-hCG peptides, and nucleic acids encoding β-hCG and therapeutically and prophylactically effective peptides having a sequence of a portion of β-hCG, and derivatives and analogs of the foregoing. The invention also provides in vitro and in vivo assays for assessing the efficacy of therapeutics of the invention for treatment or prevention of HIV. The invention also provides pharmaceutical compositions and methods of administration of therapeutics of the invention for treatment or prevention of HIV infection.

DEFINITIONS

As used herein, the following terms shall have the meaning indicated.

| | |
|---|---|
| AIDS | Acquired Immune Deficiency Syndrome |
| ARC | AIDS-Related Complex |
| hCG | Human Chorionic Gonadotropin |
| KS | Kaposi's Sarcoma |
| OI | Opportunistic Infection |
| PBMC | Peripheral Blood Mononuclear Cell |

DESCRIPTION OF THE FIGURES

FIGS. 1A and B. Effects of an hCG preparation, hCG (APL), on weight and HIV-1 gene expression in HIV-1 transgenic mice. (A) Weight change in grams in individual HIV-1 transgenic mice (labelled as 1–8) either treated with hCG, "treated", or not treated with hCG, "untreated", from day 1 to day 10 of treatment is represented as a bar graph. Open bars represent the weight of individual mice at day 0 and solid bars represent the weight of-the individual mice at day 10. (B) Suppression of HIV-1 gene expression in transgenic mice either treated with hCG (APL) preparation "treated" or not treated with hCG "untreated". The bar graph presents the level of expression in pixels, as determined by chemiluminescence assay of the HIV genes env, tat, rev, nef, and vif in the individual HIV transgenic mice. The bars with black background and white circles represent env expression, the striped bars represent tat expression, the bars with rectangles in the pattern represent rev expression, the open bars represent nef expression, and the solid bars represent vif expression. The results are the average of 8 mice in each group (labelled as 1–4), but all treated mice (30 of 30) showed a marked decrease in HIV expression.

FIGS. 3A–F. Effects of some hCG preparations on HIV-1 viral load, CD4+ T cell levels, and weight over extended periods in individual patients with advanced HIV infection. (A and B) Bar graphs depicting the results from hCG treatment of patient PH-VE (see Table 1) over time in weeks. (A) Graph presents data of CD4+ T cell count in mm$^3$ (line with diamonds) and viral load as copies×1000/ml plasma (line with circles). (B) Graph documents the status of the patient's Kaposi's sarcoma with respect to the dosages of hCG administered, indicated as IU×1000/week. At week 0, intralesional therapy began; at week 3, regression of KS lesions was observed; at week 68, KS lesions recurred; and at week 79, KS lesion regression was observed. (C and D) Bar graphs depicting the results of hCG treatment of patient PH-SPBE (see Table 1) over time in weeks. (C) Graph presents data of CD4+ T cell count in mm$^3$ (line with diamonds) and viral load as copies (×1000)/ml plasma (line with circles). (D) Bar graph indicates the dosage of hCG per week in IU×1000. It is noted under the graph that ritonavir therapy was begun at 20 weeks of therapy. (E and F) Bar graphs depicting the results from hCG treatment of patient PH-VE (see Table 1) over time in weeks. (E) Graph presents data of CD4+ T cell count in mm$^3$ (line with diamonds) and viral load as copies (×1000)/mL plasma (line with circles). (F) Bar graph indicates the dosage of hCG per week in IU×1000. It is noted under the graph that ritonavir therapy was begun after 20 weeks of therapy.

PBMCs infected with HIV-1 IIIB. In both graphs, results with α-hCG subunit are represented by lines with diamonds, results with the β-hCG peptide 6–16 by lines with squares, results with the β-hCG peptide 109–119 by lines with stars, results with the circularized β-hCG peptide 44–57 (with cysteine substituted for the amino acid at position 44) (SEQ ID NO:26) by lines with triangles, and results with the α-hCG peptide 88–92 by lines with inverted triangles. (C and D) These graphs depict data on the effect of α-hCG, hCG peptides and commercial hCG preparations on the infection of primary macrophages by HIV-1 Ba-L. (C) Effect of different concentrations of hCG α subunits and various hCG peptides (0.05 to 50 nmol/ml) on infection in peripheral blood macrophages from a normal donor infected with HIV-1 Ba-L. The results are averages of triplicate samples with less than 15% variation. Results with α-hCG subunit are represented by lines with diamonds, results with the β-hCG peptide 6–16 by lines with squares, results with the β-hCG peptide 109–119 (SEQ ID NO:7) by lines with stars, results with the circularized β-hCG peptide 44–57 (with cysteine substituted for the amino acid at position 44) (SEQ ID NO:26) by lines with triangles, and results with the α-hCG peptide 88–92 by lines with inverted triangles. (D) A comparison of the inhibition of HIV Ba-L infection of macrophages by different commercial native hCG preparations (APL, Wyeth Ayerst; Steris, Steris; Pregnyl, Organon) and by purified hCG (CR127) over a concentration range of 0.05 IU to 1,000 IU/ml. Results are shown at day 10. Results with hCG-APL are indicated by a line with inverted triangles, results with hCG-Steris are indicated by a line with circles, results with hCG-Pregnyl are indicated by a line with squares, and results with hCG-CR127 are indicated by a line with X's.

Figure 5A:
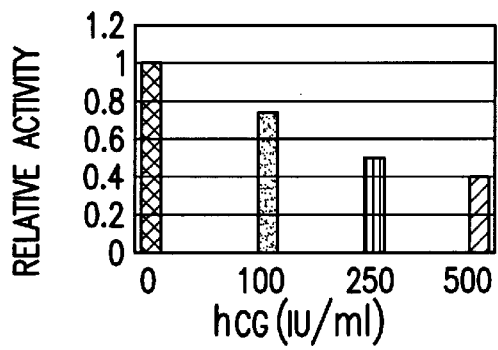
Figure 5B:
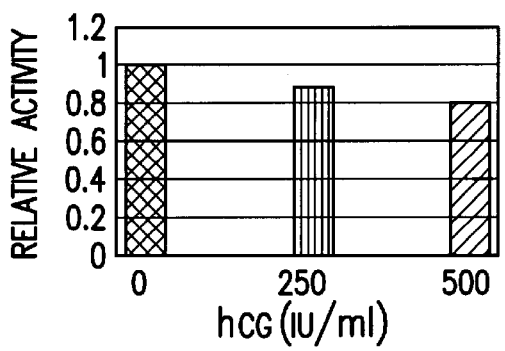
Figure 5C:
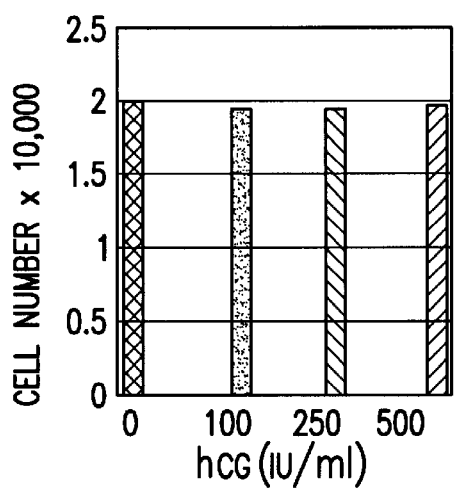

FIGS. 5A–C. Effect of preparations of hCG on HIV-LTR activity. (AN The CAT activity of cells containing the HIV-LTR construct and treated with hCG concentrations of 0 IU/ml, 100 IU/ml, 250 IU/ml and 500 IU/ml was calculated relative to the untreated control. (B) Relative CAT activity of the unrelated SV40 promoter in response to hCG at 0 IU/ml, 250 IU/ml and 500 IU/ml was similarly calculated. Data in both A and B represents the mean +/–S.E.M. of 3 to 7 independent experiments and is presented as a bar graph. The different hCG concentrations are indicated in both A and B as depicted below:

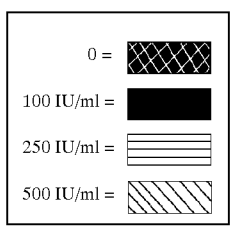

(C) The viability of Hut 78 cells in the presence of hCG at 0 IU/ml, 250 IU/ml and 500 IU/mrl under the conditions used in the transient expression assays shown in Figures A and B was determined using a coulter cell counter. Results are presented as a bar graph in terms of cell number×10,000 and the hCG concentrations are indicated as shown below:

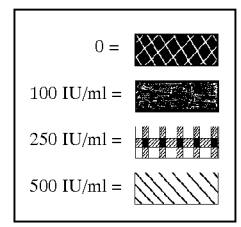

FIGS. 6A–H. Effect of hCG preparations and peptides on KS colony growth in vitro and KS tumors in vivo. (A) Comparison of the anti-KS in vitro effects (tumor cell killing) of purified hCG and g-hCG peptides in KS clonogenic assays using KS Y-12 and KS "SKL"18 cells depicted in a bar graph in terms of number of colonies. The results are averages of 3 sets of results with less than 10% variation and are representative of multiple experiments. Results with no hCG or hCG peptides are represented by open bars, the results with the β-hCG peptide of amino acids 109–119 (SEQ ID NO:7) are represented by stippled bars, the results with the β-hCG peptide of amino acids 109–145 (SEQ ID NO:25) are represented by the bars with horizontal stripes, the results with the circular β-hCG peptide of amino acids 44–57 (SEQ ID NO:26) where the amino acid at position 44 is a cysteine are represented by the bars with diagonal stripes, and the results with the highly purified hCG preparation, CR 127, are represented by solid bars. (B–H) Thin sections of KS tumors induced in nude mice by inoculation with 106 neoplastic KS Y-1 cells. (B) Thin section of tumors from mice that were not treated with hCG or hCG subunits or peptides (C) Thin section of a tumor from a mouse after treatment with crude hCG APL (100 IU) subcutaneously daily for 7 days. (D) Thin section of a tumor from a mouse treated with the β-hCG peptide of amino acids 45–57 (SEQ ID NO:6), 10 μg/ml/daily (6.7 nmoles) for 5 days. (E) Thin section of a tumor from a mouse after 5 days of treatment with the circularized β-hCG peptide 44–57 (SEQ ID NO:26), where cysteine has been substituted at position 44, at 10 μg per day. (F) This panel shows the thin tissue section of KS tumor from AIDS-KS patients treated with 1 ml of diluent alone shows less than 2% cell death as detected by specific apoptosis in situ immunostaining. (G) Thin tissue section of KS tumor from an AIDS-KS patient after hCG preparation therapy of intralesional injections of 2000 IU, 3 times weekly for 2–3 weeks, shows evidence of apoptosis in all cells. (H) Thin tissue section of KS tumor from an AIDS-KS patient after hCG preparation therapy, 500 IU, 3 times weekly for 3 weeks.

FIGS. 7A–C. These bar graphs demonstrate the effects of hCG preparations and peptides on hematopojesis in vitro. (A) This bar graph depicts results of colony assays in terms of number of colonies for CFU-MIX (colony forming units of megakaryocytes, erythrocytes, granulocytes and monocytes). (B) This bar graph presents data from colony assays for BFU-e (Burst forming units of erythrocytes) in terms of number of colonies. (C) This bar graph presents results from colony assays of CFU-GM (colony forming units of giranulo-macrophages) in terms of number of colonies For all three graphs, results are shown for cells isolated from cord blood ("cord") and bone marrow ("marrow"). The results are averages of 3 sets of results with less than 10% variation and are representative of multiple experiments. The results from no treatment are indicated by open bars; the results with α-hCG are represented by solid bars; the results with hCG-APL (hCGapl) are represented by bars with a lattice pattern; the results with native β-hCG preparation (NbhCG) are represented by cross-hatched bars; the results with the highly purified hCG preparation (CR127) are represented by open bars; the results with the β-hCG peptiyde of amino acids 109–119 (SEQ ID NO:7) (b109–119) are shown by the diagonally stippled bars; the results with the β-hCG peptide of amino acids 45–57 (SEQ ID NO:6) (b45–57) are shown by the bars with the diamonds; the results with the circularized β-hCG peptide of amino acids 44–57 (ID NO:26) with cysteine substituted for the amino acid at position 44 (b45–57c) are represented by the diagonally striped bars; and the results with the mixture of scrambled β-hCG peptides of amino acids 45–57 and 109–119 (bmix45+109) are represented by the vertically striped bars.

FIG. 8. Nucleotide and amino acid sequences of β-hCG (SEQ ID NOS:1 and 2).

Figure 9A:
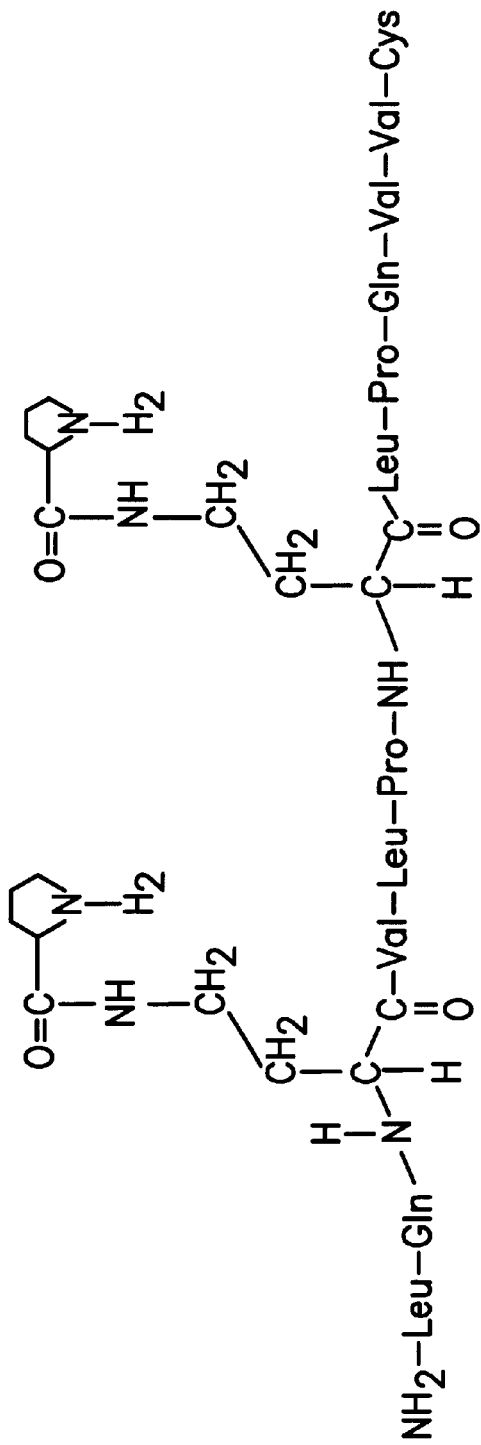

FIGS. 9A and B. Schematic depiction of the structures of (A) the linear peptide of amino acids 45–57 (SEQ ID NO:6) of the β-hCG sequence depicted in FIG. 8 (SEQ ID NO:2) where the amino acid residues at positions 47 and 51 are substituted by a branch made up of diaminobutyric acid peptide bonded to proline, and (B) the circularized peptide of amino acids 44–57 (SEQ ID NO:12) with valine at position 44 substituted with cysteine, which protein is circularized via a disulfide bond between its amino- and carboxy-terminal cysteines. In both A and B, amino acids are represented by their three letter amino acid code, except for the branched residues and the terminal cysteines, for which the structure is depicted.

DETAILED DESCRIPTION OF THE INVENTION

The present invention relates to proteins (including peptides) containing a sequence of a portion of β-hCG (β-hCG peptides) that are effective at inhibiting HIV replication and/or infection in vitro or in vivo, decreasing viral load, and/or treating or preventing disorders associated with HIV infection. In specific embodiments, the invention provides an isolated protein, the amino acid sequence of which consists of amino acid numbers 41–54, 45–54, 47–53 or 45–57 (SEQ ID NOS:3–6, respectively) of the β-hCG sequence depicted in FIG. 8 (a portion of SEQ ID NO:2), particularly to an isolated protein spanning amino acids 45–57 (SEQ ID NO:5) of FIG. 8 (a portion of SEQ ID NO:2). The present invention further relates to therapeutic methods and compositions for treatment and prevention of disorders associated with HIV infection based on hCG and β-hCG preparations and therapeutically and prophylactically effective β-hCG peptides. The invention provides for treatment of HIV infection by administration of a therapeutic compound of the invention. The therapeutic compounds of the invention include: hCG, β-hCG, therapeutically and prophylactically effective β-hCG peptides, related derivatives and analogs of hCG, β-hCG or β-hCG peptides, and nucleic acids encoding β-hCG and β-hCG peptides, and analogs and derivatives thereof. β-hCG peptides which are effective for treatment and prevention of HIV infection can be identified by in vitro and in vivo assays such as those described in Section 5.3, infra.

In a preferred embodiment, a therapeutic composition of the invention comprises a β-hCG peptide, the amino acid sequence of which consists of amino acid numbers 41–53, 42–53, 43–53, 44–53, 44–57, 45–53, 46–53, 45–54, 45–55, 45–56, 45–58, 47–54, 47–55, 47–56, 47–58, 48–145, 58–145 or 109–145 (SEQ ID NOS:8–25, respectively) of FIG. 8 (a portion of SEQ ID NO:2), particularly a β-hCG peptide which consists of amino acid numbers 41–54, 45–54 or 109–119 (SEQ ID NOS:3, 4, or 7, respectively), most preferably of a β-hCG peptide which consists of amino acids 47–53 (SEQ ID NO:5) or 45–57 (SEQ ID NO:6). In other preferred embodiments, the therapeutic comprises a β-hCG peptide, the amino acid sequence of which consists of circularized (via a disulfide bond between its amino- and carboxy- terminal cysteines) 44–57 (SEQ ID NO:26) with the valine at position 44 substituted with cysteine ((Val44Cys) 45–57 circularized) (depicted in FIG. 9B), 45–57 (SEQ ID NO:6) where the amino acid residues at positions 47 and 51 are substituted by a branch, where the branches are made up of diaminobutyric acid peptide bonded to a proline residue (depicted in FIG. 9A). The amino acid sequence of β-hCG is depicted in FIG. 8 (SEQ ID NO:2).

For clarity of disclosure, and not by way of limitation, the detailed description of the invention is divided into the subsections which follow.

β-hCG PEPTIDES AND DERIVATIVES THEREOF

The invention provides isolated proteins (e.g., peptides), the amino acid sequences of which consist of a portion of the β-hCG sequence (β-hCG peptides), which are effective for treatment or prevention of HIV infection and resulting disorders. In various specific embodiments, the portions of the β-hCG sequence are at least 3, 5, 10, 20, or amino acids. Effectiveness of the peptides of the invention for treatment or prevention of HIV infection can be determined by any of the methods disclosed in Section 5.3 infra or by any method known in the art. In a specific embodiment, the peptides inhibit HIV infection or replication. In a preferred embodiment, the invention relates to proteins, the amino acid sequences of which consist of amino acid numbers 41–54, 45–54, 47–53 and 45–57 (SEQ ID NOS:3–6) of the β-hCG sequence depicted in FIG. 8 (a portion of SEQ ID NO:2). In other embodiments, proteins, the amino acid sequences of which, consist of amino acid numbers 41–53, 42–53, 43–53, 44–53, 44–57, 45–53, 46–53, 45–54, 45–55, 45–56, 45–58, 47–54, 47–55, 47–56, 47–58, 48–145, 58–145, 109–119 and 109–145 (SEQ ID NOS:8–24, 7, and 25, respectively) of FIG. 8 (a portion of SEQ ID NO:2) are also provided. In another embodiment, the peptides of the invention (i) have an amino acid sequence consisting of no more than 8 peptides of the β-hCG sequence (FIG. 8 (SEQ ID NO:2)) and (ii) comprise amino acid numbers 47–53 (SEQ ID NO:5) of β-hCG (FIG. 8 (SEQ ID NO:2)). In another embodiment, the invention provides an isolated protein which protein (a) comprises a portion of the amino acid sequence of β-hCG, a peptide consisting of said portion being effective to inhibit HIV infection or replication; and (b) lacks β-hCG amino acids contiguous to said portion. In a specific embodiment, the invention provides an isolated protein (a) comprising a β-hCG amino acid sequence consisting of amino acid numbers 41–54, 45–54, 47–53, 45–57, 45–58, 41–53, 42–53, 43–53, 44–53, 44–57, 45–53, 46–53, 45–54, 45–55, 45–56, 47–54, 47–56, 47–58, or 58–145 (SEQ ID NOS:3–6, 18, 8–17, 19, 21, 22, or 24, respectively) as depicted in FIG. 8 (a portion of SEQ ID NO:2); and (b) lacking β-hCG amino acids contiguous to said sequence. Peptides containing the above sequences in which only conservative substitutions have been made are also provided by the present invention, as but one example of peptide derivatives within the scope of the invention. Analogs of the above-mentioned proteins and peptides which have one or more amino acid substitutions forming a branched peptide (e.g., by substitution with an amino acid or amino acid analog having a free amino- or carboxy-side chain that forms a peptide bond with a sequence of one or more amino acids, including but not limited to prolines) or allowing circularization of the peptide (e.g., by substitution with a cysteine, or insertion of a cysteine at the amino- or carboxy-terminus or internally), to provide a sulfhydryl group for disulfide bond formation, are also provided. The peptides of the invention may also have utility for uses other than treatment or prevention of HIV, for example but not limited to, the uses disclosed in the U.S. Patent Applications filed on even date herewith, entitled "Treatment and Prevention of Cancer by Administration of Derivatives of Human Chorionic gonadotropin", by Gallo et al., Ser. No. 08/709,925 [(ATTORNEY DOCKET NO. 8769-017)]; "Methods of Promoting Hematopoesis Using Derivatives of Human Chorionic Gonadotropin", by Gallo et al,. Ser. No. 08/709,924 [ATTORNEY DOCKET NO. 8769-018)]; and "Treatment and Prevention of Wasting Syndrome Based on Administration of Derivatives of Human Chorionic Gonadotropin"By Gallo et al., Ser. No. 08/709,933 [(Attorney Docket No. 8769-019)] entitled "Treatment and Prevention of Cancer by Administration of Derivatives of Human Chorionic Gonadotropin", by Gallo et al., Serial No. 08/669,676, filed Jun. 24, 1996; "Methods of Promoting Hematopoiesis Using Derivatives of Human Chorionic Gonadotropin", by Gallo et al., Ser. No. 08/669,654, filed Jun. 24, 1996; and "Treatment and Prevention of Wasting Syndrome Based on Administration of Derivatives of Human Chorionic Gonadotropin"by Gallo et al., Serial No. 08/669,675, filed Jun. 24, 1996, all of which are incorporated herein by reference in their entireties.

In specific embodiments, peptides of less than 50, or less than 25, amino acids are provided.

The invention also relates to derivatives, modifications and analogs of β-hCG peptides. In one embodiment, β-hCG peptide derivatives can be made by altering the β-hCG peptide sequence by substitutions, additions or deletions that provide for therapeutically effective molecules. Thus, the β-hCG peptide derivatives include peptides containing, as a primary amino acid sequence, all or part of the particular β-hCG amino acid sequence including altered sequences in which functionally equivalent amino acid residues are substituted for residues within the sequence resulting in a peptide which is functionally active. For example, one or mcre amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such β-hCG peptide derivatives can be made either by chemical peptide synthesis or by recombinant production from nucleic acid encoding the β-hCG peptide which nucleic acid has been mutated. Any technique for mutagenesis known in the art can be used, including but not limited to, chemical mutagenesis, in vitro site-directed mutagenesis (Hutchinson, C., et al., 1978, *J. Biol. Chem* 253:6551), use of TAB® linkers (Pharmacia), etc.

In addition, β-hCG peptides and analogs and derivatives of β-hCG peptides can be chemically synthesized. (See, e.g., Merrifield, 1963, *J. Amer. Chem. Soc.* 85:2149–2156.) For example, peptides can be synthesized by solid phase techniques, cleaved from the resin, and purified by preparative high performance liquid chromatography (e.g., see Creighton, 1983, Proteins, Structures and Molecular Principles, W.H. Freeman and Co., N.Y., pp. 50–60). β-hCG peptides can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49). Furthermore, if desired, nonclassical amino acids or chemical amino acid analogs can be introduced as a substitution or addition into the β-hCG peptide. Non-classical amino acids include but are not limited to the D-isomers of the common amino acids, 2,4-diaminobutyric acid, β-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

By way of example but not by way of limitation, peptides of the invention can be chemically synthesized and purified as follows: Peptides can be synthesized by employing the N-α-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection with 20% piperdine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in peptide synthesis, the resin can be allowed to swell for more efficient coupling by increasing the time of mixing in the initial DMF washes to three 15 minute washes rather than three 30 second washes. After peptide synthesis, the peptide can be cleaved from the resin as follows: (1) washing the peptide-resin three times for 30 seconds with DMF; (2) removing the Fmoc protective group on the amino terminus by washing two times for 15 minutes in 20% piperdine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% triisopropysilane with the peptide-resin for two hours, then filtering the peptide in the cleavage cocktail away from the resin, and precipitating the peptide out of solution by addition of two volumes of ethyl ether. To isolate the peptide, the ether-peptide solution can be allowed to sit at −20° C. for 20 minutes, then centrifuged at 6000×G for 5 minutes to pellet the peptide, and the peptide can be washed three times with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

In a preferred embodiment, the invention provides a peptide with branched amino acids (branched peptide), preferably a branched peptide of amino acids 45–57 (SEQ ID NO:6) with branches occurring at positions 47 and 51, respectively, instead of the Gly and Ala residues normally present. Most preferably, diaminobutyric acid is substituted for the gly and ala residues at positions 47 and 51, respectively, and proline bonded to both diaminobutyric acid residues (45–57 branched) as shown in FIG. 9A.

In other specific embodiments, branched versions of the β-hCG peptides listed hereinabove are provided, e.g., by substituting one or more amino acids within the β-hCG sequence with an amino acid or amino acid analog with a free side chain capable of forming a peptide bond with one or more amino acids (and thus capable of forming a "branch").

Branched peptides may be prepared by any method known in the art for covalently linking any naturally occurring or synthetic amino acid to any naturally occurring or synthetic amino acid in a peptide chain which has a side chain group able to react with the amino or carboxyl group on the amino acids so as to become covalently attached to the peptide chain. In particular, amino acids with a free amino side chain group, such as, but not limited to, diaminobutyric acid, lysine, arginine, ornithine, diaminopropionic acid and citrulline, can be incorporated into a peptide so that an amino acid can form a branch therewith, for example, by forming a peptide bond to the free amino side group, from that residue. Alternatively, amino acids with a free carboxyl side chain group, such as, but not limited to, glutamic acid, aspartic acid and homocitrulline, can be incorporated into the peptide so that an amino acid can form a branch therewith, for example, by forming a peptide bond to the free carboxyl side group, from that residue. The amino acid forming the branch can be linked to a side chain group of an amino acid in the peptide chain by any type of covalent bond, including, but not limited to, peptide bonds, ester bonds and disulfide bonds. In a specific embodiment, amino acids, such as those described above, that are capable of forming a branch point, are substituted for β-hCG residues within a peptide having a β-hCG sequence.

Figure 9B:
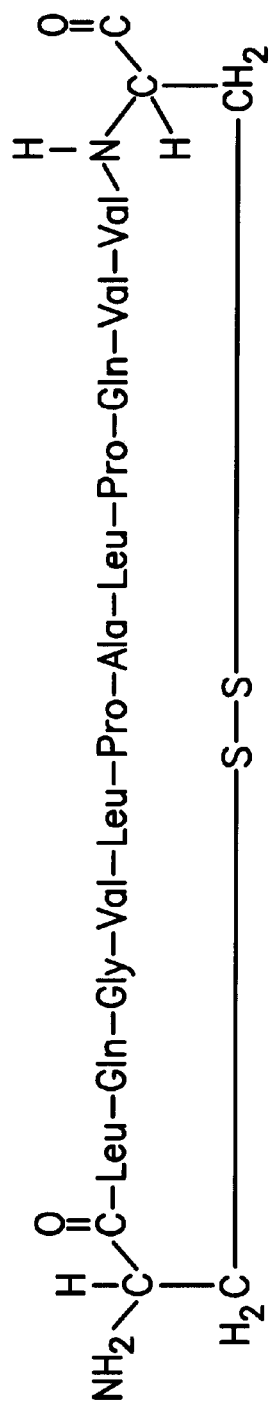

Branched peptides can be prepared by any method known in the art. For example, but not by way of limitation, branched peptides can be prepared as follows: (1) the amino acid-to be branched from the main peptide chain can be purchased as an N-β-tert-butyloxycarbonyl (Boc) protected amino acid pentafluorophenyl (Opfp) ester and the residue within the mtlain chain to which this branched amino acid will be attached can be an N-Fmoc-α-γ-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dinmethylaminopyridine and allowing the solution to mix for 24 hours; (3) the peptide can then be extracted from the 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12 N HCl; (4) the solution containing the peptide can be dehydrated by adding 2–5 grams magnesium sulfate, filtering out the magnesium sulfate, and evaporating the remaining solution to a volume of about 2–5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared analogously to the procedure described above, using the N-F-moc coupled form of the amino acid or amino acid analog. In a preferred embodiment, the peptide is a cyclic peptide, preferably a cyclic peptide of β-hCG amino acids 44–57 (SEQ ID NO:26) with cysteine substituted for valine at position 44 and circularized via a disulfide bond between the cysteine residues at positions 44 and 57 (C[V44C] 45–57) (FIG. 9B). In another preferred embodiment, the peptide is a cyclic branched peptide of β-hCG amino acids 44–57 (SEQ ID NO:12) with cysteine substituted for valine at position 44 and circularized via a disulfide bond between the cysteinie residues at positions 44 and 57 and positions 47 and 51 substituted with a diaminobutyric acid residue on which a proline is peptide bonded to its free amino sidechain.

Cyclization can be, for example but not by way of limitation, via a disulfide bond between two cysteine residues or via an amide linkage. For example, but not by way of limitation, disulfide bridge formation can be achieved by (1) dissolving the purified peptide at a concentration of between 0.1–0.5 mg/ml in 0.01 M ammonium acetate, pH 7.5; (2) adding 0.01 M potassium ferricyanide to the dissolved peptide dropwise until the solution appears pale yellow in color and allowing this solution to mix for 24 hours; (3) concentrating the cyclized peptide to 5–10 ml of solution, repurifying the peptide by reverse phase-high pressure liquid chromatography (RP-HPLC) and finally lyophilizing the peptide. In a specific embodiment, in which the peptide does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge. Alternatively, a cyclic peptide can be obtained by generating an amide linkage. An amide linkage can be achieved by, for example, but not limited to, the following procedure: An allyl protected amino acid, such as aspartate, glutamate, asparagine or glutamine, can be incorporated into the peptide as the first amino acid, and then the remaining amino acids coupled on. The allyl protective group can be removed by a two hour mixing of the peptide-resin with a solution of tetrakistriphenylphophine palladium (0) in a solution of chloroform containing 5% acetic acid and 2.5% N-methylmorpholine. The peptide resin can be washed three times with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperdine in DMF, and washed three times with DMF for 30 seconds each. The activator mix, N-methylmorpholine and HBTU in DMF, can be brought onto the column and allowed to couple the free amino terminal end to the carboxyl group generated by removal of the alLyl group to cyclize the peptide. The peptide can cleaved from the resin as described in the general description of chemical peptide synthesis above and the peptide purified by reverse phase-high pressure liquid chromatography (RP-HPLC). In a specific embodiment, in which the peptide to be cyclized does not contain an allyl protected amino acid, an allyl protected amino acid can be introduced into the sequence of the peptide, at the amino-terminus, carboxy-terminus or internally, such that the peptide can be cyclized.

β-hCG peptides can also be obtained by recombinant expression techniques. (See, e.g., Sambrook et al., 1989, Molecular Cloning, A Laboratory Manual, Cold Spring Harbor Laboratory, 2d Ed., Cold Spring Harbor, N.Y., Glover, D. M. (ed.), 1985, DNA Cloning: A Practical Approach, MRL Press, Ltd., Oxford, U.K., Vol. I, II). The nucleic acid sequence encoding hCG has been cloned and the sequence determined (FIG. 8 (SEQ ID NOS:1 and 2) and Xia, H., 1993, *J. Molecular Endocrinology Jun.* 10; 1993:337–343; Sherman, G.B., 1992, *J. Molecular Endocrinology*, Jun. 6, 1992:951–959; Gieseman, L. K. (ed.), 1991, *Basic and Chemical Endocrinology*, pp. 543–567; Ward et al., 1991, in *Reproduction in Domestic Animals,* 4th ed., P. T. Coppos, ed., pp. 25–80, Academic Press, New York) and can be isolated using well-known techniques in the art, such as screening a library, chemical synthesis, or polymerase chain reaction (PCR).

To recombinantly produce a β-hCG peptide, a nucleic acid sequence encoding β-hCG or a β-hCG peptide is operatively linked to a promoter such that β-hCG or a β-hCG peptide is produced from said sequence. For example, a vector can be introduced into a cell, within which cell the vector or a portion thereof is expressed, producing β-hCG or a portion thereof. In a preferred embodiment, the nucleic acid is DNA if the source of RNA polymerase is DNA-directed RNA polymerase, but the nucleic acid may also be RNA if the. source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art. Vectors can be plasmid, viral, or others known in the art, used for replication and expression in bacterial or mammalian cells. Expression of the sequence encoding β-hCG or the β-hCG peptide can be by any promoter known in the art to act in bacterial or mammalian cells. Such promoters can be inducible or constitutive. Such promoters include, but are not limited to: the SV40 early promoter region (Bernoist and Chambon, 1981, *Nature* 290:304–310), the promoter contained in the 3' long terminal repeat of Rous sarcoma virus (Yamamoto et al., 1980, Cell 22:787–797), the HSV-1 (herpes simplex virus-1) thymidine kinase promoter (Wagner et al., 1981, *Proc. Natl. Acad. Sci. USA* 78:1441–1445), the regulatory sequences of the metallothionein gene (Brinster et al., 1982, Nature 296:39–42), etc., as well as the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, *Cold Spring Harbor Symp. Quant. Biol.* 50:399–409; MacDonald, 1987, Hepatology 7: 425–515); insulin gene control region which is active in pancreatic beta cells (Hanahan, 1985, *Nature* 315:115–122), immunoqlobulin gene control region which is active in lymphoid cells (Grosschedl et al., 1984, *Cell* 38:647–658; Adames et al., 1985, Nature 318:533–538; Alexander et al., 1987, *Mol. Cell. Biol.* 7:1436–1444), mouse mammary tumor virus control region which is active in testicular, breast, lymphoid and mast cells (Leder et al., 15 1986, Cell 45:485–495), albumin gene control region which is active in liver (Pinkert et al., 1987,.*Genes and Devel.* 1:268–276), alpha-fetoprotein gene control region which is active in liver (Krumlauf et al., 1985, *Mol. Cell. Biol.* 5:1539–1648; Hammer et al., 1987, *Science* 235:53–58), alpha 1-antitr-ypsin gene control region which is active in the liver (Kelsey et al., 1987, *Genes and Devel.* 1:161–171), beta-globin gene control region which is active in erythroid cells (Mogram et al., 1985, *Nature* 315:338–340; Kollias et al., 1986, Cell 46, 89–94), myelin basic protein gene control region which is active in oligodendrocyte cells in the brain (Readhead et al., 1987, Cell 48:703–712), myosin light chain-2 gene control region which is active in skeletal muscle (Sani, 1985, *Nature* 314:283–286), and gonadotropin releasing hormone gene control region which is active in the hypothalamus (Mason et al., 1986, *Science* 234:1372–1378). The promoter element which is operatively linked to the nucleic acid encoding β-hCG or a β-hCG peptide can also be a bacteriophage promoter with the source of the bacteriophage RNA polymerase expressed from a gene for the RNA polymerase on a separate plasmid, e.g., under the control of an inducible promoter, for example, the nucleic acid encoding β-hCG or β-hCG peptide operatively linked to the T7 RNA polymerase promoter with a separate plasmid encoding the T7 RNA polymerase.

In a less preferred embodiment, peptides can be obtained by proteolysis of hCG followed by purification using standard techniques such as chromatography (e.g., HPLC), electrophoresis, etc.

Also included within the scope of the invention are β-hCG peptide derivatives which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus. Any of numerous chemical modifications may be carried out by known techniques, including but not limited to acetylation, formylation, oxidation, reduction; metabolic synthesis in the presence of tunicamycin; etc.

In another embodiment, the β-hCG or- β-hCG peptide derivative is a chimeric, or fusion, protein comprising β-hCG or a functional β-hCG peptide joined at its amino- or carboxy-terminus via a peptide bond to an amino acid sequence of a different protein. In a specific embodiment, the derivative is a fusion protein comprising the β-hCG sequence, or portion thereof, joined at its amino or carboxy-terminus to an amino acid sequence, or portion thereof, of a chemokine which is therapeutically useful in the treatment of AIDS, for example, the chemokines MIP-1α, MIP-1β or Rantes (for amino acid sequences of these chemokines see Shall, 1991, *Cytokine* 30 3:165–183). In one embodiment, such a chimeric protein is produced by recombinant expression of a nucleic acid encoding the protein (comprising a β-hCG-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

THERAPEUTIC USES

The invention provides for treatment or prevention of diseases and disorders associated with HIV infection by administration of a therapeutic compound (termed herein "Therapeutic"). Such "Therapeutics" include, but are not limited to hCG, β-hCG and therapeutically and prophylactically effective β-hCG peptides, i.e., those peptides which prevent or treat HIV infection (e.g., as demonstrated in in vitro and in vivo assays described infra), and derivatives and analogs thereof, as well as nucleic-acids encoding hCG, β-hCG and therapeutically and prophylactically effective β-hCG peptides and derivatives and analogs thereof (e.g., for use in gene therapy). Examples of Therapeutics are those proteins described in Section 5.1 and nucleic acids encoding such proteins.

A preferred embodiment of the invention relates to methods of using a Therapeutic for treatment or prevention of HIV infection, preferably HIV-1 infection, in a human subject. In a specific embodiment, the Therapeutic is used for the treatment or prevention of HIV infection in a human subject that does not suffer from a cancer which secretes hCG or hCG fragments. In another specific embodiment, the Therapeutic is used for the treatment or prevention of HIV infection in a human subject who does not suffer from Kaposi's sarcoma (KS). In the treatment of HIV infection, the Therapeutic of the invention can be used to prevent progression of HIV-1 infection to ARC or to AIDS in a human patient, or to treat a human patient with ARC or AIDS.

In a preferred aspect of the invention, proteins, preferably β-hCG peptides are used to treat HIV infection. In particular, proteins, or nucleic acids encoding the proteins, containing an amino acid sequence of a portion of β-hCG, preferably containing a sequence from amino acids 41–53, 42–53, 43–53, 44–53, 44–57, 45–53, 46–53, 45–54, 45–55, 45–56, 45–58, 47–54, 47–55, 47–56, 47–58, 48–145, 58–145, or 109–145 (SEQ ID NOS:8–25, respectively) of FIG. 8 (a portion of SEQ ID NO:2), and preferably containing a sequence from amino acids 41–54, 45–54 or 109–119 (SEQ ID NOS:3, 4 or 7, respectively) of FIG. 8 (a portion of SEQ ID NO:2), and most preferably containing a sequence from amino acids 47–53 or 45–57 of FIG. 8 (a portion of SEQ ID NO:2), or circular [C44V] 45–57 peptide (SEQ ID NO:26), or branched 45–57 (SEQ ID NO:6) peptide, or branched circular [V44C] 45–57 peptide are used to treat HIV infection. In another embodiment, a protein is used that (a) comprises a β-hCG amino acid sequence consisting of amino acid numbers 41–54, 45–54, 47–53, 45–57, 45–58, 41–53, 42–53, 43–53, 44–53, 44–57, 45–53, 46–53, 45–54, 45–55, 45–56, 47–54, 47–55, 47–56, 47–58, 48–145, 58–145, 109–119, or 109–145 (SEQ ID NOS:3–6, 18, 8–17, 19–24, 7, or 25, respectively) as depicted in FIG. 8 (a portion of SEQ ID NO:2) and (b) lacks β-hCG amino acids contiguous to said sequence. In yet another embodiment, a purified derivative of a protein is used to treat or prevent HIV infection, the amino acid sequence of which protein is selected from the group consisting of amino acid numbers 41–54, 45–54, 47–53, 45–57, 45–58, 41–53, 42–53, 43–53, 44–53, 44–57, 45–53, 46–53, 45–54, 45–55, 45–56, 47–54, 47–55, 47–56, 47–58, 48–145, 58–145, 109–119, or 109–145 (SEQ ID NOS:3–6, 18, 8–17, 19–24, 7, or 25, respectively) as depicted in FIG. 8 (a portion of SEQ ID NO:2). Other β-hCG peptides, and nucleic acids encoding the peptides, and modifications and derivatives thereof, may have utility in the therapeutic methods of the invention. The utility of β-hCG peptides may be determined by the in vitro and in vivo assays described in Section 5.3 infra or by any other method known in the art.

Additionally, the present inventors have found that different preparations of hCG and β-hCG have variable effects on HIV infection both in vitro and in vivo. Specifically, the inventors found that among the commercial preparations of (non-recombinant) hCG they investigated, hCG from Fujisawa was the most effective, hCG-APL (Wyeth-Ayerst) the next most effective, and pregnyl (Organon) the next most effective in inhibiting HIV infection and replication. A highly purified hCG preparation and recombinant β-hCG were found not to be active in inhibiting HIV infection in vitro. hCG preparations and fractions of hCG preparations can be screened for efficacy in treating or preventing HIV infection by the assays described in Section 5.3 infra or by any method known in the art.

In a specific embodiment, the therapeutic method of the invention is carried out as monotherapy, i.e., as the only agent provided for treatment or prevention of HIV. In another embodiment, the Therapeutic is administered in combination with one or more anti-viral compounds, for example, protease inhibitors (e.g., saquinavir) and/or reverse transcriptase inhibitors (e.g., azidothymidine (AZT), lamioridine (3TC), dideoxyinosine (ddI), dideoxycytidine., (ddC)). The Therapeutic may also be administered in conjunction with chemotherapy (e.g., treatment with adriamycin, bleomycin, vincristine, vinblastine, doxorubicin and/or Taxol) or other therapies known in the art.

In another embodiment, HIV infection is treated or prevented by administration of a Therapeutic of the invention in combination with one or more chemokines. In particular, the Therapeutic is administered with one or more C—C type chemokines, especially one or more from the group RANTES, MIP-1α and MIP-1β.

SOURCES OF hCG AND β-hCG

Native preparations of hCG and β-hCG can be obtained from a variety of sources. Both hCG and β-hCG are commercially available (e.g., Sigma Chemical Company) and hCG is commercially available in a form suitable for therapeutic use in humans (e.g., from Fujisawa, Wyeth-Ayerst Laboratories (APL™), Organon, Inc. (Pregnyl™) and Serono Laboratories, Inc. (Profasim™)). The inventors have discovered that different sources of hCG have variable effects on HIV infection in vitro and in vivo; thus, one aspect of the invention relates to assaying preparations of hCG for efficacy in treatment or prevention of HIV infection. The therapeutic effectiveness of hCG preparations can be tested by the in vitro or in vivo assays described in Section 5.3 onftra or by any method known in the art. It is preferable to test the hCG preparation in an in vitro assay, e.g., for HIV replication or transcription from the HIV-1 LTR or in vivo in an animal model, such as HIV transgenic mice or SIV infected monkeys, before assaying the preparation in humans.

In a specific embodiment, a preparation comprising hCG is used that contains not only the hCG heterodimer but also peptide fragments thereof, e.g., R chain peptides. hCG and β-hCG can also be purified, or preferably partially purified, from any source known to contain hCG, e.g., urine from pregnant women, using conventional techniques well-known in the art, such as affinity chromatography. For example, antibodies prepared against hCG or β-hCG can be used to prepare an affinity chromatography column which can be used to purify the proteins by sell-known techniques (see, e.g., Hudson & May, 1986, *Practical Immunology*, Blackwell Scientific Publications, Oxford, United Kingdom).

The β-hCG-related proteins are preferably prepared by any chemical or enzymatic synthesis method known in the art, as described supra in Section 5.1.

GENE THERAPY

In a specific embodiment, nucleic acids comprising a sequence encoding β-hCG or a β-hCG peptide, are administered for treatment or prevention of HIV infection, by way of gene therapy. Gene therapy refers to therapy performed by the administration of a nucleic acid to a subject. In this embodiment of the invention, the nucleic acid produces its encoded protein that mediates a therapeutic effect by preventing or treating HIV infection. For example, any of the methods for gene therapy available in the art can be used according to the present invention. Exemplary methods are described below.

For general reviews of the methods of gene therapy, see Goldspiel et al., 1993, *Clinical Pharmacy* 12:488–505; Wu and Wu, 1991, *Biotherapy* 3:87–95; *Tolstoshev*, 1993, *Ann. Rev. Pharmacol. Toxicol.* 32:573–596; Mulligan, 1993, *Science* 260:926–932; and Morgan and Anderson, 1993, *Ann. Rev. Biochem.* 62:191–217; May, 1993, *TIBTECH* 11(5):155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the nucleic acid encoding β-hCG or a β-hCG peptide is part of an expression vector that produces β-hCG protein or a β-hCG pepticie in a suitable host. In particular, such a nucleic acid has a.promtoter operably linked to the nucleic acid sequence coding for β-hCG or a β-hCG peptide, said promoter being inducible or constitutive, and, optionally, tissue-specific. In another particular embodiment, a nucleic acid molecule is used in which the β-hCG sequences and any other desired sequences are flanked by regions that promote homologous recombination at a desired site in the genome, thus providing for intrachromosomal expression of β-hCG (Koller and Smithies, 1989, *Proc. Natl. Acad. Sci.* USA 86:8932–8935; Zijistra et al., 1989, *Nature* 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then administered to the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, *J. Biol. Chem.* 262:4429–4432) (which can be used to target cell types specifically expressing the receptors), etc. In a specific embodiment, the nucleic acid can be targeted in vivo for cell specific uptake and expression, by targeting a specific receptor (see, e.g., PCT Publications W092/06180 dated Apr. 16, 1992 (Wu et al.); W092/22635 dated Dec. 23, 1992 (Wilson et al.); W092/20316 dated Nov. 26, 1992 (Findeis et al.); W093/14188 dated Jul. 22, 1993 (Clarke et al.), W093/20221 dated Oct. 14, 1993 (Young)). In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated within host cell DNA for expression, by homologous recombination (Koller and Smithies, 1989, *Proc. Natl. Acad. Sci. USA* 86:8932–8935; Zijlstra et al., 1989, *Nature* 342:435–438).

In a specific embodiment, a viral vector that contains the nucleic acid sequence encoding β-hCG or a β-hCG peptide is used. For example, a retroviral vector can be used (see Miller et al., 1993, *Meth. Enzymol.* 217:581–599). These retroviral vectors have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a patient. More detail about retroviral vectors can be found in Boesen et al., 1994, *Biotherapy* 6:291–302, which describes the use of a retroviral vector to deliver the mdrl gene to hematopoietic stem cells in order to make the stem cells more resistant to chemotherapy. Other references illustrating the use of retroviral vectors in gene therapy are: Clowes et al., 1994, *J. Clin. Invest.* 93:644–651; Kiem et al., 1994, *Blood* 83:1467–1473; Salmons and Gunzberg, 1993, *Human Gene Therapy* 4:129–141; and Grossman and Wilson, 1993, *Curr. Opin. in Genetics and Devel.* 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus- based delivery systems are liver, the central nervous system, endothelial cells, and muscle. Adenoviruses have the advantage of being capable of infecting non-dividing cells. Kozarsky and Wilson, 1993, *Current Opinion in Genetics and Development* 3.499–503 present a review of adenovirus-based gene therapy. Bout et al., 1994, *Human Gene Therapy* 5:3–10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431–434; Rosenfeld et al., 1992, Cell 68:143–155; and Mastrangeli et al., 1993, *J. Clin. Invest.* 91:225–234.

Adeno-associated virus (AAV) has also been proposed for use in gene therapy (Walsh et al., 1993, *Proc. Soc. Exp. Biol. Med.* 204:289–300.) Herpes viruses are other viruses that can also be used.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, *Meth. Enzymol.* 217:599–618; Cohen et al., 1993, *Meth. Enzyrmol.* 217:618–644; Kline, 1985, *Pharmac. Ther.* 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, recombinant blood cells (e.g., hematopoietic stem or progenitor cells) are administered intravenously. Additionally, epithelial cells can be injected, e.g., subcutaneously, or recombinant skin cells (e.g., keratinocytes) may be applied as a skin graft onto the patient. The amount of cells envisioned for use depends on the desired effect, patient state, etc., and can be determined by one skilled in the art.

In an embodiment in which recombinant cells are used in gene therapy, a nucleic acid sequence coding for β-hCG or a β-hCG peptide is introduced into the cells such that it is expressible by the cells or their progeny, and the recombinant cells are then administered in vivo for therapeutic effect. In a specific embodiment, stem or progenitor cells, preferably hematopoietic stem or progenitor cells, are used. Any stem and/or progenitor cells which can be isolated and maintained in vitro can potentially be used in accordance with this embodiment of the present invention.

DEMONSTRATION OF THERAPEUTIC UTILITY

The Therapeutics of the invention are preferably tested in vitro, and then in vivo for the desired therapeutic or prophylactic activity, prior to use in humans. Any in vitro or in vivo assay known in the art to measure H7V infection or production can be used to test the efficacy of a Therapeutic of the invention. By way of example, and not by way of limitation, one could use any of the in vitro or in vivo assays descrIbed infra in Section 6.

In an embodiment of the invention, a method of screening a preparation comprising hCG or an hCG alpha or hCG beta chain or derivative of hCG or said alpha or beta chain, for anti-HIV activity is provided which assay comprises assaying said preparation for the ability to inhibit HIV replication or expression of HIV RNA or protein. In one specific embodiment, the hCG preparation is assayed by a method comprising measuring HIV-1 p24 antigen levels in cultured hematopoietic cells acutely infected with HIV-1, which cells have been contacted with the preparation; and comparing the measured HIV-1 p24 antigen levels in the cells which have been contacted with the hCG preparation with said levels in cells not so contacted with the preparation, wherein a lower level in said contacted cells indicates that the preparation has anti-HIV activity. In another specific embodiment, the hCG preparation is assayed by a method comprising measuring the activity of a reporter gene product expressed from a construct in which the HIV-1 LTR is operably linked to said reporter gene, wherein said construct is present in cells which have been contacted with the preparation; and comparing the measured expression of said reporter gene in the cells which have been contacted with the preparation with said levels in such cells not so contacted, wherein a lower level in said contacted cells indicates that the preparation has anti-HIV activity. In another specific embodiment, the hCG preparation is assayed by a method comprising measuring HIV-1 derived RNA transcripts or HIV-1 antigen levels in HIV-1 transgenic mice administered the preparation; and comparing the measured transcript or antigen levels in the mice which have been administered the preparation with said levels in mice not so administered, wherein a lower level in said administered mice indicates that the preparation has anti-HIV activity. In yet another specific embodiment, the hCG preparation is assayed by a method comprising measuring SIV p27 antigen levels in the peripheral blood mononuclear cells of SIV infected monkeys administered the preparation; and comparing the measured antigen levels in the monkeys which have been exposed to the preparation with said levels in monkeys not so administered, wherein a lower level in said administered monkeys indicates that the preparation has antis HIV activity.

By way of example, to assay a Therapeutic in vitro, one can examine the effect of the Therapeutic on HIV replication in cultured cells. Briefly, cultured hematopoietic cells (e.g., primary PBMCs, isolated macrophages, isolated CD4$^+$ T cells or cultured H9 human T cells) are acutely infected with HIV-1 using titers known in the art to acutely infect cells in vitro, such as $10^5$ TCID$_{50}$/ml. Then, appropriate amounts of the Therapeutic are added to the cell culture media. Cultures are assayed 3 and 10 days after infection for HIV-1 production by measuring levels of p24 antigen using a commercially available ELISA assay. Reduction in p24 antigen levels over levels observed in untreated controls indicates the Therapeutic is effective for treatment of HIV infection.

Additionally, assays for HIV-1 LTR driven transcription are useful for testing the efficacy of Therapeutics of the invention. Specifically, a reporter gene, i.e., a gene the protein or RNA product of which is readily detected, such as, but not limited to, the gene for chloramphenicol acetyltransferase (CAT), is cloned into a DNA plasmid construct such that the transcription of the reporter gene is driven by the HIV-1 LTR promoter. The resulting construct is then introduced by transfection, or any other method known in the art, into a cultured cell line, such as, but not limited to, the human CD4$^+$ T cell line HUT78. After exposure of the transformed cells to the Therapeutic, transcription from the HIV-1 LTR is determined by measurement of CAT activity using techniques which are routine in the art. Reduction in HIV-1 LTR driven transcription demonstrates utility of the Therapeutic for treatment and/or prevention of HIV infection.

Exemplary tests in animal models are described briefly as follows: First, a Therapeutic of the invention is administered to mice transgenic for HIV-1, e.g., mice which have integrated molecular clone pNL4-3 containing 7.4 kb of the HIV-1 proviral genome deleted in the gag and pol genes (Dickie, P., et al., 1991, Virology 185:109–119). Skcin biopsies taken from the mice are tested for HIV-1 gene expression by RT-PCR (reverse transcription-polymerase chain reaction) or for HIV-1 antigen expression, such as expression of gp120 or NEF, by immunostaining. Additionally, the mice are examined for reduction in the cachexia and growth retardation usually observed in HIV-1 transgenic mice (Franks, R.R., et al., 1995, Pediatric Res. 37:56–63).

The efficacy of Therapeutics of the invention can also be determined in SIV infected rhesus monkeys (see Letrin, N. L., and King, N. W., 1990, *J. AIDS* 3:1023–1040), particularly rhesus monkeys infected with $SIV_{mac251}$, which SIV strain induces a syndrome in experimentally infected monkeys which is very similar to human AIDS (Kestler, H., et al., 1990, *Science* 248:1109–1112). Specifically, monkeys can be infected with cell free $SIV_{mac251}$, for example, with virus at a titer of $10^{4.5}$ $TCID_{50}$/ml. Infection is monitored by the appearance of SIV p27 antigen in PBMCs. Utility of the Therapeutic is characterized by normal weight gain, decrease in SIV titer in PBMCs and an increase in $CD4^+$ T cells.

Once the Therapeutic has been tested in vitro, and also preferably in a non-human animal model, the utility of the Therapeutic can be determined in human subjects. The efficacy of treatment with a Therapeutic can be assessed by measurement of various parameters of HIV infection and HIV associated disease. Specifically, the change in viral load can be determined by quantitative assays for plasma HIV-1 RNA using quantitative RT-PCR (Van Gemen, B., et al., 1994, *J. Virol. Methods* 49:157–168; Chen, Y.H., et al., 1992, *AIDS* 6:533–539) or by assays for viral production from isolated PBMCS. Viral production from PBMCs is determined by co-culturing PBMCs from the subject with H9 cells and subsequent measurement of HIV-1 titers using an ELISA assay for p24 antigen levels (Popovic, M., et al., 1984, Science 204:309–321). Another indicator of plasma HIV-1 levels and AIDS progression is the production of inflammatory cytokines such as IL-6, IL-8 and TNF-α; thus, efficacy of the Therapeutic can be assessed by ELISA tests for reduction of serum levels of any or all of these cytokines. Administration of the Therapeutic can also be evaluated by assessing changes in $CD4^+$ T cell levels, body weight, or any other physical condition associated with HIV infection or AIDS or AIDS Related Complex (ARC). Reduction in HIV viral load or production, increase in $CD4^+$ T cell or amelioration of HIV-associated symptoms demonstrates utility of a Therapeutic for administration in treatment/prevention of HIV infection.

THERAPEUTIC COMPOSITIONS AND METHODS OF ADMINISTRATION

The invention provides methods of treatment and prevention by administration to a subject in need of such treatment of a therapeutically or prophylactically effective amount of a Therapeutic of the invention. The subject is preferably an animal, including, but not limited to, animals such as monkeys, cows, pigs, horses, chickens, cats, dogs, etc., and is preferably a mammal, and most preferably human. In a specific embodiment, the subject is a human not afflicted with a cancer which secretes hCG or hCG fragments and, more particularly, not afflicted with KS.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In another embodiment, the Therapeutic can be delivered in a vesicle, in particular a liposome (see Langer, *Science* 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid.) In yet another embodiment, the Therapeutic can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Eeppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115–138 (1984)).

Other controlled release systems are discussed in the review by Langer (*Science* 249:1527–1533 (1990)).

In a specific embodiment where the Therapeutic is a nucleic acid encoding a protein Therapeutic, the nucleic acid can be administered by gene therapy methods as described supra in Section 5.1.2.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. here the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed Smith free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vivo and/or in vitro assays may optionally be employed to help predict optimal dosage ranges. The precise dose to be employed in the formulation will also depend on the route of administration, and the seriousness of the disease or disorder, and should be decided according to the judgment of the practitioner and each patient's circumstances. Doses of, for example but not limited to, at least 15,000 I.U. and up to 45,000 I.U. hCG weekly was effective and well tolerated in humans. Weekly doses of 6,000 I.U. in monkeys and 300–500 I.U. in mice were also effective. Predicted suitable doses of a β-hCG peptide for treatment or prevention of HIV infection include, but are not limited to, 1 to 1000 micrograms per week. Routes of administration of a Therapeutic include, but are not limited to, intramuscularly, subcutaneously or intravenously. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice ref lE.cts approval by the agency of manufacture, use or sale for human administration.

EXAMPLE: EFFECTS OF hCG, β-hCG AND β-hCG PEPTIDE PREPARATIONS ON HIV-1 INFECTION AND DISEASE

As described herein, we have observed beneficial effects of some preparations of human Chorionic Gonadotropin (hCG) against HIV disease including anti-tumor (Kaposi sarcoma, KS), anti-viral, increase in weight and pro-nematopoiesis effects. Our studies document that the same preparations inhibit KS cell growth in vitro and induce apoptosis in a mouse model, inhibit HIV acute infection in vitro, down regulate HIV gene expression in 30 of 30 HIV-1 transgenic mice, inhibit SIV replication in 3 of 3 SIV acutely infected macaque monkeys with no evidence of viral resistance, promote normal hematopoiesis (including CD4$^+$ T cell rise), and reverse the wasting seen in these animals. Examples of these effects were also noted in some HIV-positive patients treated with some hCG preparations. The strength of these effects varied among crude hCG preparations, and highly purified hCG did not retain these activities. However, the anti-KS, anti-viral, and pro-hematopoietic effects were mimicked by 2 synthetic peptides of the beta subunit of hCG which we name satellins Al (amino acid numbers 45–57 (SEQ ID NO:6)) and B (amino acid numbers 109–119 (SEQ ID NO:7)).

EFFECTS OF hCG PREPARATIONS ON HIV-1 TRANSGENIC MICE

HIV-1 transgenic mice were derived from molecular clone pNL 4-3 which contained 7.4 kb of the HIV-1 proviral genome deleted in the ar and pol genes (Dickie et al., 1991, *Virology* 185:109–119). The birth weights of mice homozygous for the HIV-1 transgene are normal, but soon the mice uniformly display severe growth retardation (FIG. 1A), cachexia, and early mortality from expression of HIV-1 genes (env and regulatory genes) which are highly expressed shortly after birth in homozygotes (Franks et al., 1995, *Pediatric Res.* 37:56–63) (FIG. 1B). In addition, these mice develop severe hyperkeratotic skin lesions with marked expression of gpl20 and Nef proteins (Kopp et al., 1993, ATDS Res. Huin. Retroviruses 9:267–275; Vasli et al., 1994, AIDS Res. Hum. Retroviruses 10:1241–1250).

To examine the effects of hCG preparations on HIV transgenic Tg26 mice, 30 mice were administered a commercial preparation of native hCG (APL, Wyeth Ayerst) (300–500 I.U.), and other mice received the partially purified native β-hCG preparation (Sigma) (50–100 μg). For studies involving synthetic peptides, heterozygous transgenic mothers of 6 homozygous transgenic mice were given 10 μg of β-hCG peptide 45–57 (SEQ ID NO:6) where the amino acid residues at positions 47 and 51 are substituted by a branch, where the branches are made up of diaminobutyric acid and proline (branched β-hCG 45–57) (prepared by Dr. N. Ambulos, UMAB) subcutaneously, daily for 10 days. Heterozygous transgenic mothers were treated with the hCG preparation subcutaneously twice weekly. Pups received hCG via the mother's milk.

Blood levels of hCG in the mother and pups were monitored and ranged from 5 IU/ml to over 150 IU/ml over a 96 hour time period (data not shown).

Gene expression was assayed in total RNA extracted from the skin of Tg26 mice with RNAzol. One microliter of RNA was reverse transcribed into CDNA using random hexamer primers and MMTV reverse transcriptase (Life Technologies, MD) in a final volume of 30 μl. One tenth of the cDNA reactions were used for PCR amplification of various HIV gene sequences (env, tat, rev, nef and vif). In addition, glyceraldehyde 3-phosphate dehydrogenase (GAPHD) mRNA was amplified for each sample for normalization. Following 25 cycles of amplification, 10% of the PCR product was resolved by electrophoresis through 2% agarose gels and processed for southern hybridization using FITC-labeled oligonucleotide probes complementary to internal sequences of the amplicons. Detection was performed by chemiluminescence (Amersham).and relative RLNA levels determined by densitometry after normalization with GAPDH MRNA levels.

The hCG (APL) treatments resulted in marked down regulation of HIV-1 gene expression in skin biopsies as determined by the RT-PCR technique (FIG. 1B). The 25 cycles of amplification employed in these experiments readily detected abundantly expressed genes (e.g., env and rev) while the tat gene in treated animals was at low levels, and more readily detected with more cycles of amplification (not shown). Other skin biopsies were examined for HIV viral proteins using mouse monoclonal antibodies against gp120 and Nef by an immunostaining technique. A marked decrease in viral proteins occurred after 2 weeks treatment and no detectable HIV proteins were found after 30 days of hCG treatment (not shown) and the hyperkeratosis of the skin regressed. When the treatment was halted, reappearance of viral protein expression occurred after 2 weeks (not shown).

Associated with the decrease in HIV-i gene expression (FIG. 1B) was a reversal of the growth retardation and cachexia (FIG. 1A). As described immediately below, some synthetic peptides of the β-subunit also reversed the adverse effects of the viral genes in these transgenic animals. In contrast, native α-hCG had no effect on HIV gene expression or the retarded postnatal growth and cachexia (not shown). These findings suggest that one or more HIV gene products are involved in the pathogenic mechanisms leading to growth failure and cachexia in HIV-1 transgenic mice, and that one mechanism of the inhibition of HIV-1 and prevention of the wasting involves blocking viral gene expression.

With respect to the effects of the branched β-hCG peptide of amino acids 45–57 (SEQ ID NO:6), all untreated mice died within 10 days while the treated animals survived, and experienced reversal of growth retardation. Control an.L- mals showed high level of gp120 and nef protein as measured by antibody staining and characteristic hyperkeratosis, while pups treated with the branched peptide showed down regulation of protein expression and normal histology.

EFFECTS OF hCG PREPARATIONS IN SIV INFECTED RHESUS MONKEYS

INHIBITION OF SIV, RECOVERY OF CD4+ T CELLS AND WEIGHT GAIN

Events early in HIV infection are thought to be critical to subsequent AIDS pathogenesis. However, early events in HIV infection in humans are difficult to study, but can be readily investigated in the SIV infected rhesus monkey animal model (Letvin et al., 1990, *J. AIDS* 3:1023–1040). SIV and HIV-1 are similar in many of their biological and physical properties including their genomic structure. In addition, $SIV_{mac}251$, unlike several other SIV isolates, induces a syndrome in experimentally infected rhesus macaques that is similar to human AIDS (Kestler et al., 1990, *Science* 248:1109–1112).

Figure 2A:
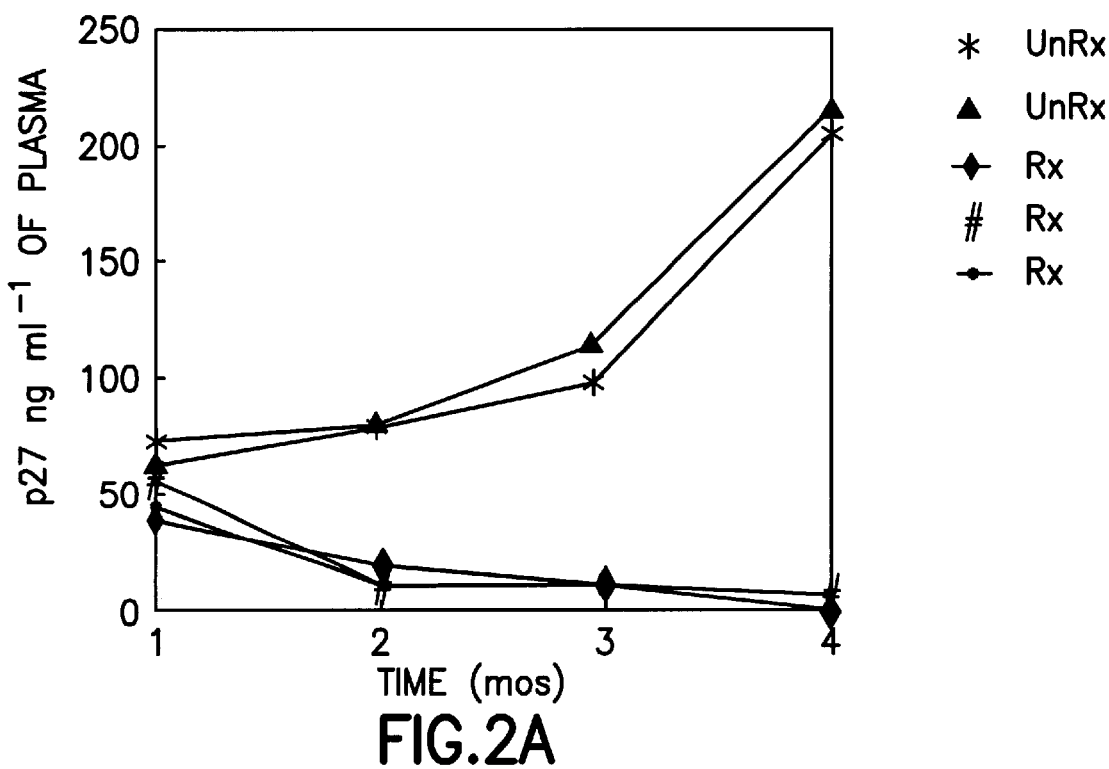
FIGS. 2A–D. Effects of an hCG preparation on indicators of SIV infection in SIV-infected macaques. SIV was given intravenously at a dose of $10^{4.5}$ $TCID_{50}$ per ml. (A) SIV titer was monitored over time in months by quantifying the p27 gag protein (Organon Teknika assay) as nanograms (ng) of p27/ml of plasma from the plasma of the SIV infected macaques. Treated SIV-infected macaques (indicated as Rx) were given hCG APL, 3000 IU, 2x weekly. Plasma levels of p27 gag in these treated monkeys are indicated on the graph by lines with diamonds, number (#) signs or filled circles. Results with the untreated SIV-infected macaques (indicated UnRx) are indicated by the lines with either stars or triangles. (B) CD4+ T cell levels were determined in cells/mm$^3$ in SIV-infected macaques either treated with hCG or untreated over time in months. Results from the SIV-infected monkeys treated with hCG (APL) (Rx) are indicated by lines with diamonds, number (#) signs or filled circles, while results with the untreated monkeys (UnRx) are indicated by lines with stars or triangles. (C) Change in weight in kilograms (kg) was monitored in treated and untreated SIV- infected monkeys over time in months. Weight changes in the SIV-infected monkeys treated with hCG (APL) (Rx) are indicated by lines with diamonds, # signs or filled circles, while results in the untreated monkeys (UnRx) are indicated by lines with stars or triangles. (D) Levels of CD4+ T cells were monitored in normal uninfected monkeys either treated with hCG (APL) or untreated over time in months. CD4+ T cell levels in the untreated monkeys are indicated by lines with sun-like figures or squares, and the results in the treated monkeys are indicated by lines with pentagonal figures or with filled inverted triangles.
Figure 2B:
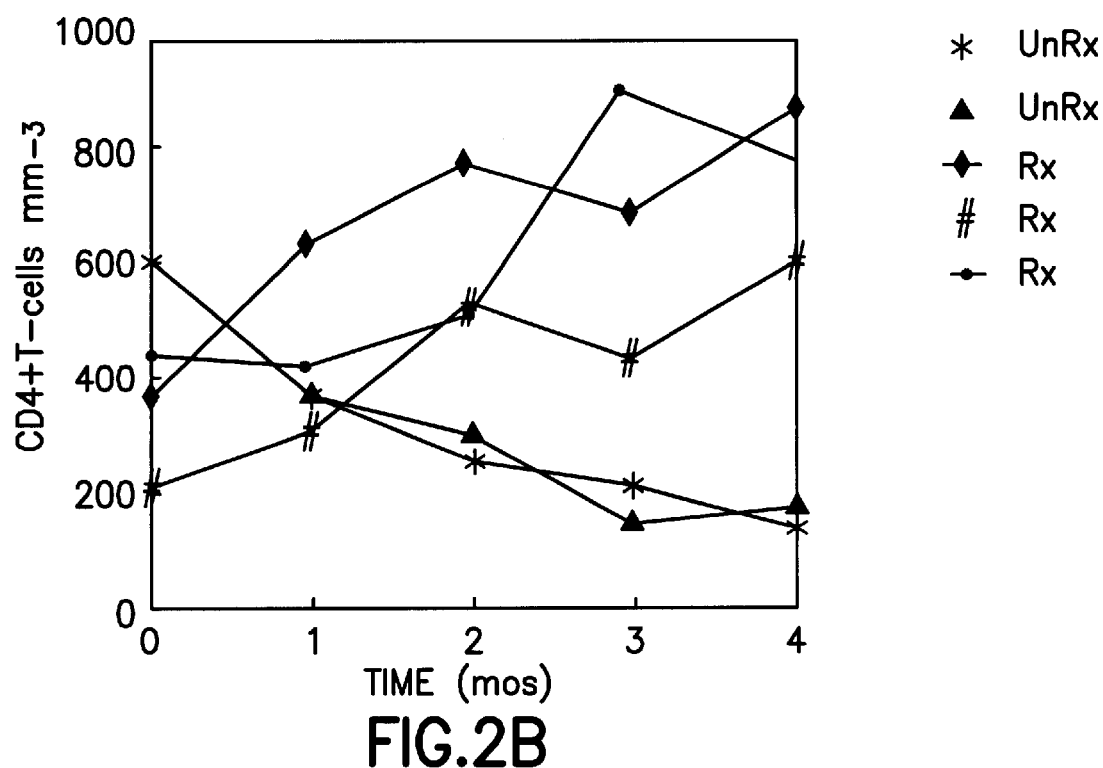
Figure 2C:
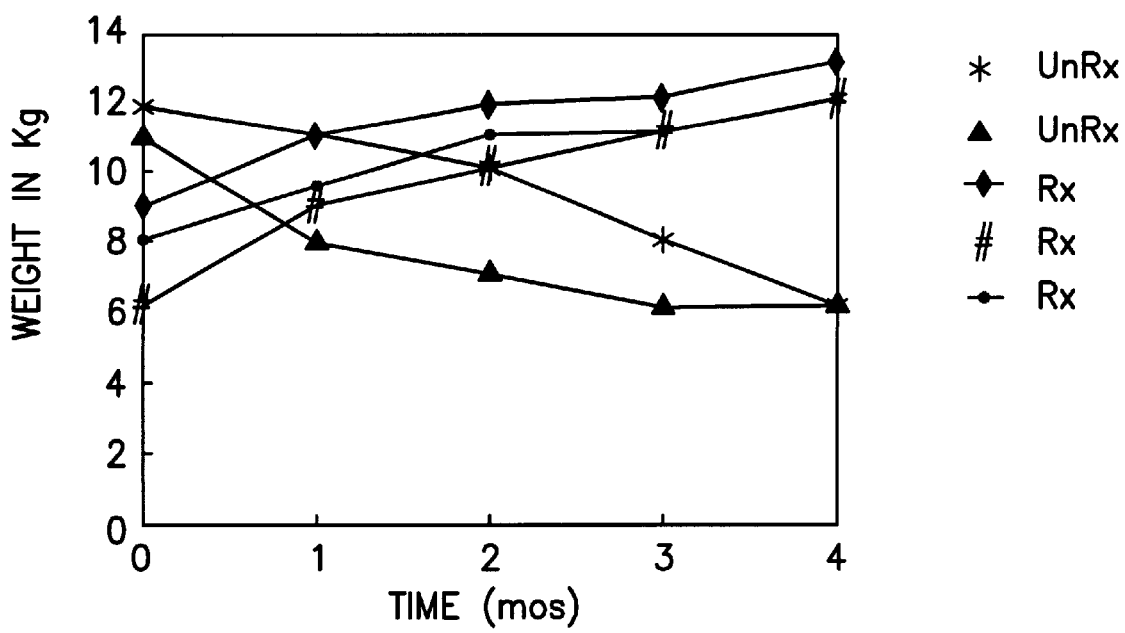

The effect of the same commercially available hCG preparation (APL, Wyeth Ayerst), which had been pre-screened for anti-viral and anti-KS activity, was studied in five adult male rhesus monkeys who were intravenously inoculated with cell free $SIV_{mac251}$ ($10^{4.5}$ $TCID_{50}$/ml). In all animals, SIV p27 was apparent in plasma 14 days after infection, reaching a maximum by about day 20 (not shown). Treatment with systemic injections (3,000 IU, 2 times weekly) of the active commercial preparation of hCG (APL), was initiated 3 weeks after SIV inoculation. Two months post-inoculation, the characteristic increase of SIV p27 antigen (FIG. 2A), reduction of CD4+ T cells (FIG. 2B), and weight loss (FIG. 2C) occurred in 2 of 2 untreated infected monkeys. In contrast, the 3 infected monkeys treated with this hCG preparation showed weight gain characteristic of uninfected animals of this age: 2–4 kg (FIG. 2C), a marked decrease in SIV p27 (FIG. 2A) and an increase in CD4+ T cells to normal levels (FIG. 2B) which were maintained over the 7 months the animals were followed. These results show that this commercially available hCG preparation can control $SIV_{mac251}$ acute infection, increase CD4+ T cells, and promote weight gain in SIV infected rhesus monkeys and that these effects can be maintained. The animals were followed for 7 months, and no evidence of disease or SIV resistance to tne hCG preparation developed.

Figure 2D:
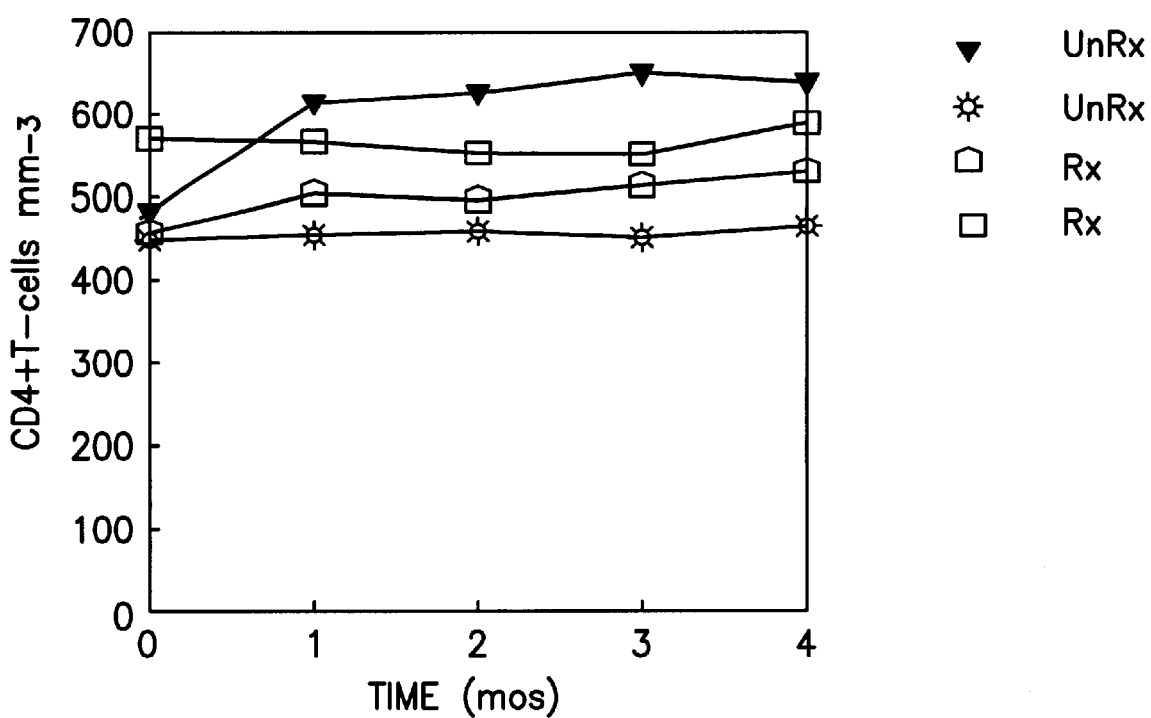

In FIG. 2D, results are shown from 4 uninfected controls: 2 received the hGC; preparation and 2 received the diluent without the hCG. There is a slight increase in the CD4+ T cells in the treated animals (increasing from 460 $mm^3$ to 520 $mm^3$ and from 470 $mm^3$ to 650 $mm^3$) (FIG. 2D). The 2 treated animals also showed a 1 to 2 kg weight gain (not shown).

EARLY STUDIES OF SOME hCG PREPARATIONS IN PATIENTS WITH HIV-1 DISEASE

The incidence of KS is greatly increased in HIV-infected persons (Friedman-Kien et al., 1981, *J. Am. Acad. Dermatol.* 5:468–473). Based on experimental studies of the killing effect of some hCG preparations on KS1 cells, clinical trials with some commercially available preparations of hCG given either intralesionally (Hermans et al., 1995, *Cellular* and *Molecular Biology* 3:357–364; Gill et al., 1996, *NEJM (in press)*; Harris, P. J., 1995, *The Lancet* 346:118–119) or systemically to KS patients have shown that cutaneous KS lesions were reduced via cell killing by apoptosis following intralesional inoculation (Lunardi-Iskandar et al., 1995, *Nature* 375:64–68; Hermans et al., 1995, *Cellular and Molecular Biology* 3:357–364; Gill et al., 1996, *NEJM* (in press)) and induced regression of advanced KS disease treated by systemic delivery.

Early clinical and laboratory data from 46 patients (Table 1) treated on two protocols as well as some treated under IRB sanctioned compassionate use, provide instructive examples of the effects of two hCG preparations, APL (Wyeth Ayerst) and Pregnyl (Organon) in patients at various stages of HIV infection. Early clinical experience with relatively low dose intralesional hCG administration for KS documented partial or complete regression of treated lesions including 3 of the first 4 patients in the initial pilot study in Belgium (Hermans et al.,1995, *Cellular and Molecular Biology* 3:357–364) (patients from Belgian study denoted as "PH" in Table 1) as well as a dose dependent effect between 16% (250 IU) and 83% (2,000 IU) in patients reported from California (Gill et al., 1996, *NEJM* (in press)) (patients from California study denoted as "PG" in Table 1), and other cases showing striking clearance of visceral (lung and gastrointestinal) KS in very advanced disease following systemic therapy with hCC APL or Pregnyl within 1 to 3 months of initiating therapy. In some instances there has been time for long-term evaluation in KS patients and AIDS patients without KS (see below).

Figure 3C:
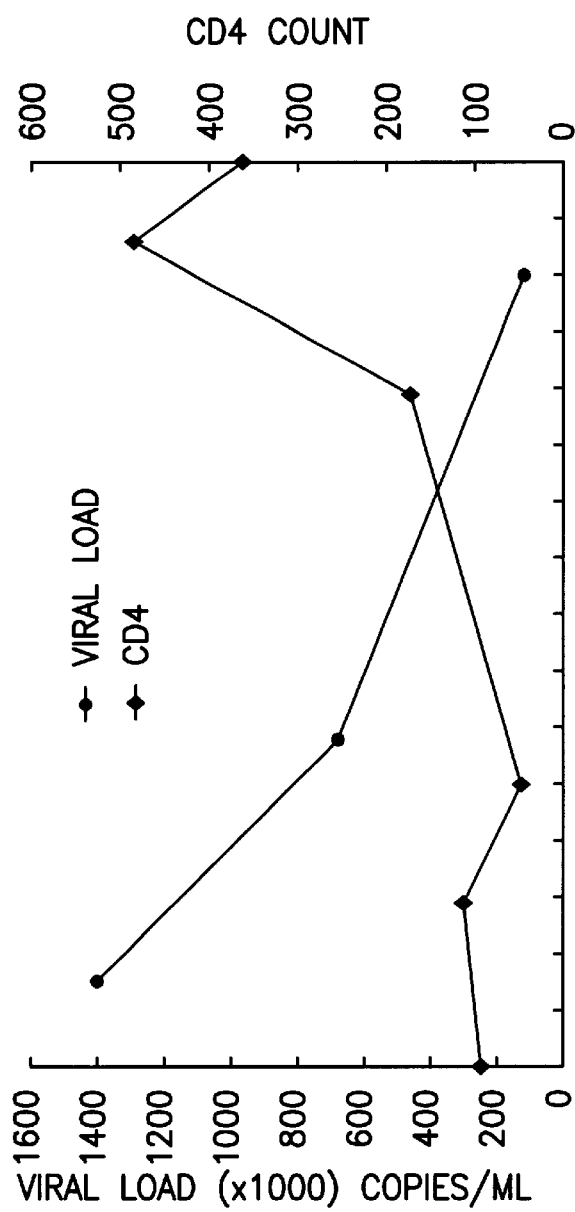
Figure 3D:
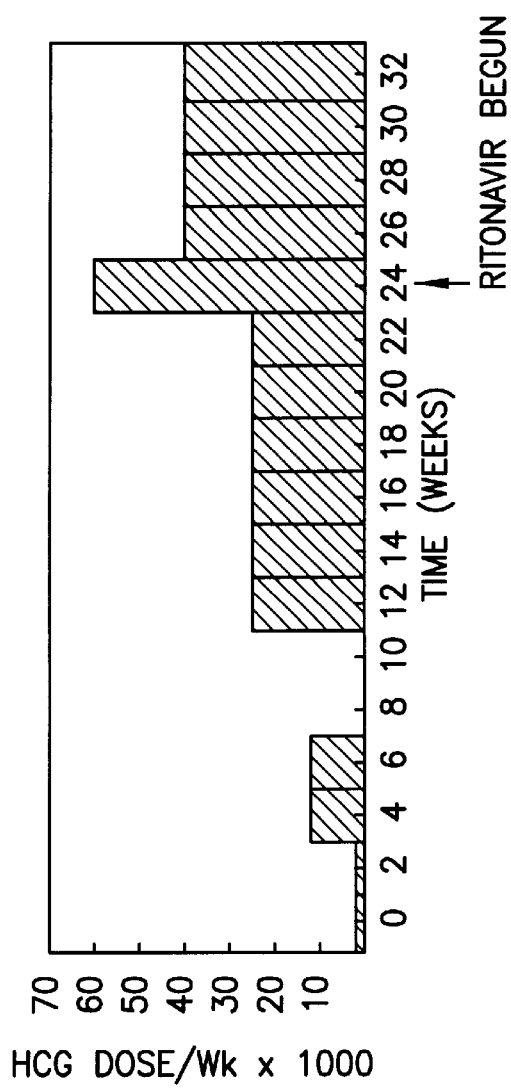

AIDS patients treated with hCG therapy were tested for increases in $CD4^+$ T cell levels (in numbers of cells per $mm^3$) and decrease in viral load by one of the following assays for determining viral load: NASBA (Louache, et al., 1992, *Blood* 180:2991–2999; Geller, et al., 1985, *Archs. Path. Lab. Met.* 109:138–145), which has a lower detection limit of 4,000 copies; Roche Amplicor, with a lower detection limit of 200 copies; RT-PCR, with a lower detection limit of 100 copies; or TCID assay in which the infection of PBMCs in co-culture is determined (Popovic et al., 1984, *Science* 204:309–321). Patients were also examined for weight change (in kilograms) and for changes in Kaposi's sarcoma disease. Illustrative examples of the long-term effect of an hCG preparation in advanced AIDS are described below:

As shown in FIGS. 3A and B, the first patient, PH-VE, with cutaneous KS, who enrolled in the formal trial in Belgium and has now been followed for 80 weeks, experienced an increase in $CD4^+$ T cell levels from 100 $mm^3$ to 160 $mm^3$ and a 1.5 log decrease in viral load from 230,000 copies to 11,000 copies by NASBA assay following relatively low dose intralesional injections and subsequent subcutaneous injections for 6 weeks (FIGS. 3A and B). The patient-has continued therapy over 72 weeks, and viral load, as measured by RT-PCR, has been maintained at a low level (2,500 to 100 viral copies) and $CD4^+$ T cells have remained stable at 204 $mm^3$ at 68 weeks of hCG therapy (FIG. 3A). A recent KSo relapse responded to higher dose hCG treatment (30,000 IU/week). Patient PH-SPBE (FIGS. 3C and D) is illustrative of the synergistic effects of treatment with the hCG preparation followed by antiviral chemotherapy. Following an initial intralesional protocol for 6 weeks, the patient was taken off of hCG therapy for 4 weeks, and then was administered systemic doses of 25,000 IU, followed by 40,000–60,000 IU per week (FIG. 3D). As shown in FIG. 3C, viral load, as measured by NASBA assay, declined from 1,400,000 copies to 700,000 copies and $CD4^+$ T cells stabilized in the mid-100 $mm^3$s. At 22 weeks, Ritonavir therapy was added and subsequent viral load was reduced further and $CD4^+$ T cells rose to over 300 $mm^3$ (FIGS. 3C and D).

Patient PH-OJ (FIGS. 3E and F), who was severely immunosuppressed with $CD4^+$ T cells below 10 $mm^3$, experienced a viral load drop as measured by RT-PCR from 100,000 to 2500 copies after treatment with hCG, but did not experience an increase in $CD4^+$ T cell levels (FIG. 3E). Recently, while on higher doses of hCG (APL), hCG therapy was discontinued because of exacerbation of preexisting cholestasis which required hospitalization.

Of 15 protocol patients from the Belgium trial, an additional 4 had KS responses by ACTGO criteria including several with improved $CD4^+$ T cells and viral load patterns. The non-responders often had very advanced disease and several died during the period of follow-up (Table 1). While viral load and/or $CD4^+$ T cell data were available only for a subset of 29 patients (Table 1), some patients did exhibit increases in $CD4^+$ T cells and some patients also exhibited 1 log or more decreases in viral load (Table 1) without any change in their antiviral therapy.

An additional 10 patients from the Belgium study with advanced disease, some with visceral KS involvement, were treated systemically with higher doses of hCG (15,000 to 30,000 IU) (Table 1). Four have not responded, including 1 who died from opportunistic infection. The remaining 6, however, showed marked responses, including 4 who experienced 75% or more complete regression of visceral KS (Patients PO-DU, PO-GE, PH-JPV, PH-RF), and one (Patient PH-RF) who also demonstrated a decline of viral load from 69,000 copies to less than 4000 copies by NABSA assay (below lower detection limit for the assay).

A recently implemented trial (other "PG" patients in Table 1) employing systemic hCG therapy confirmed a substantial anti-KS effect in 4 of the 5 patients followed for more than 4 months and stabilization of lesions in some patients followed for shorter periods. In one patient (PG-4) on no other antiviral therapy, $CD4^+$ T cell levels rose 10 fold from 47 $mm^3$ to 424 $mm^3$. $CD4^+$ T cell levels in the other patients on anti-virals, including protease inhibitors, were stable or increased. Declines in viral load were noted in several patients, including a 1 log drop in PG-1 (who was on reverse transcriptase inhibitors at enrollment) while stable viral load or demonstrated increases in viral load were noted in other patients (e.g., PG-3 on multiple drugs and PG-15 on no other therapy).

Summarized in Table 1 are the data on 16 patients with paired pre- and post-treatment viral load measurements assayed by either NASBA, Roche Amplicor, or RT-PCR, and 13 patients with paired $CD4^+$ T cell levels and no viral load measurements. In some patients following hCG therapy there were substantial declines in viral load and/or an increase of $CD4^+$ T cells. Since the majority of patients when entered on therapy were also on single or multiple drug anti-viral inhibitors, synergistic effects cannot be ruled out, although some patients showed viral load declines and/or $CD4^+$ T cell increases on hCG alone. Weight gain was recorded in a substantial portion of patients, even some who were in the most advanced stages of HIV infection. Increased appetite and improved sense of well being were also reported. Patient PH-DP with CDC stage Bl-HI77 disease without KS and with no change in preexisting anti-viral therapy experienced a 2 log reduction in viral load as measure in the TCID assay.

It is important to emphasize that there is potential for selection against obtaining positive "hCG" responses in these treated patients. For example, in some patients with advanced disease, only those who responded to "hCG" therapy at lower doses (less than 15,000 IU total weekly) (e.g., PH-VE, PH-MP) were given further "hCG" therapy, including high doses, while treatment was discontinued in those who did not respond at the lower dose (e.g., PH-LFA, PO-LC, P0-CJP, PO-BO, PO-RB Table 1). Thus, the potential for a higher dose effect was not evaluated in those patients who did not respond to the lower doses. For example, in patient PH-GA, stabilization of disease was seen at week 6, but complete regression was not recorded until week 14. Responses of patients to dosages of 30,000 to 45,000 IU, particularly the 4 of 5 patients who exhibited regression of KS disease with at least 4 months of follow-up in the initial data from the systemic protocol (35,000 IU/week) encourage the belief that higher doses of some hCG preparations will lead to more consistent beneficial responses. In view of the positive results in these patients, the lack of significant toxicity of these hCG preparations, coupled with the results in monkeys (FIGS. 2A–C) in which a far higher dose was used (considering body weight), it is evident that "non-responders" studied here merit therapy at higher dose level before concluding that any represent true failure to respond.

TABLE 1

Clinical details of patients treated with an hCG preparation

| Patient ID | Duration of Rx (weeks) | Diagnosis | Weekly Dose hCG/IU | CD4/mm$^3$ PreRX | Rx | Viral Load PreRx | Rx | Weight gain Kg | KS response PR = Partial Regression CR = Complete Regression PD = Progressive Disease |
|---|---|---|---|---|---|---|---|---|---|
| PH-VE[a,b] | 80+ | KS-C | 12,500P 30,000P (M20) | 105 | 160 (M4) | 230,000N 204 (M20) | 11,000 | +6 | PR |
| PH-OJ[b] | 31+ | KS-C | 12,500P | 14 | 3 (M4) | 100,000R | 2,500R | +3 | PR |
| PH-GF | 18+ | KS-C | 12,500P | 3 | 35 (M2) | 1,100,000N | 150,000N | +2 | PR |
| PH-SPBE[b] | 29+ | KS-C | 25,000PA | 48 | 174 (M3) | 1,400,000N | 770,000 | +1 | PR |
| PH-RF[b] | 12+ | KS-V | 15,000P | 0 | 17 (M3) | 69,000N | <4000N | +1 | PR |
| PH-DP[b] | 8+ | No KS | 30,000P | 517 | NA | 100T | 1T (1 mo) | ND | NA |
| PH-JPV | 8+ | KS-V | 15,000P | <50 | NA | NA | NA | NA | CR |
| PH-LE | 12+* | KS-VC | 30,000P | <5 | <5 (M1) | NA | NA | NA | Stable |
| PH-MP | 24+* | KS-C | 30,000P | 360 | 505 (M3) | NA | NA | +3 | CR |
| PH-GRX[b] | 17+* | KS-C | 12,500P | 97 | 89 (M2) | NA | NA | −3 (diet) | PR |
| PH-GA | 12+ | KS-C | 15,000 | 10 | NA | 2,500 R | 500 R | 0 | CR |
| PH-SP[b] | 8+* | KS-VC | 30,000P | 6 | 5 (M1) | NA | NA | 0 | PD |
| PO-FY[b] | 6+* | KS-C | 12,500P | 180 | 202 (M2) | NA | NA | +1.5 | PD |
| PO-GE[b] | 48+* | KS-VC | 15,000P | 10 | 10 (M4) | NA | NA | 0 | CR |
| PO-DU[b] | 37+ | KS-VC | 12,500P | 5 | 10 (M2) | 420,000N | 300,000 | +2 | Stable |
| PO-LC[b] | 12+ | KS-VC | 12,500P | 70 | 72 (M3) | NA | NA | +1.5 | PD |
| PO-CJP[b] | 6+ | KS-C | 12,500P | 14 | 14 (M1.5) | NA | NA | +1 | PD |
| PO-BO[b] | 6+ | KS-C | 12,500P | 12 | 12 (M1.5) | NA | NA | +1.5 | PD (Died) |
| PO-RB[b] | 4+ | KS-VC | 12,500P | 50 | 35 (1M) | NA | NA | +1 | PD (Died) |
| PG-1[b] | 16+ | KS-C | 35,000A | 63 | 170 (M4) | 75,000A | 1,700A | −0.9 | PD |
| PG-3[b,c] | 16+ | KS-C | 35,000A | 37 | 48 (M4) | 52,000A | 40,000A | +1.8 | CR |
| PG-4 | 16+ | KS-C | 35,000A | 47 | 424 (M4) | 80,900A | 55,000A | +1.4 | Stable |
| PG-6[b,c] | 12+ | KS-C | 35,000A | 29 | 21 (M3) | 62,500A | 98,000A | +3.2 | Stable |
| PG-7 | 10+ | KS-C | 30,000A | 108 | 213 | NA | NA | +4.5 | PR |
| PG-8 | 12 | KS-C | 30,000A | 787 | 678 | 60,760A | 22,313A | +2.3 | PD |
| PG-9 | 11+ | KS-C | 30,000A | 123 | 218 | NA | NA | −5.0 | Stable |
| PG-10[b] | 12 | KS-C | 30,000A | 82 | 86 | 25,364A | 6,777A | +2.3 | Stable |
| PG-11[b] | 4.5 | KS-C | 30,000A | 218 | 361 | 661A | 200A | +5.4 | Stable |
| PG-12 | 19+ | KS-C | 30,000A | 22 | 46 | NA | NA | +10.0 | PR |
| PG-15 | 8 | KS-C | 70,000A | 388 | 483 | 6,162A | 22,510A | +1.8 | PD |

*Only patients with CD4$^+$ T-cell and/or viral load data are included. Patients who began protease inhibitors at the beginning or during hCG therapy or who did not comply with hCG therapy (PG-17) are excluded.
preRx = before treatment with hCG;
Rx = post treatment with hCG.
[a]Data on PH-VE are presented in the text reporting stabilization of CD4 levels over 20 months of hCG monotherapy and persistently low viral load by RT-PCR (range 500 to 12,500) with escalating doses of hCG from 15,000 IU (52 weeks) to 30,000 IU per week (Pregnyl) recently which resulted in regression of recurrent cutaneous KS.
[b]Patient was on nucleoside/non-nucleoside reverse transcriptase inhibitors when hCG treatment began;
[c]Patient was on protease inhibitors when hCG started.
The following indicate response of Kaposi's Sarcoma to treatment:
PD indicates progressive disease; CR indicates complete response; and PR = Partial response. NA represents data not available.
The hCG commercial preparations administered are indicated by P for Pregnyl and A for APL. M represents month from enrollment on protocol. Viral load techniques used are indicated by R for RT-PCR; N for NASBA; T for TCID; A for Roche Amplicor.
Under the diagnosis column, KS represents Kaposi sarcoma; KS-V represents KS with visceral involvement; KS-C represents KS with cutaneous lesions only; KS-VC represents KS with both visceral and cutaneous involvement.

Patient Information

A total of 46 patients were available for analysis of whom 30 are included in Table 1 because serial viral load data and/or CD4$^+$ T cell counts were recorded. Twenty-eight patients were treated in Belgium, either on a protocol to investigate intralesional and systemic treatment of cutaneous KS (n=15), or in the pre-clinical phase of that protocol (n=3), or on compassionate use for systemic KS or HIV infection (n=10). The protocol involved intralesional administration of 500 IU hCG (Pregnyl) to 4 lesions for 2 weeks, followed by subcutaneous administration of 2,500 IU hCG (Pregnyl) 5 days per week for 4 to 6 weeks. Additional systemic intramuscular or subcutaneous hCG treatment with either Pregnyl, APL, or Steris (one patient) was provided as ongoing therapy in some patients or as part of compassionate use protocols.

A total of 18 patients were treated in California with at least 1 month of follow-up as part of an ongoing protocol to evaluate systemic hCG therapy for cutaneous KS. These patients received either 5000 IU of APL subcutaneously 7 days per week, 10,000 IU subcutaneously 3 times per week, or 10,000 IU subcutaneously 7 days per week. Five of the systemic cases are not shown because of absent baseline viral load measurements. Five patients with serial viral load measurements started protease inhibitors during the course of hCG therapy and their viral load data is not listed: PG2, who had viral load measurement of 10,496 copies before starting the hCG therapy and a last measurement of 15,542 copies (Roche Amplicor test), started Norvir after hCG; PG5, for whom there was no viral load data started Norvir after hCG; PG-16, had a viral load measurement of 47,931 copies before starting hCG therapy and a last measurement of 370 copies, started Ritonavir after hCG; PG-18, with a viral load of 3673 copies before hCG therapy and a last viral load measurement of 1742 copies, started Crixivan after hCG; PH-SPBE had a viral load of 120,000 copies (NASBA test) compared to the value of 770,000 copies before Ritonavir was added to ongoing hCG treatment; and PH-JPV, had a viral load of 500,000 copies (Roche Amplicor test) before starting hCG therapy and by week 4 of hCG alone, had a viral load of 4,900,000 copies and exhibited undetectable viral load following indinavir (Crixivan) which was added after hCG induced pulmonary response.

Overall 28 patients were on pre-existing, anti-viral therapy (RT inhibitors), 11 were on no anti-virals and 7 were missing information. One patient, PH-RF, was on 3TC therapy before hCG therapy, and despite poor compliance, had an hCG response for visceral KS and viral load, which declined to undetectable on hCG alone.

Thirty-six patients survived the study, 7 (PH-LFA, PH-DD, PH-PJ, PO-BO, PO-RB, PH-JJ, PH-MH) died either from opportunistic infections or multiple organ failure. The vital status of 1 patient is unknown. Two patients, PH-DD and PH-OJ discontinued hCG treatment because of cholestasis. PH-DD was on concomitant anti-mycobacterial therapy which was felt to be a contributing factor. PH-OJ had preexisting cholestasis. When heG was restarted recently, cholestasis was exacerbated with a marked increase in alkaline phosphatase and rise in bilirubin which required hospitalization. These values declined by 2-fold following discontinuation of hCG. These cases raise the possibility that liver toxicity may be a rare complication of hCG therapy. Among the patients not listed in Table 1, 2 (PG2 and PG5) are on systemic hCG and have exhibited a KS response; 7 (PH-JJ, PH-MH, PH-LG, PH-JPV, PG-16, PG-18) had partial responses; 2 (PO-SC, and PH-LFA) did not respond to hCG or their disease progressed on therapy; 2 (PG-13 and PG-14) are currently in follow-up, but not evaluable; and 4 (PH-PJ, PH-DP, PH-GL, PG17) could not be evaluated or were lost to follow-up. PO-DU experienced stabilization of pulmonary disease and recently developed 2 new cutaneous lesions which responded to radiation therapy without any change in his pulmonary KS. PO-GE experienced complete response to cutaneous and pulmonary KS on hCG alone, PH-RF with gastric KS experienced a marked decline in viral load and a 75% decline and subsequent stabilization of pulmonary KS on hCG, and PH-JPV with pulmonary and gastric KS dramatically improved his pulmonary function test after one month of hCG alone.

EFFECTS OF hCG PREPARATIONS ON HIV-1 INFECTION IN VITRO

Primary PBMCs, isolated macrophages and CD4+ T cells from peripheral blood, and the H9 human T cell line were acutely or chronically infected with 8 different HIV-1 strains: 4 cell line adapted viruses, namely the macrophage tropic Ba-L strain (Gartner et al., 1986, Science 233:215–219) and the CD4+ T cell tropic MN, RF, and IIIB strains ($10^5$ $TCID_{50}$/ml) (Popovic et al., 1984, Science 204:309–321; Gallo et al., 1984, Science 224:500–503); 2 isolates, Jul083 and G3, from Nigerian AIDS patients passed once in a CD4+ T cell line (Sub-T1); and 2 primary ("clinical") isolates from patients with AIDS from Trinidad which were never passed in any cell lines and were used at a titer of $7.5 \times 10^4 TCID_{50}$/ml. In all experiments HIV-1 ($10^5 TCID_{50}$/ml was added to the cells ($10^6$ cells/ml) for a 2 hour incubation after which the virus infected cells were washed with 10 ml phosphate buffered PBS×3 to eliminate extracellular virus. The test inhibitor was then added and incubation carried out for 9 to 10 days with serial sampling. Cultures were assayed for p24 antigen on days 3 to 10. The inhibition of HIV production by the active preparations was not due to cell toxicity since at the concentrations used there was little or no effect on $^3$HTdR incorporation, or cell viability as assessed by cell counts and MTT assays (data not shown). Sequences of the peptides are as follows:

Satellin Al peptide: Amino Acids 45–57, linear: Leu Gln Gly Val Leu Pro Ala Leu Pro Gln Val Val Cys (SEQ ID NO:6).

Satellin Al branched peptide: Amino Acids 45–57, branched linear: Leu Gln Dab(Pro) Val Leu Pro Dab(Pro) Leu Pro Gln Val Val Cys, where "Dab" represents diaminobutyric acid, and Dab(Pro) indicates a proline peptide-bonded to the amino side chain of Dab.

Satellin A2 peptide: Amino Acids 45–57 with a cysteine residue added to the N-terminus, circularized via a disulfide bond between the cysteine residues: Cys Leu Gln Gly Val Leu Pro Ala Leu Pro Gln Val Val Cys (SEQ ID NO:26).

Satellin B peptide: Amino Acids 109–119, linear: Thr Cys Asp Asp Pro Arg Phe Gln Asp Ser Ser (SEQ ID NO:7).

Figure 4A:
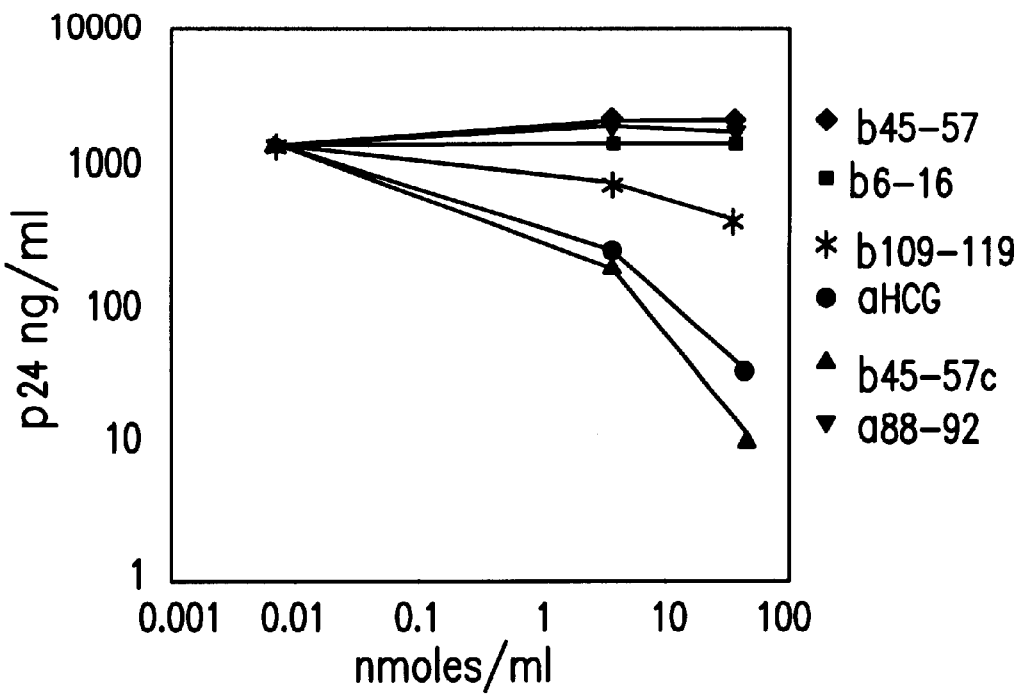
FIGS. 4A–D. Effects of hCG preparations and peptides on HIV replication in vitro. (A and B) These graphs depict the concentration dependence of inhibition of HIV-1 IIIB infection of CD4+ T cells or total PBMCs from peripheral blood of normal donors (infection is expressed in nanograms (ng) of p24/ml plasma) as a function of nmol per ml α-hCG subunit, β-hCG peptide or α-hCG peptide over a concentration of 0.05 to 50 mmol/ml. Graphs present data on infection of (A) CD4+ T cells infected by HIV-1 IIIB and (B)
Figure 4B:
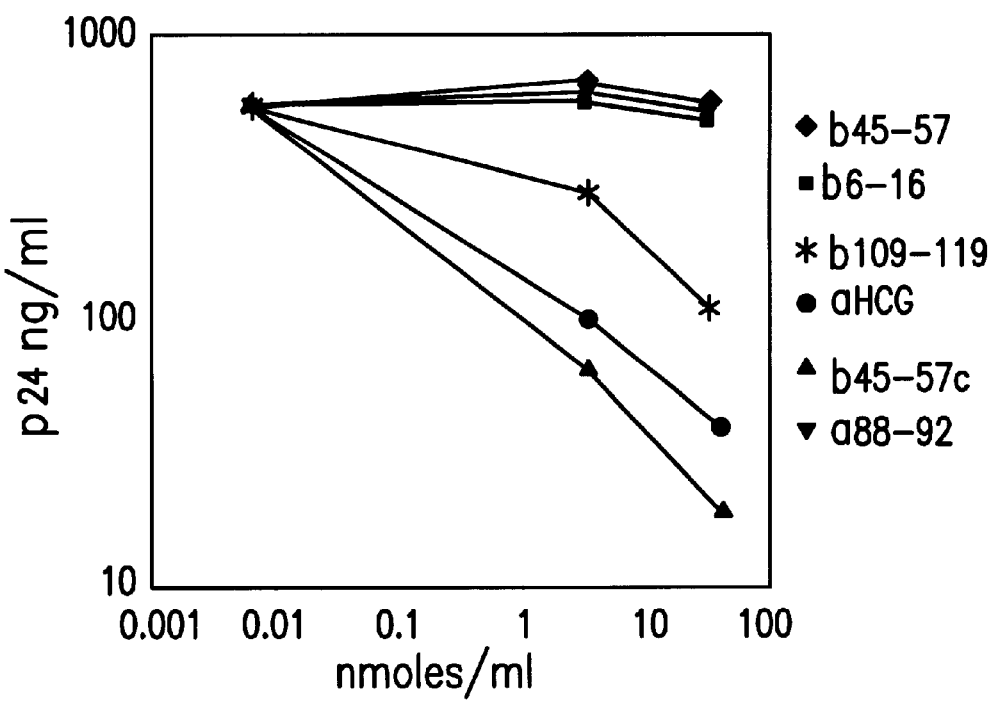
Figure 4C:
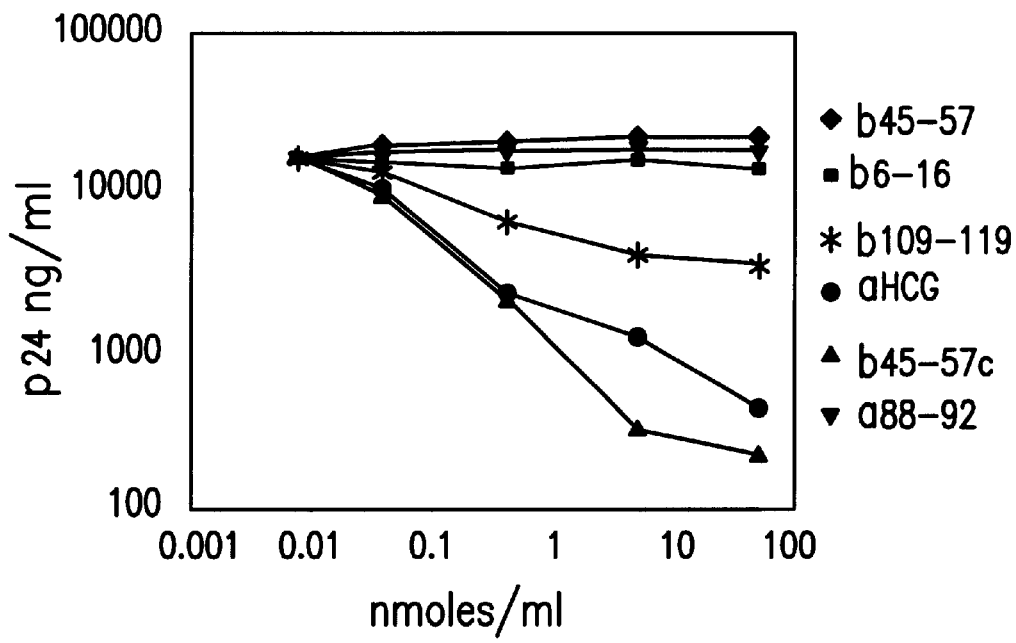

There were no significant differences in the results with different strains of HIV-1 (not shown). For illustrative purposes, data are presented with HIV-1 IIIB infected isolated CD4+ T cells (FIG. 4A), IIIB infected PBMCs (FIG. 4B) and HIV-1 Ba-L infected isolated macrophages (FIGS. 4C and D). As shown in FIGS. 4A–D, the inhibitory effects of the peptides or hCG preparations were approximately the same for macrophage tropic (FIGS. 4C and D) or T cell tropic strains (FIGS. 4A and B). Infection with primary isolates showed similar inhibition (data not shown). In contrast to the potent inhibition of acute HIV-1 infection in vitro by the active hCG preparations or synthetic peptides (see Section 7.6 below), there was slight or moderate inhibition (20–40%) of virus production (HIV-1 IIIB) from chronically infected CD4+ T cell lines (not shown). All target cells had similar patterns, but with expected variation in p24 antigen expression (FIGS. 4A–D).

Figure 4D:
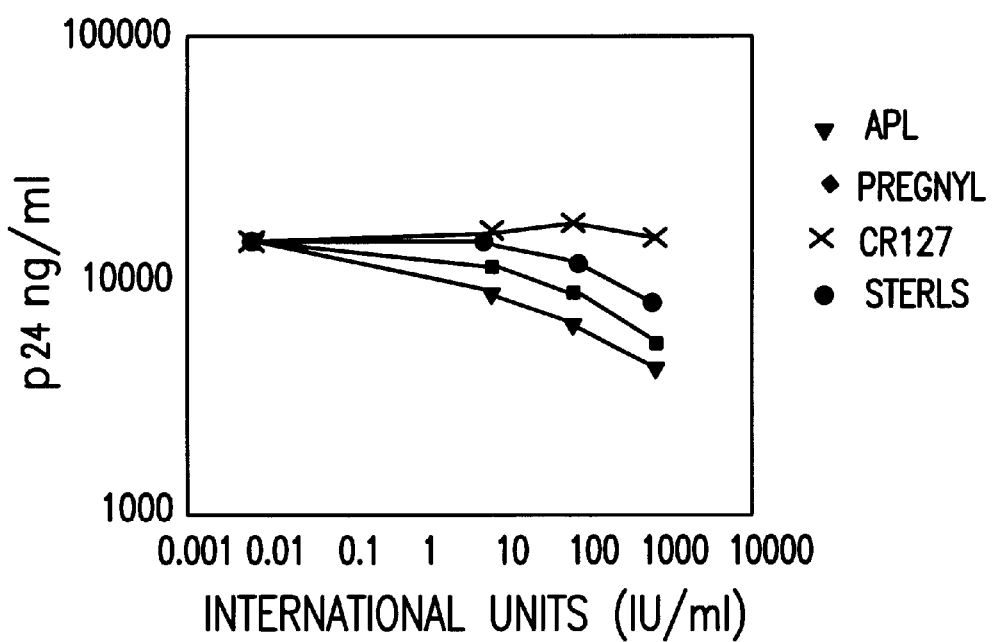

As already noted, we found significant variation in the activity of various commercial preparations of native hCG to kill KS tumor cells (Lunardi-Iskandar et al., 1995, Nature 375:64–68; Hermans et al., 1995, Cellular and Molecular Biology 3:357–364; Gill et al., 1996, NEJM (in press)). As shown in FIG. 4D, there is similar variation in the anti-HIV activities of these preparations. For example, for the native heterodimer preparations, the most active preparation was usually hCG APL (Wyeth Ayerst) followed by hCG Pregnyl (Organon). Therefore, hCG APL was used in all laboratory studies whenever the native heterodimer was required.

Employing hCG APL, there is a dose dependent inhibition of HIV-1 replication (FIG. 4A). Surprisingly, there was little or no inhibition with the highly purified native hCG heterodimer (generously supplied by the National Hormone and Pituitary Program and Center for Population Research, NIH) CRIXY17B (data not shown) and CR127 (FIGS. 4C and D) nor with purified recombinant α- or β-chains. However, commercially available hCG (APL, Wyeth Ayerst) and partially purified native β-hCG (NβhCG) (dissociated from hCG, Sigma) was active while native α-hCG was not (FIGS. 4A–D).

EFFECT OF hCG PREPARATIONS ON HIV-1 TRANSCRIPTION

To further elucidate the anti-HIV effects of crude hCG preparations, we studied the effect of hCG-APL on a HIV-1 LTR driven expression of a reporter gene, chloramphenicol acetyltransferase (CAT) (FIGS. 5A–C). The T-lymphocyte call line HUT 78 was transiently transfected Pith the HIV-LTR construct 174WTIICAT by electroporation. $1 \times 10^7$ cells were resuspended in 0.4 ml RPMI 1640 medium supplemented with 10% fetal calf serum (FCS), and 20 μg of the test plasmid with 2 μg of the Tat expression vector pDEX/Tat were introduced into the cells by a pulse of 250 V and 950 μF at 4° C. using a Biorad GenePulser II apparatus. (Plasmids were the generous gift of Dr. Richard Gaynor, University of Texas Southwestern Medical Center.) Cells were then divided into three aliquots and maintained at 37° C., 5% $CO_2$ for 40 hours in the presence of drug, or an equal volume of diluent. Transiently transfected cells were harvested, lysed and a standard amount (4 μg) of heat-treated extract was incubated in the presence of 0.6 mM acetyl coenzyme A and 0.1 μCi[$^{14}$C] chloramphenicol in 0.25 mM Tris, pH 7.9 at 37° C. for 1 h. The amount of acetylated [$^{14}$C] chloramphenicol converted to acetyl [$^{14}$C] chloramphenicol was determined following thin layer chromatography in chloroform: methanol 95:5 (v/v) to fractionate the reaction mixture. Results were quantified by phosphorimage analysis on a Molecular Dynamics Phosphor Imager 445 SI. For each assay the amount of acetylated chloramphenicol was determined as a fraction of total [$1^4$C] in the sample to drive the activity of the CAT enzyme.

The expression of CAT driven by the HIV-1 LTR was inhibited in a dose-dependent manner such that 78% of normal transcription from the LTR was detected in cells treated with 100 IU/ml hCG (APL) and 36% of normal transcription was detected in cells treated with 500 IU/ml hCG (APL) (FIG. 5A). hCG had no effect on transcription of the SV-40 driven CAT construct (FIG. 5B). The hCG preparation also.had no inhibitory or cytotoxic effect on these cells even after 40-hour incubation with 500 IU/mi hCG (FIG. 5C) as we have previously shown (Lunardi-Iskandar, Y., et al., 1995, *Nature* 375:64–68). Results from constructs with point mutations in the enhancer (NFkB), SP-1 and TAR regions showed essentially the same response to hCG; therefore, none of these important regulatory elements was demonstrated to be necessary for the response to hCG (not shown). These results are in accord with the transgenic mice results and indicate that at least part of the inhibitory effect of these hCG preparations is on transcription of the HIV-1 provirus. However, the far greater inhibition of acute infection over chronically infected cells suggests that other important mechanisms are operative.

EFFECTS OF β-hCG PEPTIDES ON HIV-1 INFECTION

The variation in the viral inhibitory effects of various native hCG preparations and the observation that the native, partially purified β subunit, but not the recombinant β-chain (not shown) was active (native α-chain and recombinant α-chain were both inactive) suggested two possibilities: (1) The active fraction is not hCG but a co-purifying contaminant which further co-purifies with β-hCG; (2) The active fraction is the 0 subunit or a breakdown product of this molecule, and its variable activity among different commercial preparations is due to differences in their urinary source (e.g., β-hCG is higher in the earliest days of pregnancy and different companies may use urine from different stages of pregnancy), their methods of preparation, or both. Identification of an active fraction would provide more information on the molecular mechanism of these effects, e.g., insights into the minimum structure needed, whether classical hCG receptors are involved, and whether the various biological effects are all the effect of one active segment of hCG or due to different structures.

Since it is known that hCG has proteolytic products hich may co-purify with the heterodimer or its β-chain, studies were initiated to define the active moiety in the hCG (APL) preparation by reverse phase HPLC fractionation which showed the highly crude nature of this material, but none of the several peaks were active in any of the lin vitro bioassays [anti-KS and anti-HIV (not shown)].

As an alternative approach, a series of α- and β-subunits and various synthetic peptides were compared to the active preparations of the native heterodimer (FIGS. 4A–D). Peptides of the α- and β-subunits (0.05 to 50 nmoles/ml), and native a and also various crude preparations of the native hCG heterodimer (0.01 to 1,000 IU) and the native β-hCG subunit (100 to 1,000 μg) were tested for effects on HIV-1 replication in acutely infected cells (FIGS. 4A–D). HIV-1 infected cells were treated with the above preparations and the virus was measured.

The effect of β-hCG synthetic peptides β-hCG 45–57 (SEQ ID NO:6) (satellin Al) and circularized β-hCG 45–57 (SEQ ID NO:6), with the addition of a cysteine at the amino terminus (satellin A2) were the most active. The only other active fraction was peptide β-hCG 109–119 (satellin B) (SEQ ID NO:7). These peptides inhibited HIV infection in a dose dependent fashion (FIGS. 4A, B and C) and had comparable activity with various cell systems (FIGS. 4A, B and C) and against various viral strains (not shown) including primary field isolates. Native α-hCG, the α-hCG peptide of 88–92 and the β-hCG peptides 6–16 and 74–95 had little or no effect (FIGS. 4A, B and C). When the amino acids in the region of the active peptide 45–57 (SEQ ID NO:6) were scrambled, the resulting peptide also had no activity. A series of other β-peptides were also inactive (not shown).

EFFECTS OF β-hCG PEPTIDES ON KAPOSI SARCOMA CELLS

Neoplastic KS tumor cells with a characteristic chromosomal abnormality have been reported (Delli-Bovi et al., 1986, *Cancer Res.* 46:6333–6338; Siegal, et al., 1990, *Cancer* 65:492–498; Popescu et al., 1995, *JNCI* 88:450–454) and provide a model system for studying the in vitro effects of hCG. In our prior studies employing immune deficient mice injected with KS tumor cells, some commercial preparations of native hCG killed KS tumor cells in vivo by inducing apoptosis and inhibiting angiogenesis. In vitro tumor cell colonies are also suppressed in clonogenic assays by the hCG preparations (Lunardi-Iskandar et al., 1995, *Nature* 375:64–68; Nakamura et al., 1988, *Science* 242:426–430 Ensoli et al., 1989, *Science* 243:223–226; Salahuddin et. al., 1988, *Science* 242:430–433; Masood, et al., 1984, *AIDS Res. Hum. Retroviruses* 10:969–976). In the current study, experiments were performed to investigate whether the anti-viral effect of the active peptides (FIGS. 4A-D) correlated with the anti-KS effect of native hCG both in vitro in clonogenic assays on cultured KS Y-1 cells and ir vivo in KS tumors induced in nude mice.

Briefly, the KS Y-1 cells were obtained from mononuclear cells isolated from pleural effusion of an AIDS patient with KS involving the lungs. After the depletion of T lymphocytes, monocytes/macrophages and fibroblasts by the cytotoxicity method, using monoclonal antibodies against CD2, CD3, CD4, CD8, CD10 and CD14 membrane antigens and baby rabbit complement, the cells were cultured in the absence of exogenous growth factors to select for transformed cells. Immunological characterization of the KS Y-1 cells showed that CD34, CD31 and endoglin were expressed. Clonogenic assays were performed by seeding the KS Y-1 or KS-SLK cells in methylcellulose (0.8%, v/v), incubating the cells for 10 days in the presence or absence of the hCG, β-hCG or β-hCG peptide preparation and then counting the number of well-formed colonies of triplicate wells formed after seeding with $5 \times 10^4$ cells.

As shown in FIG. 6A, the peptides (50 nmoles/ml) with the strongest anti-viral effects (peptides of amino acids 45–57 (SEQ ID NO:6), cyclic 44–57, with cysteine substituted at position 44 (SEQ ID NO:26) and 109–119 (SEQ ID NO:7)) also had the strongest anti-tumor effects (anti-KS) on 2 KS neoplastic cell lines. It is notable that the purified hCG heterodimer (CR127 2 nmoles/ml) was again inactive as it was in the HIV assays. There was no anti-KS effect with the pure α- and β-chains and the following peptides were tested and showed little or no inhibition in clonogenic assays: α-hCG peptide 88–92; and the β-hCG peptides of amino acids 6–16, 7–40, 34–49, 38–57, 57–93, 74–95, 100–110, 123–145, and 134–144. Scrambled β-hCG peptides 45–57 and 109–119 showed little inhibition. Peptides were obtained from Bachem, Calif., Rockville Peptides Inc or generously provided by Dr. N. Ambulos of the University of Maryland (Medical Center) at Baltimore.

The effects of the peptides on KS tumor cells were also evaluated in vivo in the mouse model. To induce KS tumors in the mice, $1 \times 10^6$/ml KS Y-1 cells in 50 μl PBS or saline were injected subcutaneously into immunodeficient mice (beige-XID-BNX mice). After one week, tumors ranged in size from 2×3 mm to 3×5 mm. Methods for detection of apoptosis (from tissue biopsies) were used, as described in Lunardi-Iskandar, Y. et al.(1995, Nature 375:64–68). Briefly, the samples were stained in situ for the presence of cells with DNA fragmentation. Tissue slides from formalin-fixed tumors were treated with terminal deoxynucleotide transferase for extension of DNA ends (hydroxyl 3') and incorporation of digoxigenin-11-dUTP according to the manufacturer's instructions (Oncor, Gaithersburg Md.). Antidigoxigenin antibody conjugated with the enzyme peroxidase allowed detection of apoptotic cells that stain brown whereas viable cells stain blue.

Figure 6B:
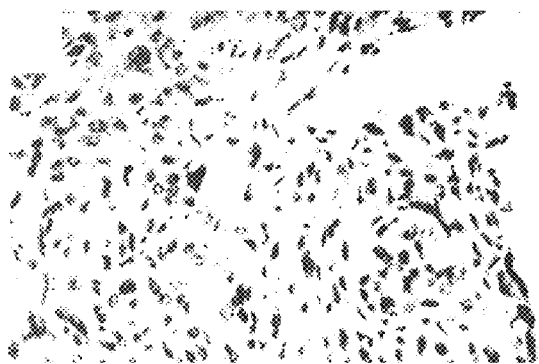
Figure 6C:
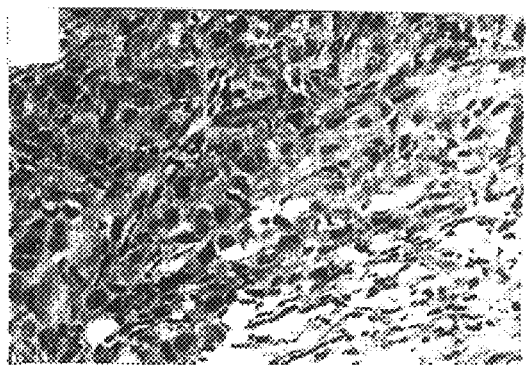
Figure 6D:
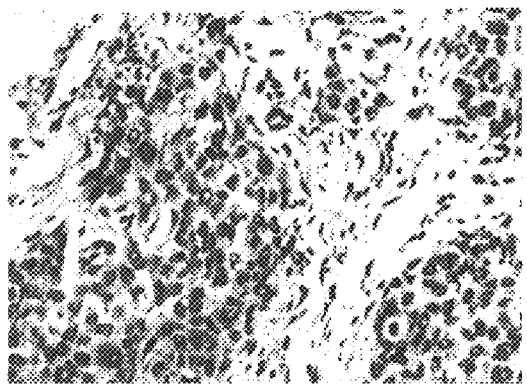
Figure 6E:
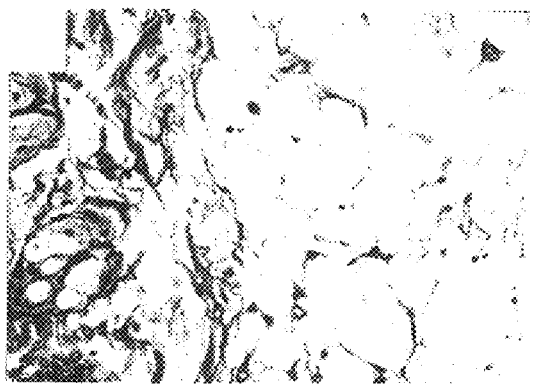

Shown in FIGS. 6B–E are representative examples of the effects of hCG and the β-hCG peptides on KS Y-1 tumors in mice. One week after injection with the tumor cells, the mice were treated with crude hCG (APL, Wyeth Ayerst) or with β-chain peptides 45–57 (SEQ ID NO:6) and cyclic 44–57 [Cys44] (SEQ ID NO:26). FIGS. 6B–E show hematoxylin and eosin staining of thin tissue sections of KS Y-1 induced tumors. Compared to the frequent mitotic activity in the controls (FIG. 6B), there is evidence of extensive cell death in the tumors of the animals treated with the β-hCG peptides which are comparable to the findings in animals treated with active hCG preparations (FIGS. 6C–E). Some other overlapping β-chain peptides had slight activity (compared to β-hCG peptides 45–57 (SEQ ID NO:6) and 109–119 (SEQ ID NO:7)1. These include peptides which form the :-core (β-hCG peptides 6–40 and 55–90) and one which overlapped satellin A1 (β-hCG peptide 38–57). The a subunit peptide was inactive as were numerous other β-chain peptides such as β-hCG 6–16, 34–49, 57–93, 74–95, 93–100, 100–110, 123–145, and 134–144.

Figure 6F:
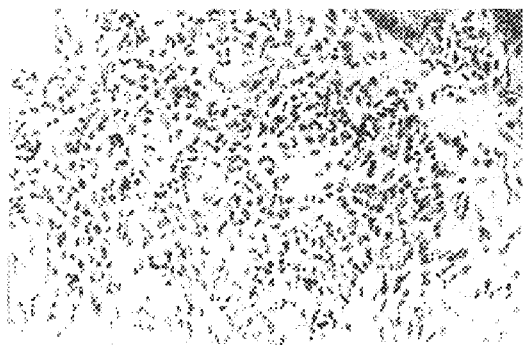
Figure 6G:
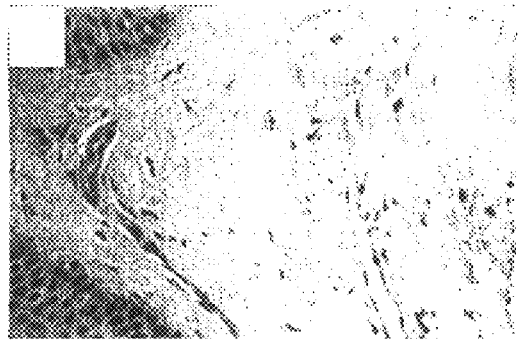
Figure 6H:
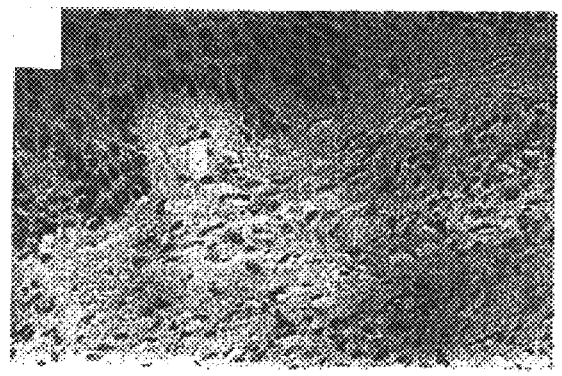

As noted above, some KIDS-KS patients treated by intralesional or systemic injection of some preparations of hCG experience regression of tumor lesions of the skin as well as visceral KS (Hermans et al., 1995, Cellular and Molecular Biology 3:357–364; Gill et al., 1996, NEJM (in press)). Patients receiving these preparations showed macroscopic regression and flattening of KS lesions. In situ immunostaining specific for apoptosis detection in tumor biopsies showed evidence of apoptosis and/or, histologically, complete absence of the KS tumor after 2–3 weeks of hCG therapy as shown in FIGS. 6F, G and H, similar to that seen in the experimental mouse model with the active β-hCG peptides. In control KS tumors treated with diluent only or untreated KS tumor tissues (not shown), there was little evidence of cell death (FIG. 6F).

EFFECTS OF hCG AND β-hCG PEPTIDES ON HEMATOPOIESIS

In addition to the typical decline in $CD4^+$ T cells, cytopenias can occur in HIV infected people affecting one or more hematopoietic lineages associated with deficient progenitor cell growth. This is often made worse by some of the anti-viral therapies currently in use. In contrast, hCG preparations do not inhibit hematopoiesis.

The effect of hCG preparations and peptides was assayed on hematopoietic progenitor cells in vitro. Hematopoietic progenitor cells ($2 \times 10^5$ cell/ml) were isolated from normal bone marrow and cord blood and seeded in methylcellulose. The amount of various hCG preparations and peptides used in these clonogenic assays were: hCG (APL): 200 IU/ml; hCG alpha subunit (Sigma): 100 μg/ml; purified hCG heterodimer CR 127: 200 IU/ml; β-hCG peptide 109–119 (SEQ ID NO:7) (Bachem): 100 μg/ml (83 nmoles); β-hCG peptide 45–57 (SEQ ID NO:6): 100 μg/ml (67 nmoles); β-hCG peptide 45–57c circularized (44–57 with cysteine substituted for the amino acid at position 44) (SEQ ID NO:26j: 100 μg/ml; mixture of scrambled β-hCG peptides 45–57 and 109–119: 100 μg/ml; and crude preparation of native β-hCG: 100 μg/ml. The native commercial preparation of hCG (APL, Wyeth Ayerst) was pre-tested (for anti-UIV and anti-KS activities). Aggregates containing more than 50 cells after 10 days of culture were counted as colonies. As shown in FIGS. 7A–C, the growth of hematopoietic progenitors (Lunardi-Iskandar et al., 1989, .Leukemia Res. 13:573–581) is directly promoted by a commercial preparation of partially purified hCG (APL, Wyeth Ayerst), partially purified native β-chain, and by the synthetic peptides, β-hCG peptide 45–57 (SEQ ID NO:6) and β-hCG peptide 109–119 (SEQ ID NO:7), respectively) and circularized 44–57 with cysteine substituted for the amino acid at position 44 (SEQ ID NO:26)), but not by the pure hCG heterodimer (CR127) nor by the pure (recombinant) β-chain or the α-chain. The following peptides were tested and showed little or no effects in hematopoiesis assays: α-hCG peptide of amino acids 88–92, and the β-hCG peptides of amino acids 6–16, 7–40, 34–49, 38–57, 57–93, 74–95, 100–110, 123–145, 134–144. Additionally, scrambled β-hCG peptides 45–57 (SEQ ID NO:6) and 109–119 (SEQ ID NO:7) showed little inhibition. Thus, these results recapitulate the anti-KS and anti-HIV effects. Each activity is chiefly effected by the satellin peptides. A series of other peptides of the α- and β-chain had no effect (data not shown).

DISCUSSION

New treatment regimens for HIV-1 show that a combination of anti-FIIV compounds which target reverse transcriptase (RT) such as azidothymidine (AZT), lamivudine (3TC), dideoxyinosine (ddI), dideoxycytodine (ddC) used in comubination with an HIV-1 protease inhibitor, have a far greater effect (2 or more logs reduction) on viral load compared to AZT alone (about 1 log reduction) (Persison et al., 1996, *Science* 15:1582–1586). However, long-term use of combinations of these chemicals may lead Lo toxicity, especially to the bone marrow and suppression of CD.8 T cells, which may be essential to the control of HIV, via killer cell activity (Blazevic et al., 1995, *AIDS Res Hump Retrov.ruses* 11:1335–1342) and by the release of suppressive factors, notably the C-C chemokines (Cocchi et al., 1995, *Science* 270:1811–1815). Other concerns in long-term chemical anti-retroviral therapy are the possible development of HIV mutations with partial or complete resistance (Lange, 1995, *AIDS Res Hum Retroviruses* 10:S77–82) and cost.

The discovery of an anti-KS effect of "hCG" was observed in vivo in pregnant Bg-nude mice which did not develop KS as did their male litter mates inoculated at the same time with the KS Y-1 tumor cells. This observation led to clinical trials of intralesional therapy for KS which documented responses in 83% of treated lesions in a dose dependent manner (Hermans et al., 1995, *Cellular and Molecular Biology* 35 3:357–364; Gill et al., 1996, *NEJM (in press)*).

As shown herein, some patients (e.g., PH-VE, FIGS. 3A and B) treated intralesionally with an hCG preparation for KS were noted to have a reduction in viral load and in vitro human cell culture and in vivo animal model data show that some preparations of partially purified hCG, partially purified β-hCG and the active β-hCG peptides (satellin Al and B) have anti-viral, anti-KS and pro-hematopoietic effects.

We found considerable activity with some preparations of the partially purified native heterodimer and the native partially purified whole β-chain, whereas recombinant β-hCG (purified) and highly purified native hCG heterodimer (CRIXY17B and CR127) were inactive. Based on our results with the β-hCG peptides reported here, we suspect that the lower molecular weight species, active portions of them, or possibly larger fragments which include the active amino acid sequences accompany hCG and the β-chain and are not eliminated by some of the purification procedures, thus retaining the anti-viral, anti-KS and pro-hematopoietic effects, but varying among commercial sources. In this respect, it is noteworthy that although the clinical effects of some preparations of hCG described here were obtained with two different commercial sources (APL and Pregnyl), one was usually more active in laboratory tests (APL) at lower concentrations than any other preparation. This hCG preparation, however, also varied from lot to lot in the immunodeficient mouse KS system (data not shown) despite the fact that identical amounts (International Units) were used as assessed by the manufacturer's standard bioassays for the conventional use of hCG.

As noted above, the differences in activities of commercial preparations and the observation of little or no activity with the highly purified hCG heterodimer supplied by NIH might be explained by variation in the amount of β-hCG fragments. This could be the consequence of different methods of preparation or different sources of human urine. For example, free β chain is more abundant in the earliest weeks of pregnancy (Pierce et al., 1981, *Rev. Biochem.* 50:465–495; Kornyei et al., 1993, *Biol Reprod.* 49:1149–1157). We initiated studies to determine the presence of such fragments in the active hCG commercial preparations. By reverse phase HPLC, we did find that one active preparation (one particular lot of hCG-APL) had multiple peaks and does indeed contain β chain components, but the activities defined here could not be recapitulated with any fraction (data not shown). Consequently, we next began studies with a variety of synthetic peptides, and our results show that all the in vitro activities of the preparations of native hCG and the in vivo mouse data are mimicked strongly by satellin Al (β-hCG peptide 45–57 (SEQ ID NO:6)), but not other β- or α-peptides or scrambled 45–57 peptide.

The mechanism of the anti-HIV effect of some preparations of native hCG, and native β-hCG, and of the β fragments on HIV-1 appear, at least in part, to be direct. This is suggested by: 1) the 4n vitro inhibition of HIV-1 infectivity of $CD4^+$ T cells and macrophages; 2) the inhibition of HIV-1 gene transcription in HIV-1. transgenic mice; 2) the rapid clearance of p27 antigen in the acutely SIV infected monkeys treated with hCG; and 4) the decline of plasma virus in some patients treated with some hCG preparations,. However, there was a greater inhibition of in vitro infection of cells with various strains of HIVES compared to inhibition of HIV-1 production from chronically infected cells suggesting that mechanisms, in addition to inhibition of transcription, are also involved. However, indirect effects also cannot be excluded for the anti-SIV/HIV effects observed in the monkey experiments and among responding patients. HIV has anti-hematopoiesis effects (Lunardi-Iskandar et al., 1989, *J. Clin. Invest.* 83:610–615; Louache et al., 1992, *Blood* 180:2991–2999; Geller et al., 1985, *Archs. Path. Lab. Met.* 109:138–145). Based on our findings that hCG and the peptides have pro-hematopoietic effects on progenitors cells of the bone marrow, it is possible that enhanced immune function also may have contributed to the in vivo results.

Some preparations of hCG have beneficial effects against the range of core problems associated with HIV-1 infection. In laboratory tests, KS cells were killed and regression occurred of transplanted KS tumors in mice (Lunardi-Iskandar et al., 1995, *Nature* 375:64–68). A recent-clinical study of escalating dose by intralesional injection of hCG (APL, Wyeth Ayerst) for cutaneous KS skin lesions demonstrated tumor regression in a dose-dependent manner, with 8% responding at the lowest dose (250 IU, 3 times weekly) and 83% at the highest intralesional dose (2000 IU, 3 times weekly) (Gill et al., 1996, *NEJM* (in press)). Results described here also showed regression of KS lesions in a substantial proportion of cases including cases treated with systemic therapy, and even regression of newly developed lesions while on hCG therapy when higher doses were given. It is also noteworthy that regression of visceral lesions occurred in several KS patients with advanced KS.

The clinical data reviewed herein illustrate many of the beneficial effects observed in the laboratory pre-clinical studies. Since the protocols were not designed to systematically study the various beneficial effects of some preparations of hCG as a treatment for HIV infection and since there is variability in dose and source of product, the inferences to be drawn are illustrative of the potential for some commercial preparations of hCG or related products in HIV and KS treatment. As reported elsewhere (Hermans et al., 1995, *Cellular and Molecular Biology* 3:357–364; Gill et al., 1996, *NEJM* (in press)), and confirmed herein, some preparations of hCG induced partial or complete regression of KS lesions in patients treated intralesionally (Hermans et al., 1995, *Cellular and Molecular Biology* 3:357–364) and systemically, including advanced visceral disease. In some HIV-1 positive patients at various stages of HIV infection there was a 0.5 to 2 log reduction in plasma viremia level, and in some cases this effect was sustained with no evidence of development of resistance or toxicity and CD4+ T cell levels increased in some as well. Non-fluid weight gain was a very frequent benefit to patients even with far advanced disease. It is noteworthy that patients such as PH-VE have experienced long term benefits from hCG therapy without oxicity over more than 80 weeks of therapy documenting the safety of this therapeutic approach.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. An isolated peptide:
   (a) consisting essentially of a β-hCG (SEQ ID NO:2) segment selected from the group consisting of 41–54, 45–54, 47–53, 45–58, 41–53, 42–53, 43–53, 44–53, 44–57, 45–53, 46–53, 45–55, 45–56, 47–54, 47–56, 47–58, 48–145 and 58–145 (SEQ ID NOS: 3–5, 18, 8–14, 16, 17, 19, and 21–24 respectively);
   (b) excluding β-hCG (SEQ ID NO:2) amino acids contiguous to said segment; and
   (c) having a therapeutic effect selected from the group consisting of anti-HIV effects, anti-Kaposi's sarcoma effects, and pro-hematopoietic effects.

2. The isolated peptide of claim 1 wherein one or more residues of the segment are substituted by an amino acid or amino acid analog having a side chain with an amino or carboxyl group, the amino or carboxyl group forming a peptide bond with a second sequence of one or more amino acids.

3. The isolated peptide of claim 2 wherein the one or more residues are each substituted by a diaminobutyric acid residue, and the side chain amino group of the diaminobutyric acid residue is peptide bonded to a sequence of one or more proline residues.

4. The isolated peptide of claim 2 wherein the segment includes β-hCG (SEQ ID NO:2) amino acid numbers 47 and 51, and the substitutions by the amino acid or amino acid analog occur at least at residues 47 and 51 of the segment.

5. The isolated peptide of claim 1 which is N-acetylated and/or has a C-terminal amide.

6. The isolated peptide of claim 1 which contains an insertion of, or substitution with, one or more non-classical amino acids.

7. The isolated peptide of claim 1 which contains an insertion of, or substitution with, one or more D-amino acids.

8. The isolated peptide of claim 1 wherein the therapeutic effect includes an anti-HIV effect.

9. The isolated peptide of claim 1 wherein the therapeutic effect includes an anti-Kaposi's sarcoma effect.

10. The isolated peptide of claim 1 wherein the therapeutic effect includes a pro-hematopoietic effect.

11. A peptide:
(a) consisting essentially of a circularized β-hCG (SEQ ID NO:2) segment selected from the group consisting of 41–54, 45–54, 47–53, 45–57, 45–58, 41–53, 42–53, 43–53, 44–53, 44–57, 45–53, 46–53, 45–55, 45–56, 47–54, 47–56, 47–58, 48–145 and 58–145 (SEQ ID NOS: 3–6, 18, 8–17, 19, and 21–24, respectively);
(b) excluding β-hCG (SEQ ID NO:2) amino acids contiguous to said segment; and
(c) having a therapeutic effect selected from the group consisting of anti-HIV effects, anti-Kaposi's sarcoma effects, and pro-hematopoietic effects.

12. The peptide of claim 11 wherein:
(a) a cysteine residue is inserted or substituted for a different amino acid residue in the segment;
(b) the segment contains a second cysteine residue, and
(c) a disulfide bond is formed between the inserted or substituted cysteine residue and the second cysteine residue.

13. The peptide according to claim 11 having at least two cysteine residues, optionally wherein:
(a) at least one cysteine residue has been inserted between two non-cysteine amino acid residues;
(b) at least one cysteine residue has been coupled at an end of the segment; or
(c) at least one non-cysteine amino acid residue has been replaced by a cysteine residue;
wherein two cysteine residues are coupled together by a disulfide bond.

14. The peptide according to claim 11 wherein the segment consists essentially of β-hCG (SEQ ID NO:2) amino acid numbers 44–57 (SEQ ID NO:12), with cysteine substituted for valine at position 44.

15. The peptide according to claim 11 wherein the segment is N-acetylated and/or has a C-terminal amide.

16. The peptide according to claim 11 which contains an insertion of, or substitution with, one or more non-classical amino acids.

17. The peptide according to claim 11 which contains an insertion of, or substitution with, one or more D-amino acids.

18. The peptide according to claim 11 wherein the therapeutic effect includes an anti-HIV effect.

19. The peptide according to claim 11 wherein the therapeutic effect includes an anti-Kaposi's sarcoma effect.

20. The peptide according to claim 11 wherein the therapeutic effect includes a pro-hematopoietic effect.

21. A peptide:
(a) consisting essentially of a branched β-hCG (SEQ ID NO:2) segment selected from the group consisting of β-hCG (SEQ ID NO:2) amino acids 41–54, 45–54, 47–53, 45–57, 45–58, 41–53, 42–53, 43–53, 44–53, 44–57, 45–53, 46–53, 45–55, 45–56, 47–54, 47–56, 47–58, 48–145 and 58–145 (SEQ ID NOS: 3–6, 18, 8–14, 16, 17, 19, and 21–24, respectively);
(b) excluding β-hCG (SEQ ID NO:2) amino acids contiguous to said segment;
(c) having one or more residues of the segment substituted by an amino acid or amino acid analog having a side chain; and
(d) having at least one therapeutic effect selected from the group consisting of anti-HIV effects, anti-Kaposi's sarcoma effects and pro-hematopoietic effects.

22. The peptide of claim 21 wherein:
(a) a cysteine residue is inserted or substituted for a different amino acid residue in the segment;
(b) the segment contains a second cysteine residue, and
(c) a disulfide bond is formed between the inserted or substituted cysteine residue and the second cysteine residue.

23. The peptide of claim 21 wherein:
(a) at least one cysteine residue has been inserted between two non-cysteine amino acid residues;
(b) at least one cysteine residue has been coupled at an end of the segment; or
(c) at least one non-cysteine amino acid residue has been replaced by a cysteine residue;
wherein two cysteine residues are coupled together by a disulfide bond.

24. The peptide of claim 21 wherein one or more residues of the segment are substituted by an amino acid or amino acid analog having a side chain with an amino or carboxyl group, the amino or carboxyl group forming a peptide bond with a second sequence of one or more amino acids.

25. The peptide of claim 24 wherein the one or more residues are each substituted by a diaminobutyric acid residue and the side chain amino group of the diaminobutyric acid residue is peptide bonded to a sequence of one or more proline residues.

26. The peptide of claim 24 wherein the segment consists essentially of amino acid numbers 45–57 (SEQ ID NO:6).

27. The peptide of claim 26 wherein the segment includes positions 47 and 51 and substitutions by the amino acid or amino acid analog occur at least at residues 47 and 51 of the segment.

28. The peptide of claim 21 wherein the segment is N-acetylated and/or has a C-terminal amide.

29. The peptide of claim 21 which contains an insertion of, or substitution with, one or more non-classical amino acids.

30. The peptide of claim 21 which contains an insertion of, or substitution with, one or more D-amino acids.

31. The peptide of claim 21 wherein the therapeutic effect includes an anti-HIV effect.

32. The peptide of claim 21 wherein the therapeutic effect includes an anti-Kaposi's sarcoma effect.

33. The peptide of claim 21 wherein the therapeutic effect includes a pro-hematopoietic effect.

34. A peptide consisting essentially of β-hCG (SEQ ID NO:2) amino acid numbers 44–57 (SEQ ID NO:12) with cysteine substituted for valine at position 44, wherein:
(a) a disulfide bond is formed between the cysteine residue substituted at position 44 and the cysteine residue present at position 57;
(b) the residues at positions 47 and 51 are each substituted by a diaminobutyric acid residue; and
(c) the side chain amino group of the diaminobutyric acid residue is peptide bonded to a proline residue.

35. A method of treating, or preventing the establishment of, a condition selected from the group consisting of HIV infection, Kaposi's sarcoma, and hematopoietic deficiency, in a human subject in need of such treatment or prevention, said method comprising administering to the subject an amount of a peptide:
(a) consisting essentially of a β-hCG (SEQ ID NO:2) segment selected from the group consisting of 41–54, 45–54, 47–53, 45–57, 45–58, 41–53, 42–53, 43–53, 44–53, 44–57, 45–53, 46–53, 45–55, 45–56, 47–54, 47–56, 47–58, 48–145 and 58–145 (SEQ ID NOS: 3–6, 18, 8–14, 16, 17, 19, and 21–24, respectively);
(b) excluding β-hCG (SEQ ID NO:2) amino acids contiguous to said segment; and
(c) having a therapeutic effect selected from the group consisting of anti-HrV effects, anti-Kaposi's sarcoma effects and pro-hematopoietic effects.

36. The method of claim 35 wherein one or more residues of the segment are substituted by an amino acid or amino acid analog having a side chain with an amino or carboxyl group, the amino or carboxyl group forming a peptide bond with a second sequence of one or more amino acids.

37. The method of claim 36 wherein one or more residues of the segment are substituted by a diaminobutyric acid residue, and the side chain amino group of the diaminobutyric acid residue is peptide bonded to a sequence of one or more proline residues.

38. The method of claim 36 wherein the segment consists essentially of βhCG (SEQ ID NO:2) amino acid numbers 45–57 (SEQ ID NO:6).

39. The method of claim 38 wherein the segment includes positions 47 and 51 and substitutions by the amino acid or amino acid analog occur at least at residues 47 and 51 of the segment.

40. The method of claim 35 wherein the segment consists essentially of β-hCG (SEQ ID NO:2) amino acid numbers 45–57 (SEQ ID NO:6).

41. The method of claim 35 wherein the segment is N-acetylated and/or has a C-terminal amide.

42. The method of claim 35 wherein the peptide or protein contains an insertion of, or substitution with, one or more non-classical amino acids.

43. The method of claim 35 wherein the peptide or protein contains an insertion of, or substitution with, one or more D-amino acids.

44. The method of claim 35 wherein the therapeutic effect includes an anti-HIV effect.

45. The method of claim 44 which further comprises administering to the subject a therapeutically effective amount of a chemokine.

46. The method of claim 45 wherein the chemokine is selected from one or more of the group consisting of RANTES, MIP-1α and MIP-1β.

47. The method of claim 44 which further comprises administering to the subject an antiviral drug other than β-hCG (SEQ ID NO:2).

48. The method of claim 47 wherein the anti-viral drug is selected from one or more of the group consisting of AZT, 3TC, ddl, ddC, 3TC, and sequinavir.

49. The method of claim 32 wherein the peptide is administered intramuscularly.

50. The method of claim 35 wherein the therapeutic effect includes an anti-Kaposi's sarcoma effect.

51. The method of claim 35 wherein the therapeutic effect includes a pro-hematopoietic effect.

52. A method of treating, or preventing the establishment of, a condition selected from the group consisting of HIV infection, Kaposi's sarcoma, and hematopoietic deficiency, in a human subject in need of such treatment or prevention, said method comprising administering to the subject an amount of a peptide:
(a) consisting essentially of a circularized β-hCG (SEQ ID NO:2) segment selected from the group consisting of 41–54, 45–54, 47–53, 45–57, 45–58, 41–53, 42–53, 43–53, 44–53, 44–57, 45–53, 46–53, 45–55, 45–56, 47–54, 47–56, 47–58, 48–145 and 58–145 (SEQ ID NOS: 3–6, 18, 8–14, 16, 17, 19, and 21–24, respectively);
(b) excluding β-hCG (SEQ ID NO:2) amino acids contiguous to said segment; and
(c) having a therapeutic effect selected from the group consisting of anti-HIV effects, anti-Kaposi's sarcoma effects and pro-hematopoietic effects.

53. The method of claim 52 wherein:
(a) a cysteine residue is inserted or substituted for a different amino acid residue in the segment;
(b) the segment contains a second cysteine residue; and
(c) a disulfide bond is formed between the inserted or substituted cysteine residue and the second cysteine residue present in the segment.

54. The method of claim 52 wherein the segment has at least two cysteine residues, optionally wherein:
(a) at least one cysteine residue has been inserted between two non-cysteine amino acid residues;
(b) at least one cysteine residue has been coupled at an end of the segment; or
(c) at least one non-cysteine amino acid residue has been replaced by a cysteine residue;
wherein two cysteine residues are coupled together by a disulfide bond.

55. The method of claim 52 wherein one or more residues of the segment are substituted by an amino acid or amino acid analog having a side chain with an amino or carboxyl group, the amino or carboxyl group forming a peptide bond with a second sequence of one or more amino acids.

56. The method of claim 52 wherein one or more residues of the segment are substituted by a diaminobutyric acid residue and the side chain amino group of the diaminobutyric acid residue is peptide bonded to a sequence of one or more proline residues.

57. The method of claim 55 wherein the segment consists essentially of amino acid numbers 45–57 (SEQ ID NO:6) with cysteine substituted for valine at position 44.

58. The method of claim 55 wherein the segment includes positions 47 and 51 and substitutions by the amino acid or amino acid analog occur at least at residues 47 and 51 of the segment.

59. The method of claim 52 wherein the segment is N-acetylated and/or has a C-terminal amide.

60. The method of claim 52 wherein the peptide contains an insertion of, or substitution with, one or more non-classical amino acids.

61. The method of claim 52 wherein the peptide contains an insertion of, or substitution with, one or more D-amino acids.

62. The method of claim 52 wherein the therapeutic effect includes an anti-HIV effect.

63. The method of claim 62 which further comprises administering to the subject a therapeutically effective amount of a chemokine.

64. The method of claim 62 wherein the chemokine is selected from one or more of the group consisting of RANTES, MIP-1α and MIP-1 β.

65. The method of claim 62 which further comprises administering to the subject an antiviral drug other than β-hCG (SEQ ID NO:2).

66. The method of claim 62 wherein the anti-viral drug is selected from one or more of the group consisting of AZT, 3TC, ddl, ddC, 3TC, and sequinavir.

67. The method of claim 52 wherein the anti-cancer effect includes an anti-Kaposi's sarcoma effect.

68. The method of claim 52 wherein the therapeutic effect includes a pro-hematopoietic effect.

69. The method of claim 52 wherein the β-hCG (SEQ ID NO:2) preparation is administered intramuscularly.

70. A pharmaceutical composition comprising:
(a) a peptide:
(i) consisting essentially of a β-hCG (SEQ ID NO:2) segment selected from the group consisting of 41–54, 45–54, 47–53, 45–58, 41–53, 42–53, 43–53, 44–53, 44–57, 45–53, 46–53, 45–55, 45–56, 47–54, 47–56, 47–58, 48–145 and 58–145 (SEQ ID NOS: 3–5, 18, 8–14, 16, 17, 19, and 21–24, respectively);
(ii) excluding β-hCG (SEQ ID NO:2) amino acids contiguous to said segment; and
(iii) having a therapeutic effect selected from the group consisting of anti-HIV effects, anti-Kaposi's sarcoma effects and pro-hematopoietic effects; and
(b) a pharmaceutically acceptable carrier.

71. The pharmaceutical composition of claim 70 wherein one or more residues are substituted by an amino acid or amino acid analog having a side chain with an amino or carboxyl group, the amino or carboxyl group forming a peptide bond with a second sequence of one or more amino acids.

72. The pharmaceutical composition of claim 70 wherein the one or more residues are each substituted by a diaminobutyric acid residue and the side chain amino group of the diaminobutyric acid residue is peptide bonded to a sequence of one or more proline residues.

73. The pharmaceutical composition of claim 70 wherein the segment includes positions 47 and 51 and substitutions by the amino acid or amino acid analog occur at least at residues 47 and 51 of the β-hCG segment.

74. The pharmaceutical composition of claim 70 wherein the therapeutic effect includes an anti-HIV effect.

75. The pharmaceutical composition of claim 70 wherein the therapeutic effect includes an anti-Kaposi's sarcoma effect.

76. The pharmaceutical composition of claim 70 wherein the therapeutic effect includes a pro-hematopoietic effect.

77. A pharmaceutical composition comprising:
(a) a peptide:
(i) consisting essentially of a circularized β-hCG (SEQ ID NO:2) segment selected from the group consisting of 41–54, 45–54, 47–53, 45–57, 45–58, 41–53, 42–53, 43–53, 44–53, 44–57, 45–53, 46–53, 45–55, 45–56, 47–54, 47–56, 47–58, 48–145 and 58–145 (SEQ ID NOS: 3–6, 18, 8–14, 16, 17, 19, and 21–24, respectively);
(ii) excluding β-hCG (SEQ ID NO:2) amino acids contiguous to said segment; and
(iii) having a therapeutic effect selected from the group consisting of anti-HIV effects, anti-Kaposi's sarcoma effects, and pro-hematopoietic effects; and
(b) a pharmaceutically acceptable carrier.

78. The pharmaceutical composition of claim 77 wherein a cysteine residue is inserted or substituted for a different amino acid residue in the segment, the segment containing a second cysteine residue, and wherein a disulfide bond is formed between the inserted or substituted cysteine residue and the second cysteine residue.

79. The pharmaceutical composition of claim 77 wherein the peptide has at least two cysteine residues, optionally wherein:
(a) at least one cysteine residue has been inserted between two non-cysteine amino acid residues;
(b) at least one cysteine residue has been coupled at an end of the segment; or
(c) at least one non-cysteine amino acid residue has been replaced by a cysteine residue; and wherein two cysteine residues are coupled together by a disulfide bond.

80. The pharmaceutical composition of claim 77 wherein the amino acid sequence of circularized peptide consists essentially of β-hCG (SEQ ID NO:2) amino acid numbers 44–57 (SEQ ID NO:12), with cysteine substituted for valine at position 44.

81. The pharmaceutical composition of claim 77 wherein the therapeutic effect includes an anti-HIV effect.

82. The pharmaceutical composition of claim 77 wherein the therapeutic effect includes an anti-Kaposi's sarcoma effect.

83. The pharmaceutical composition of claim 77 wherein the therapeutic effect includes a pro-hematopoietic effect.

84. A method of treating, or preventing the establishment of, a condition selected from the group consisting of HIV infection, Kaposi's sarcoma, and hematopoietic deficiency, in a human subject in need of such treatment or prevention, said method comprising administering to the subject a pharmaceutical composition comprising:
(a) a peptide:
(i) consisting essentially of a β-hCG (SEQ ID NO:2) segment selected from the group consisting of 41–54, 45–54, 47–53, 45–57, 45–58, 41–53, 42–53, 43–53, 44–53, 44–57, 45–53, 46–53, 45–55, 45–56, 47–54, 47–56, 47–58, 48–145 and 58–145 (SEQ IDNOS: 3–6, 18, 8–14, 16, 17, 19, and 21–24, respectively);
(ii) excluding β-hCG (SEQ ID NO:2) amino acids contiguous to said segment; and
(iii) having a therapeutic effect selected from the group consisting of anti-HIV effects, anti-Kaposi's sarcoma effects and pro-hematopoietic effects; and
(b) a pharmaceutically acceptable carrier.

85. The method of claim 84 wherein one or more residues of the peptide are substituted by an amino acid or amino acid analog having a side chain with an amino or carboxyl group, the amino or carboxyl group forming a peptide bond with a second sequence of one or more amino acids.

86. The method of claim 84 wherein one or more residues of the peptide are each substituted by a diaminobutyric acid residue and the side chain amino group of the diaminobutyric acid residue is peptide bonded to a sequence of one or more proline residues.

87. The method of claim 84 wherein the segment consists essentially of amino acid numbers 45–57 (SEQ ID NO:6).

88. The method of claim 84 wherein the segment includes positions 47 and 51 and substitutions by the amino acid or amino acid analog occur at least at residues 47 and 51 of the segment.

89. The method of claim 84 wherein the therapeutic effect includes an anti-HIV effect.

90. The pharmaceutical composition of claim 84 wherein the therapeutic effect includes an anti-Kaposi's sarcoma effect.

91. The method of claim 84 wherein the therapeutic effect includes a pro-hematopoietic effect.

92. A method of treating, or preventing the establishment of, a condition selected from the group consisting of HIV infection, Kaposi's sarcoma, and hematopoietic deficiency, in a human subject in need of such treatment or prevention, said method comprising administering to the subject a pharmaceutical composition comprising:
(a) a peptide:
(i) consisting essentially of a circularized β-hCG (SEQ ID NO:2) segment selected from the group consisting of 41–54, 45–54, 47–53, 45–57, 45–58, 41–53, 42–53, 43–53, 44–53, 44–57, 45–53, 46–53, 45–55, 45–56, 47–54, 47–56, 47–58, 48–145 and 58–145 (SEQ ID NOS: 3–6, 18, 8–14,16,17, 19, and 21–24, respectively);

(ii) excluding β-hCG (SEQ ID NO:2) amino acids contiguous to said segment; and (iii) having a therapeutic effect selected from the group consisting of anti-HIV effects, anti-Kaposi's sarcoma effects and pro-hematopoietic effects; and (b) a pharmaceutically acceptable carrier.

93. The method of claim 92 wherein a cysteine residue is inserted or substituted for a different amino acid residue in the segment, the segment containing a second cysteine residue, and wherein a disulfide bond is formed between the inserted or substituted cysteine residue and the second cysteine residue present in the one or more segments of the sequence.

94. The method of claim 92 wherein the circularized peptide has at least two cysteine residues, optionally wherein:

(a) at least one cysteine residue has been inserted between two non-cysteine amino acid residues;

(b) at least one cysteine residue has been coupled at an end of the segment; or (c) at least one non-cysteine amino acid residue has been replaced by a cysteine residue; and wherein two cysteine residues are coupled together by a disulfide bond.

95. The method of claim 92 wherein the amino acid sequence of circularized peptide consists essentially of β-hCG (SEQ ID NO:2) amino acid numbers 44–57 (SEQ ID NO:12), with cysteine substituted for valine at position 44.

96. The method of claim 92 wherein one or more residues of the isolated peptide are substituted by an amino acid or amino acid analog having a side chain with an amino or carboxyl group, the amino or carboxyl group forming a peptide bond with a second sequence of one or more amino acids.

97. The method of claim 92 wherein one or more residues of the isolated peptide are substituted by a diaminobutyric acid residue and the side chain amino group of the diaminobutyric acid residue is peptide bonded to a sequence of one or more proline residues.

98. The method of claim 96 wherein the segment consists essentially of amino acid numbers 45–57 (SEQ ID NO:6) with cysteine substituted for valine at position 44.

99. The method of claim 98 wherein the segment includes positions 47 and 51 and substitutions by the amino acid or amino acid analog occur at least at residues 47 and 51 of the segment.

100. The method of claim 92 wherein the therapeutic effect includes an anti-HIV effect.

101. The method of claim 92 wherein the therapeutic effect includes an anti-Kaposi's sarcoma effect.

102. The method of claim 92 wherein the therapeutic effect includes a pro-hematopoietic effect.

103. A method for treating, or preventing the establishment of, a condition selected from the group consisting of HIV infection, Kaposi's sarcoma and hematopoietic deficiency in a human subject in need thereof comprising administering to the subject an amount of a peptide comprising an amino acid sequence consisting essentially of β-hCG (SEQ ID NO:2) amino acid numbers 45–57, and with the proviso that the peptide does not consist of the entire β-hCG (SEQ ID NO:2) chain.

104. The method of claim 103 wherein one or more residues of the sequence are substituted by an amino acid or amino acid analog having a side chain with an amino or carboxyl group, the amino or carboxyl group forming a peptide bond with a second sequence of one or more amino acids.

105. The method of claim 104 wherein the one or more residues are each substituted by a diaminobutyric acid residue and the side chain amino group of the diaminobutyric acid residue is peptide bonded to a sequence of one or more proline residues.

106. The method of claim 104 wherein the segment includes positions 47 and 51 and substitutions by the amino acid or amino acid analog occur at least at residues 47 and 51 of the sequence.

107. The method of claim 103 wherein the peptide is circularized.

108. The method of claim 107 wherein:

(a) a cysteine residue is inserted or substituted for a different amino acid residue in the sequence;

(b) the sequence contains a second cysteine residue, and (c) a disulfide bond is formed between the inserted or substituted cysteine residue and the second cysteine residue.

109. The method of claim 107 wherein the peptide has at least two cysteine residues, optionally wherein:

(a) at least one cysteine residue has been inserted between two non-cysteine amino acid residues;

(b) at least one cysteine residue has been coupled at an end of the amino acid sequence; or (c) at least one non-cysteine amino acid residue has been replaced by a cysteine residue;

wherein two cysteine residues are coupled together by a disulfide bond.

110. The method of claim 107 wherein cysteine is substituted for valine at position 44.

111. The method of claim 107 wherein one or more residues of the segment are substituted by an amino acid or amino acid analog having a side chain with an amino or carboxyl group, the amino or carboxyl group forming a peptide bond with a sequence of one or more amino acids.

112. The method of claim 111 wherein the one or more residues are each substituted by a diaminobutyric acid residue and the side chain amino group of the diaminobutyric acid residue is peptide bonded to a sequence of one or more proline residues.

113. The method of claim 111 wherein the segment includes positions 47 and 51 and substitutions by the amino acid or amino acid analog occur at least at β-hCG (SEQ ID NO:2) residues 47 and 51 of the segment.

114. The method of claim 111 wherein the segment includes positions 47 and 51 and substitutions by the diaminobutyric acid residues occur at least at β-hCG (SEQ ID NO:2) residues 47 and 51, and the side chain amino group of the diaminobutyric acid residue is peptide bonded to a sequence of one or more proline residues.

115. A peptide consisting essentially of the amino acid sequence Leu-Gln-Gly-Val-Leu-Pro-Ala-Leu-Pro-Gln-Val-Val-Cys (SEQ ID NO:6) wherein the glycine at position 3 and the alanine at position 7 have each been replaced by Dab(Pro), where Dab(Pro) indicates a proline peptide-bonded to the amino side chain of Dab.

116. The peptide of claim 115 consisting of the amino acid sequence Leu-Gln-Gly-Val-Leu-Pro-Ala-Leu-Pro-Gln-Val-Val-Cys (SEQ ID NO:6) wherein the glycine at position 3 and the alanine at position 7 have each been replaced by Dab(Pro), where Dab(Pro) indicates a proline peptide-bonded to the amino side chain of Dab.

117. A peptide consisting essentially of the amino acid sequence Cys-Leu-Gln-Gly-Val-Leu-Pro-Ala-Leu-Pro-Gln-Val-Val-Cys (SEQ ID NO:26), wherein the terminal Cys residues are linked together a disulfide bond.

118. The peptide of claim 117 consisting of the amino acid sequence Cys-Leu-Gln-Gly-Val-Leu-Pro-Ala-Leu-Pro-Gln-Val-Val-Cys (SEQ ID NO:26), wherein the terminal Cys residues are linked together a disulfide bond.

119. A peptide consisting essentially of the amino acid sequence Thr-Cys-Asp-Asp-Pro-Arg-Phe-Gln-Asp-Ser-Ser (SEQ.ID NO:7).

120. The peptide of claim 119 consisting of the amino acid sequence Thr-Cys-Asp-Asp-Pro-Arg-Phe-Gln-Asp-Ser-Ser (SEQ.ID NO:7).

121. A peptide comprising a β-hCG (SEQ ID NO:2) segment selected from the group consisting of 41–54, 45–54, 47–53, 45–58, 41–53, 42–53, 43–53, 44–53, 44–57, 45–53, 46–53, 4–55, 45–56, 47–54, 47–56, 47–58, and 58–145 (SEQ ID NOS: 3–5, 18, 8–14, 16, 17, 19, 21, 22 and 24, respectively), wherein said segment is not flanked by natively occurring β-hCG sequences.

122. A peptide:
(i) consisting essentially of a βhCG (SEQ ID NO:2) segment selected from the group consisting of 41–54, 45–54, 47–53, 45–58, 41–53, 4–53, 43–53, 44–53, 44–57, 45–53, 46–53, 45–55, 45–56, 47–54, 47–56, 47–58, and 58–145 (SEQ ID NOS: 3–5, 18, 8–14, 16, 17, 19, 21, 22 and 24, respectively);
(ii) excluding β-hCG (SEQ ID NO:2) amino acids contiguous to said segment; and
(iii) having a therapeutic effect selected from the group consisting of anti-HIV effects, anti-cancer effects and pro-hematopoietic effects.

* * * * *

UNITED STATES PATENT AND TRADEMARK OFFICE
CERTIFICATE OF CORRECTION

PATENT NO. : 6,319,504 B1
DATED : November 20, 2001
INVENTOR(S) : Robert C. Gallo et al.

It is certified that error appears in the above-identified patent and that said Letters Patent is hereby corrected as shown below:

Title page,
Item [56], References Cited, OTHER PUBLICATIONS,
Lyer et al. reference, "Pepetide" should be -- Peptide --

Column 2,
Line 34, "dd1" should be -- ddI --
Line 47, "suppressive 35 factors" should be -- suppressive factors --
Line 59, "therapy. Attempts" should be -- therapy. ¶ Attempts --

Column 3,
Line 35, "W092/22,654" should be -- W092/22,654 --

Column 6,
Line 2, "macagues" should be -- macaques --
Line 66, "mmol/ml" should be -- nmol/ml --

Column 7,
Line 63, "IU/mrl" should be -- IU/ml --

Column 8,
Line 31, "106" should be -- $10^6$ --
Line 52, "hematopojesis" should be -- hematopoiesis --
Line 60, "giranulo" should be -- granulo --

Column 9,
Line 5, "tiyde" should be -- tide --
Line 10, "(ID NO:26)" should be -- (SEQ ID NO:26) --

Column 10,
Line 28, "20, or amino" should be -- 20, or 30 amino --
Line 39, "which, consist" should be -- which consist --

UNITED STATES PATENT AND TRADEMARK OFFICE
CERTIFICATE OF CORRECTION

PATENT NO. : 6,319,504 B1
DATED : November 20, 2001
INVENTOR(S) : Robert C. Gallo et al.

It is certified that error appears in the above-identified patent and that said Letters Patent is hereby corrected as shown below:

Column 11,
Line 20, "By" should be -- by --
Line 21, "8769-019)] entitled" should be -- 8769-019)], and in the U.S. Patent Applications entitled --
Line 45, "mcre" should be -- more --

Column 12,
Line 17, "β-amino" should be -- α-amino --

Column 13,
Line 62, "acid-to" should be -- acid to --
Line 63, "N-β-tert-butyloxycarbonyl" should be -- N-α-tert-butyloxycarbonyl --
Line 65, "mtlain" should be -- main --

Column 14,
Line 3, "dinmethylaminopyridine" should be -- dimethylaminopyridine --
Line 24, "analog. In" should be -- analog. ¶ In --
Line 33, "cysteinie" should be -- cysteine --

Column 15,
Line 7, "alLyl" should be -- allyl --
Line 25, "*Jun.*" should be -- Jun. --
Line 28, "*pp.*" should be -- pp. --
Line 43, "the. source" should be -- the source --
Line 67, "Cell" should be -- *Cell* --

Column 16,
Line 2, "Hepatology" should be -- *Hepatology* --
Line 5, "immunoqlobulin" should be -- immunoglobulin --
Line 7, "Nature" should be -- *Nature* --
Line 10, "et al., 15 1986" should be -- et al., 1986 --
Line 10, "Cell" should be -- *Cell* --
Line 12, "1987,. Genes" should be -- 1987, *Genes* --

UNITED STATES PATENT AND TRADEMARK OFFICE
CERTIFICATE OF CORRECTION

PATENT NO. : 6,319,504 B1
DATED : November 20, 2001
INVENTOR(S) : Robert C. Gallo et al.

It is certified that error appears in the above-identified patent and that said Letters Patent is hereby corrected as shown below:

Column 16 (cont.),
Line 14, "1539" should be -- 1639 --
Line 15, "1-antitr-ypsin" should be -- 1-antitrypsin --
Line 19, "Cell" should be -- *Cell* --
Line 22, "Cell" should be -- *Cell* --
Line 63, "*Cytokine* 30 3:165-183)." should be -- *Cytokine* 3:165-183). --

Column 17,
Line 14, "to hCG," should be -- to: hCG, --
Line 18, "nucleic-acids" should be -- nucleic acids --

Column 18,
Line 32, "adninistered" should be -- administered --
Line 42, "MIP-1αand" should be -- MIP-1α and --
Line 51, "Profasim™" should be -- Profasi™ --
Line 58, "onftra" should be -- infra --
Line 66, "R" should be -- β --
Line 66, "peptides. hCG" should be -- peptides. ¶ hCG --

Column 19,
Line 28, "*Tolstoshev*" should be -- Tolstoshev --
Line 41, "pepticie" should be -- peptide --
Line 42, "promtoter" should be -- promoter --
Line 51, "Zijistra" should be -- Zijlstra --

Column 20,
Line 13, "W092/06180" should be -- WO92/06180 --
Line 14, "W092/20316" should be -- WO92/20316 --
Line 15, "W093/14188" should be -- WO93/14188 --
Line 15, "W093/" should be -- WO93/ --
Line 60, "Cell" should be -- *Cell* --

UNITED STATES PATENT AND TRADEMARK OFFICE
CERTIFICATE OF CORRECTION

PATENT NO. : 6,319,504 B1
DATED : November 20, 2001
INVENTOR(S) : Robert C. Gallo et al.

It is certified that error appears in the above-identified patent and that said Letters Patent is hereby corrected as shown below:

Column 21,
Line 18, *"Enzyrmol.* " should be -- *Enzymol.* --
Line 18, "Kline" should be -- Cline --
Line 53, "H7V" should be -- HIV --
Line 57, "descrIbed" should be -- described --

Column 22,
Line 31, "antis" should be -- anti- --
Line 67, "Skcin" should be -- Skin --

Column 23,
Line 7, "Pediatric Res." should be -- *Pediatric Res.* --

Column 24,
Line 17, "ommaya" should be -- Ommaya --
Line 34, "ibid.) In" should be -- ibid.) ¶ In --
Line 45, "Eeppas" should be -- Peppas --

Column 25,
Line 48, "here" should be -- Where --
Line 55, "phosphoric$_1$" should be -- phosphoric, --
Line 56, "Smith" should be -- with --

Column 26,
Line 24, "ref lE.cts" should be -- reflects --
Line 36, "nematopoiesis" should be -- hematopoiesis --
Line 58, "ar" should be -- gag --

UNITED STATES PATENT AND TRADEMARK OFFICE
CERTIFICATE OF CORRECTION

PATENT NO. : 6,319,504 B1
DATED : November 20, 2001
INVENTOR(S) : Robert C. Gallo et al.

It is certified that error appears in the above-identified patent and that said Letters Patent is hereby corrected as shown below:

Column 27,
Line 1, "ATDS Res. Huin. Retroviruses" should be -- *AIDS Res. Hum. Retroviruses* --
Line 2, "AIDS Res. Hum. Retroviruses" should be -- *AIDS Res. Hum. Retroviruses* --
Lines 17-18, "milk. ¶ Blood" should be -- milk. Blood --
Line 23, "CDNA" should be -- cDNA --
Line 32, "southern" should be -- Southern --
Line 36, "RLNA" should be -- mRNA --
Line 37, "MRNA" should be -- mRNA --
Line 54, "HIV-i" should be -- HIV-1 --

Column 28,
Line 2, "an.L-" should be -- ani- --
Line 20, "SIV$_{mac}$251," should be -- SIV$_{mac251}$, --
Line 51, "hGC; preparation" should be -- hCG preparation --

Column 29,
Line 2, "*(in press); Harris, P.J.,*" should be -- (in press), Harris, P.J., --
Line 6, "Nature" should be -- *Nature* --
Line 27, "hCC" should be -- hCG --
Line 35, "Blood" should be -- *Blood* --
Line 54, "patient-has" should be -- patient has --
Line 58, "KSo" should be -- KS --
Line 59, "IU/week). Patient" should be -- IU/week). ¶ Patient --

Column 30,
Line 6, "mm$^{3.}$" should be -- 10 mm$^3$, --
Line 42, "mm$^{3.}$" should be -- mm$^3$. --
Line 64, "B1-HI77" should be -- B1-HIV --

Column 31,
Line 57, "P0-CJP" should be -- PO-CJP --

Column 33,
Line 42, "heG" should be -- hCG --

UNITED STATES PATENT AND TRADEMARK OFFICE
CERTIFICATE OF CORRECTION

PATENT NO. : 6,319,504 B1
DATED : November 20, 2001
INVENTOR(S) : Robert C. Gallo et al.

It is certified that error appears in the above-identified patent and that said Letters Patent is hereby corrected as shown below:

Column 34,
Line 3, "Science" should be -- *Science* --
Line 6, "Science" should be -- *Science* --

Column 35,
Line 15, "call" should be -- cell --
Line 15, "Pith" should be -- with --
Line 47, "also.had" should be -- also had --
Line 48, "IU/mi" should be -- IU/ml --

Column 36,
Line 4, "0" should be -- β --
Line 16, "hich" should be -- which --
Line 21, "lin" should be -- in --
Line 27, "a" should be -- α --
Line 42, "shown) include-" should be -- shown), include- --
Line 64, "430Ensoli" should be -- 430;Ensoli --

Column 37,
Line 1, "anti--viral" should be -- anti-viral --
Line 3, "ir" should be -- in --
Line 51, "Gaithersburg Md." should be -- Gaithersburg, Md. --

Column 38,
Line 2, "NO:7)1." should be -- NO:7)). --
Line 2, ":-core" should be -- β-core --
Line 4, "a" should be -- α --
Line 8, "KIDS" should be -- AIDS --
Line 43, "NO:26j:" should be -- NO:26): --
Line 47, "anti-UIV" should be -- anti-HIV --
Line 49, "colonies.  As" should be -- colonies. ¶ As --
Line 51, "1989, .Leukemia Res." should be -- 1989, *Leukemia Res.* --

UNITED STATES PATENT AND TRADEMARK OFFICE
CERTIFICATE OF CORRECTION

PATENT NO. : 6,319,504 B1
DATED : November 20, 2001
INVENTOR(S) : Robert C. Gallo et al.

It is certified that error appears in the above-identified patent and that said Letters Patent is hereby corrected as shown below:

Column 39,
Line 6, "FIIV" should be -- HIV --
Line 8, "dd1" should be -- ddI --
Line 9, "comubination" should be -- combination --
Line 11, "Persison" should be -- Perelson --
Line 13, "Lo" should be -- to --
Line 14, "CD.8" should be -- $CD8^+$ --
Line 16, "*Hump*" should be -- *Hum.* --
Line 17, "*v.ruses*" should be -- *viruses*--
Line 31, "*Biology* 35 3:357-364;" should be -- *Biology* 3:357-364; --

Column 40,
Line 21, "4n" should be -- in --
Line 23, "HIV-1. transgenic" should be -- HIV-1 transgenic --
Line 23, "2)" should be -- 3) --
Line 26, "preparations,." should be -- preparations. --
Line 28, "HIVES" should be -- HIV-1 --
Line 46, "Nature" should be -- *Nature* --
Line 46, "recent-clinical" should be -- recent clinical --

Column 41,
SEQ ID NO:1, residue No. 76, codons: "CTG" should be -- GTG --
SEQ ID NO:1, residue No. 76, "Leu" should be -- Val --

Column 42,
Line 2, "oxicity" should be -- toxicity --

Column 44,
SEQ ID NO:2, residue No. 76, "Leu" should be -- Val --

Column 51,
SEQ ID NO: 23, residue No. 29, "Leu" should be -- Val --

Column 53,
SEQ ID NO: 24, residue No. 19, "Leu" should be -- Val --

UNITED STATES PATENT AND TRADEMARK OFFICE
CERTIFICATE OF CORRECTION

PATENT NO. : 6,319,504 B1
DATED : November 20, 2001
INVENTOR(S) : Robert C. Gallo et al.

It is certified that error appears in the above-identified patent and that said Letters Patent is hereby corrected as shown below:

Column 57,
Line 6, "anti-HrV" should be -- anti-HIV --
Line 18, "βhCG" should be -- β-hCG --
Line 48, "dd1" should be -- ddI --
Line 49, "32" should be -- 35 --

Column 58,
Line 61, "dd1" should be -- ddI --

Column 60,
Line 27, "IDNOS:" should be -- ID NOS: --

Column 63,
Line 2, "GIn" should be -- Gln --
Line 10, "GIn" should be -- Gln --
Line 18, "4-55" should be -- 45-55 --

Column 64,
Line 5, "βhCG" should be -- β-hCG --
Line 7, "4-53" should be -- 42-53 --

Signed and Sealed this

Seventeenth Day of December, 2002

JAMES E. ROGAN
*Director of the United States Patent and Trademark Office*